US010544436B2

(12) United States Patent
Bradshaw

(10) Patent No.: US 10,544,436 B2
(45) Date of Patent: Jan. 28, 2020

(54) COMPOSITIONS AND METHODS FOR BIOLOGICAL PRODUCTION OF METHIONINE

(71) Applicant: Trelys, Inc., Hayward, CA (US)

(72) Inventor: Jill Bradshaw, Hayward, CA (US)

(73) Assignee: Trelys, Inc., Hayward, CA (US)

( * ) Notice: Subject to any disclaimer, the term of this patent is extended or adjusted under 35 U.S.C. 154(b) by 116 days.

(21) Appl. No.: 15/571,777

(22) PCT Filed: May 6, 2016

(86) PCT No.: PCT/US2016/031318
§ 371 (c)(1),
(2) Date: Nov. 3, 2017

(87) PCT Pub. No.: WO2016/179545
PCT Pub. Date: Nov. 10, 2016

(65) Prior Publication Data

US 2018/0163240 A1 Jun. 14, 2018

Related U.S. Application Data

(60) Provisional application No. 62/157,797, filed on May 6, 2015.

(51) Int. Cl.

| | |
|---|---|
| ***C12P 13/12*** | (2006.01) |
| ***C12N 9/12*** | (2006.01) |
| ***C12N 15/74*** | (2006.01) |
| ***C07K 14/195*** | (2006.01) |
| ***C12N 9/88*** | (2006.01) |
| ***C12N 9/02*** | (2006.01) |
| ***C12M 1/00*** | (2006.01) |

(52) U.S. Cl.
CPC ............ *C12P 13/12* (2013.01); *C07K 14/195* (2013.01); *C12M 29/00* (2013.01); *C12N 9/0095* (2013.01); *C12N 9/1217* (2013.01); *C12N 9/88* (2013.01); *C12N 15/74* (2013.01); *C12Y 207/02004* (2013.01)

(58) Field of Classification Search
None
See application file for complete search history.

(56) References Cited

U.S. PATENT DOCUMENTS

| | | | |
|---|---|---|---|
| 6,299,774 | B1 | 10/2001 | Ainsworth et al. |
| 2010/0120104 | A1 | 5/2010 | Reed |

FOREIGN PATENT DOCUMENTS

| | | | |
|---|---|---|---|
| JP | 6-277081 | | 4/1994 |
| JP | 2007-68437 | | 3/2007 |
| WO | 20080013432 | A1 | 1/2008 |
| WO | 20110139804 | A2 | 11/2011 |
| WO | 2013059362 | A1 | 4/2013 |
| WO | 2013090769 | A2 | 6/2013 |
| WO | 20130120685 | A1 | 8/2013 |
| WO | 2013148348 | A1 | 10/2013 |
| WO | 2014012055 | A1 | 1/2014 |
| WO | 2014047209 | A1 | 3/2014 |
| WO | 2014058761 | A1 | 4/2014 |
| WO | 2014062703 | A1 | 4/2014 |
| WO | 2014066670 | A1 | 5/2014 |
| WO | 20150103497 | A1 | 7/2014 |
| WO | 2014138419 | A1 | 9/2014 |
| WO | 2014145194 | A2 | 9/2014 |
| WO | 2014205146 | A1 | 12/2014 |
| WO | 2015109221 | A1 | 7/2015 |
| WO | 2015109257 | A1 | 7/2015 |
| WO | 2015109265 | A1 | 7/2015 |

OTHER PUBLICATIONS

Examination Report dated Feb. 15, 2018 in EP 2015701433.3, 8 pages.

Office Action dated Apr. 11, 2018 for U.S. Appl. No. 15/109,086, 15 pages.

Examination Report dated Dec. 6, 2018 in JP 2016-562462, 15 pages.

Examination Report dated Mar. 6, 2019 in EP 2016725977.9, 12 pages.

Liu, et al., "The Structural Basis for Allosteric Inhibition of a Threonine-sensitive Aspartokinase," J Biol Chem, 2008, pp. 16216-16225, vol. 283, No. 23.

Office Action dated Jan. 18, 2019 in U.S. Appl. No. 15/109,086, 20 pages.

Sarmiento, et al., "Genetic Systems for Hydrogenotrophic Microorganisms," Methods in Enzymology, 2011, pp. 43-73, vol. 494.

Thauer, "The Wolfe cycle comes full circle," PNAS, 2012, pp. 15084-15085, vol. 109, No. 38.

Examination Report dated Dec. 28, 2018 in SG 11201708741Y, 8 pages.

Anastassiadis, "L-Lysine Fermentation." Recent Patents on Biotechnology, 2007, pp. 11-24, vol. 1.

Becker, et al., "From zero to hero—design-based systems metabolic engineering of Corynebacterium glutamicum for L-lysine production." Metab. Eng., 2011, pp. 159-168, vol. 13, No. 2.

Born, et al., "Enzyme-catalyzed acylation of homoserine: mechanistic characterization of the *Escherichia coli* metA-encoded homoserine transsuccinylase." Biochem., 1999, pp. 14416-14423, vol. 38, No. 43.

Chaban, et al., "Systematic deletion analyses of the fla genes in the flagella operon identify several genes essential or proper assembly and function of flagella in the archaeon, Methanococcus maripaludis." Mol. Microbiol., 2007, pp. 596-609, vol. 66, No. 3.

Chen, et al., "Coevolutionary Analysis Enabled Rational Deregulation of Allosteric Enzyme Inhibition in Corynebacterium glutamicum." Appl. Env. Microbiol., 2011, pp. 42352-4360, vol. 77. No. 13.

Dodsworth, et al., "Interdomain Conjugal Transfer of DNA from Bacteria to Archaea." Appl. Environ. Microbiol., 2010, pp. 5644-5647, vol. 76, No. 16.

(Continued)

*Primary Examiner* — Suzanne M Noakes

(57) ABSTRACT

The present disclosure provides compositions and methods for using modified hydrogenotrophic microorganisms capable of biologically utilizing or converting CO and/or $CO_2$ gas, optionally in the presence of $H_2$, into methionine.

22 Claims, No Drawings

Specification includes a Sequence Listing.

(56) References Cited

OTHER PUBLICATIONS

Emery, et al., "Impact of translational selection on codon usage bias in archaeon Methanococcus maripaludis." Biol. Lett., 2011, pp. 131-135, vol. 7.
Gardner, et al., "Expression vectors for Methanococcus maripaludis: overexpression of acetohydroxyacid synthase and beta-galactosidase." Genetics, 1999, pp. 1439-1447, vol. 152, No. 4.
Goyal, et al., "A genome-scale metabolic model of Methanococcus maripaludis S2 for CO2 capture and conversion to methane." Mol Biosystems, 2014, pp. 1043-1054, vol. 10.
Graham, et al., "Methanogens with pseudomurein use diaminopimelate aminotransferase in lysine biosynthesis." FEBS Lett., 2008, pp. 1369-1374, vol. 582.
Guss, et al., "New methods for tightly regulated gene expression and highly efficient chromosomal integration of cloned genes for Methanosarcina species." Archaea, 2008, pp. 193-203, vol. 2.
Huang, et al., "Metabolic Engineering of *Escherichia coli* for Microbial Production of L-Methionine." Biotech. Bioeng., 2017, pp. 843-851, vol. 114, No. 4.
International Preliminary Report on Patentability for PCT/US2015/010068, 7 pages.
Koffas, et al., "Engineering metabolism and product formation in Corynebacterium glutamicum by coordinated gene overexpression." Metabolic Engineering, 2003, pp. 32-41, vol. 5.
Kumar, et al., "Methionine Production by Fermentation." Biotechnology Advances, 2004, pp. 41-61, vol. 23.
Leigh et al., "Model organisms for genetics in the domain Archaea: methanogens, halophiles, Thermococcales and Sulfolobales." FEMS Microbiol. Rev., 2011, pp. 577-608, vol. 35, No. 4.
Leuchtenberger et al., "Biotechnological production of amino acids and derivatives: current status and prospects." Appl. Microbiol Biotechnol., 2005, pp. 1-8, vol. 69, No. 1.
Lie, et al. "Regulatory response of Methanococcus maripaludis to alanine, an intermediate nitrogen source." J. Bacteriol., 2002, pp. 5301-5306, vol. 184, No. 19.
Liu, et al. "Cysteine is Not the Sulfur Source for Iron-Sulfur Cluster and Methionine Biosynthesis in the Methanogenic Archaeon Methanococcus maripaludis." J. Biol. Chem, 2010, pp. 31923-31929, vol. 285, No. 42.
Liu, et al. "Methanococci Use the Diaminopimelate Aminotransferase (DapL) Pathway for Lysine Biosynthesis." J. Bacteriol., 2010, pp. 3304-3310, vol. 192.
Luntz et al., "Transport and Export of L-Lysine in Corynebacterium glutamicum." J. Gen. Microbiol., 1986, pp. 2137-2146, vol. 132.
Metcalf, et al., "A genetic system for Archaea of the genus Methanosarcina: Liposome-mediated transformation and construction of shuttle vectors." Proc. Natl. Acad. Sci. U.S.A., 1997, pp. 2626-2631, vol. 94, No. 6.
Moore, et al., "Markerless mutagenesis in Methanococcus maripaludis demonstrates roles for alanine dehydrogenase, alanine racemase, and alanine permease." J. Bacteriol., 2005, pp. 972-979, vol. 187.
Naerdal, et al., "Analysis and Manipulation of Aspartate Pathway Genes for L-Lysine Overproduction from Methanol by Bacillus methanolicus." Appl. Env. Microbiol., 2011, pp. 6020-6026, vol. 77.
Park, et al., "Towards systems metabolic engineering of microorganisms for amino acid production," Curr. Opin. Biotech., 2008, pp. 454-460, vol. 19.
Patte, et al., "Regulation by methionine of the synthesis of a third aspartokinase and of a second homoserine dehydrogenase in *Escherichia coli* K 12." Biochim. Biophys Acta, 1967, pp. 245-247, vol. 136, No. 2.
Pritchett, et al., "Development of a Markerless Genetic Exchange Method for Methanosarcina acetivorans C2A and Its Use in Construction of New Genetic Tools for Methanogenic Archaea." Appl. Environ. Microbiol., 2004, pp. 1425-1433, vol. 70, No. 3.
Rauche, et al., "Novel proteins for homocysteine biosynthesis in anaerobic microorganisms." Mol. Microbiol., 2014, pp. 1330-1342, vol. 94, No. 6.
Rother, et al., "Genetic Technologies for Archaea," Curr. Opin. Microbiol., 2005, pp. 745-751, vol. 8.
Sano, et al., "Microbial Production of L-Lysine; III. Production by Mutants Resistant to S-(2-Aminoethyl)-L-Cysteine." J. Gen. Appl. Microbiol., 1970, pp. 373-391, vol. 16.
Schendel, et al. "L-Lysine Production at 50C by Mutants of a Newly Isolated and Characterized Methylotrophic *Bacillus* sp." Applied and Environmental Microbiology, 1990, pp. 963-970, vol. 56, No. 4.
Sharp, et al., "Variation in the strength of selected codon usage bias among bacteria." Nucl. Acids Res., 2005, pp. 1141-1153, vol. 33, No. 4.
Shiio, et al., "Isolation and properties oflysine-producing mutants with feedback-resistantaspartokinase derived from a Brevibacterium flavum strainwith citrate synthase and pyruvate kinase defects and feedback resistant phosphoenol pyruvate carboxylase." Agric. Biol. Chem., 1990, pp. 3275-3282, vol. 54.
Theze, et al.: "Homoserine Kinase from *Escherichia coli* K-12: Properties, Inhibition by L-Threonine, and Regulation of Biosynthesis." J. Bacteriol., 1974, pp. 577-581, vol. 118.
Tumbula, et al., "Characterization of pURB500 from the archaeon Methanococcus maripaludis and construction of a shuttle vector." J. Bacteriol., 1997, pp. 2976-2986, vol. 179.
Walters, et al., "Shuttle vector system for Methanococcus maripaludis with improved transformation efficiency." Appl. Environ. Microbiol., 2011, pp. 2549-2551, vol. 77.
Woese, et al., "Phylogenetic structure of the prokaryotic domain: The primary kingdoms." Proc. Natl. Acad. Sci. USA., 1977, pp. 5088-5090, vol. 71, No. 11.
Yoshida, et al., "Structural Insight into concerted inhibition of alpha 2 beta 2-type aspartate kinase from Corynebacterium glutamicum." J. Mol. Biol., 2007, pp. 521-536, vol. 368.
Zakataeva, et al., "The novel transmembrane *Escherichia coli* proteins involved in the amino acid efflux." FEBS Letters, 1999, pp. 228-232, vol. 452.
Allen, et al., "Homocysteine is Biosynthesized from Aspartate Semialdehyde and Hydrogen Sulfide in Methanogenic Archaea." Biochemistry, 2015, pp. 3129-3132, vol. 54, No. 20.
Hendrickson, et al., "Complete Genome Sequence of the Genetically Tractable Hydrogenotrophic Methanogen Methanococcus maripaludis." J. Bacteriol. 2004, pp. 6956-6969.
International Preliminary Report on Patentability for PCT/US2016/031318, 9 pages.
Liu, et al., "Methanogens: a window into ancient sulfur metabolism," Trends in Microbiology, 2012, pp. 251-258, vol. 20, No. 5.
Rauch, et al. "Efficient sulfide assimilation in Methanosarcine acetivorans is mediated by the MA1715 protein," Journal of Bacteriology, 2016, pp. 1974-1983, vol. 198, No. 14.
Teleki, et al., "Robust Identification of metabolic control for microbial L-methionine production following an easy-to-use puristic approach," Metabolic Engineering, 2017, pp. 159-172, vol. 41.
Willke, "Methionine production—a critical review," Applied Microbiology Biotechnology, 2014, pp. 9893-9914, vol. 98.
Gophna, "Evolutionary plasticity of methionine biosynthesis," Gene, 2005, pp. 48-57, vol. 355.
Office Action dated Dec. 4, 2017 in U.S. Appl. No. 15/109,086, 12 pages.
Examination Report dated Sep. 10, 2019 in EP 2016725977.9, 6 pages.

SEQUENCE LISTING

<160> NUMBER OF SEQ ID NOS: 32

<210> SEQ ID NO 1
<211> LENGTH: 1542
<212> TYPE: DNA
<213> ORGANISM: Archaea sp.

<400> SEQUENCE: 1

```
ttgaaaaccg ttcacgaaat taacgagaag atacgaaatg gcgatgcagt tgtagtcact     60

gcagaagaga tgatcgatat agtcgacgaa ctgggtgcag aaaaagcggc agttgaaata    120

gatgtagtta cgacaggtac atttggagca atgtgttcaa gcggagcatt tttaaatttt    180

ggacactctg atccgccaat aaaaatgtgt aaaacatatt tgaatggtgt ggaagcatat    240

tcaggaattg cagcagttga tgcttattta ggggctactc aaacgaatag tgatgatgat    300

attgatatat catatggggg ttcccacgtt cttgaagatc ttgtagctgg aaaagaaatt    360

gaacttgtag cggaaggata cactactgac tgctacccta gaaaaaaagt agaaacaacg    420

ataacaattg atgatttaaa tcaagcaatc ttagtaaatc caagaaactg ctaccaatct    480

tacaatggtg ctacgaacag tactgaagaa aaaatataca cttacatggg tgcacttctc    540

ccagaatttg gaaatttaaa ttattccggt gcaggtcaat taaatccact gcaaaacgat    600

ttcaataaag aaacaaaaac ttataacacc ttaggaatgg gtacaagaat cttcttaggc    660

ggtgcacaag gttatattgc aggttcagga acccagcaca gtccaaatgg tggatttgga    720

accttgatgg ttcaagggga cctaaaagaa atgagtacta aatatttaag aggagcaacg    780

attccaaaat acggaagtac gctttacatg ggatcggaa ttccaattcc agtattaaac     840

gcagaaattg caaaaacctg tgcaataaaa gatgaagata ttgcaatacc catattggat    900

tacggaattc caagaaggga taaacctgaa ttaggcgtta caaactataa agatgcaaga    960

tctggaaaag taacgattga agttgaaatc gaaggcaaaa aagtagataa atgcatgaga   1020

tctgcatcag tttcaagtta taaagtttca agggaaattt caaaagaact taaaaactgg   1080

atttcaaata gtgaatttat gttaacacaa agacttgaac ctttaaaaag tgcagctcca   1140

aaaccaatga aagcaaaaat gaaacttgta aaagatatat tgagcaggcc tgtagttgta   1200

ggaagcttaa atacctcaat tacacaagct tcaagagttt taattgaaaa taatataaac   1260

catctgccaa ttgtggatga aaacggcaaa ctttcaggaa taatcacttc atgggatatt   1320

gcaaaggcaa tggcgcagga taaacattca atttctgaaa tcatgactac atatatagta   1380

tctgcaacac cagatgaaac tatagatatg gcagcaagaa aaatgagcag aaacaatatt   1440

tcaggacttc ctgttgtcga ttcaaacaac aaggttcttg ggtggtttc agctgaagat   1500

atctcaaaac ttatcgggag aaatggactt cataaaattt aa                      1542
```

<210> SEQ ID NO 2
<211> LENGTH: 1542
<212> TYPE: DNA
<213> ORGANISM: Artificial Sequence
<220> FEATURE:
<223> OTHER INFORMATION: Archaea mutant sequence

<400> SEQUENCE: 2

```
ttgaaaaccg ttcacgaaat taacgagaag atacgaaatg gcgatgcagt tgtagtcact     60

gcagaagaga tgatcgatat agtcgacgaa ctgggtgcag aaaaagcggc agttgaaata    120

gatgtagtta cgacaggtac atttggagca atgtgttcaa gcggagcatt tttaaatttt    180

ggacactctg atccgccaat aaaaatgtgt aaaacatatt tgaatggtgt ggaagcatat    240
```

```
tcaggaattg cagcagttga tgcttattta ggggctactc aaacgaatag tgatgatgat    300

attgatatat catatggggg ttcccacgtt cttgaagatc ttgtagctgg aaaagaaatt    360

gaacttgtag cggaaggata cactactgac tgctacccta gaaaaaaagt agaaacaacg    420

ataacaattg atgatttaaa tcaagcaatc ttagtaaatc caagaaactg ctaccaatct    480

tacaatggtg ctacgaacag tactgaagaa aaaatataca cttacatggg tgcacttctc    540

ccagaatttg gaaatttaaa ttattccggt gcaggtcaat taaatccact gcaaaacgat    600

ttcaataaag aaacaaaaac ttataacacc ttaggaatgg gtacaagaat cttcttaggc    660

ggtgcacaag gttatattgc aggttcagga acccagcaca gtccaaatgg tggatttgga    720

accttgatgg ttcaagggga cctaaaagaa atgagtacta aatatttaag aggagcaacg    780

attccaaaat acggaagtac gctttacatg gggatcggaa ttccaattcc agtattaaac    840

gcagaaattg caaaaacctg tgcaataaaa gatgaagata ttgcaatacc catattggat    900

tacggaattc caagaaggga taaacctgaa ttaggcgtta caaactataa agatgcaaga    960

tctggaaaag taacgattga agttgaaatc gaaggcaaaa aagtagataa atgcatgaga   1020

tctgcatcag tttcaagtta taaagtttca agggaaattt caaaagaact taaaaactgg   1080

atttcaaata gtgaatttat gttaacacaa agacttgaac ctttaaaaag tgcagctcca   1140

aaaccaatga aagcaaaaat gaaacttgta aaagatatat tgagcaggcc tgtagttgta   1200

ggaagcttaa atacctcaat tacacaagct tcaagagttt taattgaaaa taatataaac   1260

catctgccaa ttgtggatga aaacggcaaa ctttcaggaa taatcacttc atggaatatt   1320

gcaaaggcaa tggcgcagga taaacattca atttctgaaa tcatgactac atatatagta   1380

tctgcaacac cagatgaaac tatagatatg gcagcaagaa aaatgagcag aaacaatatt   1440

tcaggacttc ctgttgtcga ttcaaacaac aaggttcttg ggtggtttc agctgaagat    1500

atctcaaaac ttatcgggag aaatggactt cataaaattt aa                      1542
```

<210> SEQ ID NO 3
<211> LENGTH: 513
<212> TYPE: PRT
<213> ORGANISM: Archaea sp.

<400> SEQUENCE: 3

```
Met Lys Thr Val His Glu Ile Asn Glu Lys Ile Arg Asn Gly Asp Ala
1               5                   10                  15

Val Val Val Thr Ala Glu Glu Met Ile Asp Ile Val Asp Glu Leu Gly
            20                  25                  30

Ala Glu Lys Ala Ala Val Glu Ile Asp Val Val Thr Thr Gly Thr Phe
        35                  40                  45

Gly Ala Met Cys Ser Ser Gly Ala Phe Leu Asn Phe Gly His Ser Asp
    50                  55                  60

Pro Pro Ile Lys Met Cys Lys Thr Tyr Leu Asn Gly Val Glu Ala Tyr
65                  70                  75                  80

Ser Gly Ile Ala Ala Val Asp Ala Tyr Leu Gly Ala Thr Gln Thr Asn
                85                  90                  95

Ser Asp Asp Asp Ile Asp Ile Ser Tyr Gly Gly Ser His Val Leu Glu
            100                 105                 110

Asp Leu Val Ala Gly Lys Glu Ile Glu Leu Val Ala Glu Gly Tyr Thr
        115                 120                 125

Thr Asp Cys Tyr Pro Arg Lys Lys Val Glu Thr Thr Ile Thr Ile Asp
    130                 135                 140
```

```
Asp Leu Asn Gln Ala Ile Leu Val Asn Pro Arg Asn Cys Tyr Gln Ser
145                 150                 155                 160

Tyr Asn Gly Ala Thr Asn Ser Thr Glu Glu Lys Ile Tyr Thr Tyr Met
                165                 170                 175

Gly Ala Leu Leu Pro Glu Phe Gly Asn Leu Asn Tyr Ser Gly Ala Gly
            180                 185                 190

Gln Leu Asn Pro Leu Gln Asn Asp Phe Asn Lys Glu Thr Lys Thr Tyr
        195                 200                 205

Asn Thr Leu Gly Met Gly Thr Arg Ile Phe Leu Gly Gly Ala Gln Gly
    210                 215                 220

Tyr Ile Ala Gly Ser Gly Thr Gln His Ser Pro Asn Gly Gly Phe Gly
225                 230                 235                 240

Thr Leu Met Val Gln Gly Asp Leu Lys Glu Met Ser Thr Lys Tyr Leu
                245                 250                 255

Arg Gly Ala Thr Ile Pro Lys Tyr Gly Ser Thr Leu Tyr Met Gly Ile
            260                 265                 270

Gly Ile Pro Ile Pro Val Leu Asn Ala Glu Ile Ala Lys Thr Cys Ala
        275                 280                 285

Ile Lys Asp Glu Asp Ile Ala Ile Pro Ile Leu Asp Tyr Gly Ile Pro
    290                 295                 300

Arg Arg Asp Lys Pro Glu Leu Gly Val Thr Asn Tyr Lys Asp Ala Arg
305                 310                 315                 320

Ser Gly Lys Val Thr Ile Glu Val Glu Ile Glu Gly Lys Lys Val Asp
                325                 330                 335

Lys Cys Met Arg Ser Ala Ser Val Ser Ser Tyr Lys Val Ser Arg Glu
            340                 345                 350

Ile Ser Lys Glu Leu Lys Asn Trp Ile Ser Asn Ser Glu Phe Met Leu
        355                 360                 365

Thr Gln Arg Leu Glu Pro Leu Lys Ser Ala Ala Pro Lys Pro Met Lys
    370                 375                 380

Ala Lys Met Lys Leu Val Lys Asp Ile Leu Ser Arg Pro Val Val Val
385                 390                 395                 400

Gly Ser Leu Asn Thr Ser Ile Thr Gln Ala Ser Arg Val Leu Ile Glu
                405                 410                 415

Asn Asn Ile Asn His Leu Pro Ile Val Asp Glu Asn Gly Lys Leu Ser
            420                 425                 430

Gly Ile Ile Thr Ser Trp Asp Ile Ala Lys Ala Met Ala Gln Asp Lys
        435                 440                 445

His Ser Ile Ser Glu Ile Met Thr Thr Tyr Ile Val Ser Ala Thr Pro
    450                 455                 460

Asp Glu Thr Ile Asp Met Ala Ala Arg Lys Met Ser Arg Asn Asn Ile
465                 470                 475                 480

Ser Gly Leu Pro Val Val Asp Ser Asn Asn Lys Val Leu Gly Val Val
                485                 490                 495

Ser Ala Glu Asp Ile Ser Lys Leu Ile Gly Arg Asn Gly Leu His Lys
            500                 505                 510

Ile
```

```
<210> SEQ ID NO 4
<211> LENGTH: 513
<212> TYPE: PRT
<213> ORGANISM: Artificial Sequence
<220> FEATURE:
<223> OTHER INFORMATION: Archaea mutant sequence
```

<400> SEQUENCE: 4

```
Met Lys Thr Val His Glu Ile Asn Glu Lys Ile Arg Asn Gly Asp Ala
1               5                   10                  15

Val Val Val Thr Ala Glu Glu Met Ile Asp Ile Val Asp Glu Leu Gly
            20                  25                  30

Ala Glu Lys Ala Ala Val Glu Ile Asp Val Val Thr Thr Gly Thr Phe
        35                  40                  45

Gly Ala Met Cys Ser Ser Gly Ala Phe Leu Asn Phe Gly His Ser Asp
    50                  55                  60

Pro Pro Ile Lys Met Cys Lys Thr Tyr Leu Asn Gly Val Glu Ala Tyr
65                  70                  75                  80

Ser Gly Ile Ala Ala Val Asp Ala Tyr Leu Gly Ala Thr Gln Thr Asn
                85                  90                  95

Ser Asp Asp Asp Ile Asp Ile Ser Tyr Gly Gly Ser His Val Leu Glu
            100                 105                 110

Asp Leu Val Ala Gly Lys Glu Ile Glu Leu Val Ala Glu Gly Tyr Thr
        115                 120                 125

Thr Asp Cys Tyr Pro Arg Lys Lys Val Glu Thr Thr Ile Thr Ile Asp
    130                 135                 140

Asp Leu Asn Gln Ala Ile Leu Val Asn Pro Arg Asn Cys Tyr Gln Ser
145                 150                 155                 160

Tyr Asn Gly Ala Thr Asn Ser Thr Glu Glu Lys Ile Tyr Thr Tyr Met
                165                 170                 175

Gly Ala Leu Leu Pro Glu Phe Gly Asn Leu Asn Tyr Ser Gly Ala Gly
            180                 185                 190

Gln Leu Asn Pro Leu Gln Asn Asp Phe Asn Lys Glu Thr Lys Thr Tyr
        195                 200                 205

Asn Thr Leu Gly Met Gly Thr Arg Ile Phe Leu Gly Gly Ala Gln Gly
    210                 215                 220

Tyr Ile Ala Gly Ser Gly Thr Gln His Ser Pro Asn Gly Gly Phe Gly
225                 230                 235                 240

Thr Leu Met Val Gln Gly Asp Leu Lys Glu Met Ser Thr Lys Tyr Leu
                245                 250                 255

Arg Gly Ala Thr Ile Pro Lys Tyr Gly Ser Thr Leu Tyr Met Gly Ile
            260                 265                 270

Gly Ile Pro Ile Pro Val Leu Asn Ala Glu Ile Ala Lys Thr Cys Ala
        275                 280                 285

Ile Lys Asp Glu Asp Ile Ala Ile Pro Ile Leu Asp Tyr Gly Ile Pro
    290                 295                 300

Arg Arg Asp Lys Pro Glu Leu Gly Val Thr Asn Tyr Lys Asp Ala Arg
305                 310                 315                 320

Ser Gly Lys Val Thr Ile Glu Val Glu Ile Glu Gly Lys Lys Val Asp
                325                 330                 335

Lys Cys Met Arg Ser Ala Ser Val Ser Ser Tyr Lys Val Ser Arg Glu
            340                 345                 350

Ile Ser Lys Glu Leu Lys Asn Trp Ile Ser Asn Ser Glu Phe Met Leu
        355                 360                 365

Thr Gln Arg Leu Glu Pro Leu Lys Ser Ala Ala Pro Lys Pro Met Lys
    370                 375                 380

Ala Lys Met Lys Leu Val Lys Asp Ile Leu Ser Arg Pro Val Val Val
385                 390                 395                 400

Gly Ser Leu Asn Thr Ser Ile Thr Gln Ala Ser Arg Val Leu Ile Glu
```

```
                405                 410                 415

Asn Asn Ile Asn His Leu Pro Ile Val Asp Glu Asn Gly Lys Leu Ser
            420                 425                 430

Gly Ile Ile Thr Ser Trp Asn Ile Ala Lys Ala Met Ala Gln Asp Lys
        435                 440                 445

His Ser Ile Ser Glu Ile Met Thr Thr Tyr Ile Val Ser Ala Thr Pro
    450                 455                 460

Asp Glu Thr Ile Asp Met Ala Ala Arg Lys Met Ser Arg Asn Asn Ile
465                 470                 475                 480

Ser Gly Leu Pro Val Val Asp Ser Asn Asn Lys Val Leu Gly Val Val
                485                 490                 495

Ser Ala Glu Asp Ile Ser Lys Leu Ile Gly Arg Asn Gly Leu His Lys
            500                 505                 510

Ile


<210> SEQ ID NO 5
<211> LENGTH: 399
<212> TYPE: DNA
<213> ORGANISM: Archaea sp.

<400> SEQUENCE: 5

gtgaaaaaga gagtatttta ctggatatct ggaagcaacg taagagaacc ggtagtttca      60

aacgtggttt tagaaactgg tgtaatggta aatattttaa aggcaaaaat ggagccaagg     120

gaaggatttt taattctcga attaactggc gatgaagaac agatcgaaaa atcaattgaa     180

atactgaaaa aattcgggga agcagaagat atcccaaaaa tcatccaaaa agatgatgaa     240

aaatgcatcg attgtggtgc atgtgtcgtt cactgccccg ttggtgcgct ttcagttgac     300

gaagaattta aaatactgct cgacgaagac gaatgcattg gatgtaaaaa ctgtgcaaaa     360

atatgccctg taaatgcaat taaaatattt gaaatctaa                            399


<210> SEQ ID NO 6
<211> LENGTH: 399
<212> TYPE: DNA
<213> ORGANISM: Artificial Sequence
<220> FEATURE:
<223> OTHER INFORMATION: Archaea mutant sequence

<400> SEQUENCE: 6

gtgaaaaaga gagtatttta ctggatatct ggaagcaacg taagagaacc ggtagtttca      60

aacgtggttt tagaaactgg tgtaatggta aatattttaa aggcaaaaat ggagccaagg     120

gaaggatttt taattctcga attaactggc gatgaagaac agatcgaaaa atcaattgaa     180

atactgaaaa aattcgggga agcagaagat atcccaaaaa tcatccaaaa agatgatgaa     240

aaatgcatcg attgtggtgc atgtgtcgtt cactgccccg ttggtgcgct ttcagttgac     300

gaagaattta aaatactgct cgacgaagac gaatgcattg aatgtaaaaa ctgtgcaaaa     360

atatgccctg taaatgcaat taaaatattt gaaatctaa                            399


<210> SEQ ID NO 7
<211> LENGTH: 132
<212> TYPE: PRT
<213> ORGANISM: Archaea sp.

<400> SEQUENCE: 7

Met Lys Lys Arg Val Phe Tyr Trp Ile Ser Gly Ser Asn Val Arg Glu
1               5                   10                  15
```

```
Pro Val Val Ser Asn Val Val Leu Glu Thr Gly Val Met Val Asn Ile
            20                  25                  30

Leu Lys Ala Lys Met Glu Pro Arg Glu Gly Phe Leu Ile Leu Glu Leu
        35                  40                  45

Thr Gly Asp Glu Glu Gln Ile Glu Lys Ser Ile Glu Ile Leu Lys Lys
    50                  55                  60

Phe Gly Glu Ala Glu Asp Ile Pro Lys Ile Ile Gln Lys Asp Asp Glu
65                  70                  75                  80

Lys Cys Ile Asp Cys Gly Ala Cys Val Val His Cys Pro Val Gly Ala
                85                  90                  95

Leu Ser Val Asp Glu Glu Phe Lys Ile Leu Leu Asp Glu Asp Glu Cys
            100                 105                 110

Ile Gly Cys Lys Asn Cys Ala Lys Ile Cys Pro Val Asn Ala Ile Lys
        115                 120                 125

Ile Phe Glu Ile
    130


<210> SEQ ID NO 8
<211> LENGTH: 132
<212> TYPE: PRT
<213> ORGANISM: Artificial Sequence
<220> FEATURE:
<223> OTHER INFORMATION: Archaea mutant sequence

<400> SEQUENCE: 8

Met Lys Lys Arg Val Phe Tyr Trp Ile Ser Gly Ser Asn Val Arg Glu
1               5                   10                  15

Pro Val Val Ser Asn Val Val Leu Glu Thr Gly Val Met Val Asn Ile
            20                  25                  30

Leu Lys Ala Lys Met Glu Pro Arg Glu Gly Phe Leu Ile Leu Glu Leu
        35                  40                  45

Thr Gly Asp Glu Glu Gln Ile Glu Lys Ser Ile Glu Ile Leu Lys Lys
    50                  55                  60

Phe Gly Glu Ala Glu Asp Ile Pro Lys Ile Ile Gln Lys Asp Asp Glu
65                  70                  75                  80

Lys Cys Ile Asp Cys Gly Ala Cys Val Val His Cys Pro Val Gly Ala
                85                  90                  95

Leu Ser Val Asp Glu Glu Phe Lys Ile Leu Leu Asp Glu Asp Glu Cys
            100                 105                 110

Ile Glu Cys Lys Asn Cys Ala Lys Ile Cys Pro Val Asn Ala Ile Lys
        115                 120                 125

Ile Phe Glu Ile
    130


<210> SEQ ID NO 9
<211> LENGTH: 19
<212> TYPE: DNA
<213> ORGANISM: Artificial Sequence
<220> FEATURE:
<223> OTHER INFORMATION: Primer sequence

<400> SEQUENCE: 9

ctatagaact aacccaatg                                                  19


<210> SEQ ID NO 10
<211> LENGTH: 17
<212> TYPE: DNA
<213> ORGANISM: Artificial Sequence
<220> FEATURE:
```

<223> OTHER INFORMATION: Primer sequence

<400> SEQUENCE: 10
ggtgttgcag atactat 17

<210> SEQ ID NO 11
<211> LENGTH: 15
<212> TYPE: DNA
<213> ORGANISM: Artificial Sequence
<220> FEATURE:
<223> OTHER INFORMATION: Primer sequence

<400> SEQUENCE: 11
agacttgaac cttta 15

<210> SEQ ID NO 12
<211> LENGTH: 18
<212> TYPE: DNA
<213> ORGANISM: Artificial Sequence
<220> FEATURE:
<223> OTHER INFORMATION: Primer sequence

<400> SEQUENCE: 12
cgccaaaatc ttccctgc 18

<210> SEQ ID NO 13
<211> LENGTH: 19
<212> TYPE: DNA
<213> ORGANISM: Artificial Sequence
<220> FEATURE:
<223> OTHER INFORMATION: Forward Primer sequence

<400> SEQUENCE: 13
gggacggcgc aacaaatgg 19

<210> SEQ ID NO 14
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 14
ggagatagtg agacccctgg agt 23

<210> SEQ ID NO 15
<211> LENGTH: 23
<212> TYPE: DNA
<213> ORGANISM: Artificial Sequence
<220> FEATURE:
<223> OTHER INFORMATION: Primer sequence

<400> SEQUENCE: 15
aatagttacc ggcgttacaa tca 23

<210> SEQ ID NO 16
<211> LENGTH: 24
<212> TYPE: DNA
<213> ORGANISM: Artificial Sequence
<220> FEATURE:
<223> OTHER INFORMATION: Primer sequence

<400> SEQUENCE: 16
tccctgatcg atagaaagtg tagt 24

<210> SEQ ID NO 17
<211> LENGTH: 23
<212> TYPE: DNA
<213> ORGANISM: Artificial Sequence
<220> FEATURE:
<223> OTHER INFORMATION: Primer sequence

<400> SEQUENCE: 17
ttgccgatga aattaaagtg aaa 23

<210> SEQ ID NO 18
<211> LENGTH: 34
<212> TYPE: DNA
<213> ORGANISM: Artificial Sequence
<220> FEATURE:
<223> OTHER INFORMATION: Primer sequence

<400> SEQUENCE: 18
gcgggcgcgc cgcataatta caccttatgc gttc 34

<210> SEQ ID NO 19
<211> LENGTH: 33
<212> TYPE: DNA
<213> ORGANISM: Artificial Sequence
<220> FEATURE:
<223> OTHER INFORMATION: Primer sequence

<400> SEQUENCE: 19
gcgggcgcgc ctaatcacgg ttcgtgatac tat 33

<210> SEQ ID NO 20
<211> LENGTH: 40
<212> TYPE: DNA
<213> ORGANISM: Artificial Sequence
<220> FEATURE:
<223> OTHER INFORMATION: Primer sequence

<400> SEQUENCE: 20
attacgccaa gcttggtacc actctcttct tcttcaggga 40

<210> SEQ ID NO 21
<211> LENGTH: 40
<212> TYPE: DNA
<213> ORGANISM: Artificial Sequence
<220> FEATURE:
<223> OTHER INFORMATION: Primer sequence

<400> SEQUENCE: 21
gtggatccga gctcggtacc tgagatcccc gcgctggagg 40

<210> SEQ ID NO 22
<211> LENGTH: 18
<212> TYPE: DNA
<213> ORGANISM: Artificial Sequence
<220> FEATURE:
<223> OTHER INFORMATION: Primer sequence

<400> SEQUENCE: 22
gtattgaatt ggcaaact 18

<210> SEQ ID NO 23
<211> LENGTH: 18
<212> TYPE: DNA
<213> ORGANISM: Artificial Sequence
<220> FEATURE:
<223> OTHER INFORMATION: Primer sequence

<400> SEQUENCE: 23
accggctcag acccggtg 18

<210> SEQ ID NO 24
<211> LENGTH: 18
<212> TYPE: DNA
<213> ORGANISM: Artificial Sequence
<220> FEATURE:
<223> OTHER INFORMATION: Primer sequence

<400> SEQUENCE: 24
ggaaagaact cgacgtgc 18

<210> SEQ ID NO 25
<211> LENGTH: 19
<212> TYPE: DNA
<213> ORGANISM: Artificial Sequence
<220> FEATURE:
<223> OTHER INFORMATION: Primer sequence

<400> SEQUENCE: 25
actgacattc ttgattatg 19

<210> SEQ ID NO 26
<211> LENGTH: 17
<212> TYPE: DNA
<213> ORGANISM: Artificial Sequence
<220> FEATURE:
<223> OTHER INFORMATION: Primer sequence

<400> SEQUENCE: 26
cttgcagcgc gcaggct 17

<210> SEQ ID NO 27
<211> LENGTH: 36
<212> TYPE: DNA
<213> ORGANISM: Artificial Sequence
<220> FEATURE:
<223> OTHER INFORMATION: Primer sequence

<400> SEQUENCE: 27
aaattatgag gcgcgcctcc ctgaagaaga agagag 36

<210> SEQ ID NO 28
<211> LENGTH: 34
<212> TYPE: DNA
<213> ORGANISM: Artificial Sequence
<220> FEATURE:
<223> OTHER INFORMATION: Primer sequence

<400> SEQUENCE: 28
tgcttattcg gcgcgccagt tccattttac cacc 34

<210> SEQ ID NO 29
<211> LENGTH: 1503
<212> TYPE: DNA
<213> ORGANISM: Archaea sp.

<400> SEQUENCE: 29
atggttgaaa aatcggttca tgagatcaat aaaaaaattg aagatggaag cgtcaatgta 60
gtcacagccg aggaaatggt cggaattgtt gaaaaccttg gcgtggaagg tgctgcaaga 120
gaagttgatg tggtcactac aggcacgttc ggagccatgt gctcttcagg tttgatgctt 180
aatctcggac attccgaacc cccgatcaag atccagaaac tctggtttaa caacgtggag 240

```
gcatacagcg ggcttgctgc tgtggatgct tatctggggg ctgcccagat atcggataca    300

agaggaatac agtatggtgg agcgcacgtt attgaagacc tgctgagagg gaaagaactc    360

gacgtgcatg caacttccta tgggacagac tgctatccca ggaaagtgct tgatacgaga    420

attaccctcg atgacttaaa cgaggcagtc cttctcaacc ccagaaacgc ttaccagaaa    480

tatgccgctg caacaaacag ttcaaaaagg attctgaaca cctatatggg agagcttcta    540

cccaatttcg gaaacgtaac ttattccggg gcaggagtgc tttctcccct ttcaaatgat    600

cctgactacg aaactatcgg gatgggcaca aggattttca tgggaggagc ccagggctat    660

attataggca atgggaccca gcattctccc tcaagcagtt ttgggaccct tatgcttaaa    720

ggaaacctga aagaaatgag ctccgattat ttaagggctg cttcttttgc aggctacgga    780

acaactcttt acatgggaat cggaatcccc atacccattc tgaatgaaaa aatcgcagcc    840

tcaactgcgg tgcgtgatga agacattttt actgacattc ttgattatgc cgtgggcagc    900

agggataagc ctgtgataaa gcaggtaaac tatgccgagc tcaggtcagg ctcgatagag    960

cttgaaggga agaacacacc gacctcatcc ctctcaagtt tcaagaacgc cagaaagatt   1020

gcaaatgagc taaaggaatg ggttaagcac ggaaaattct ttgtcagcat gcccgtagaa   1080

aagctttccc gcgagggctc ggcaaagtcc atgaaacaga ctcaggcagt cccactcgta   1140

aaagacgtca tggcagactt tattgttacg atcaaaaaga accagacggt tcaggacgct   1200

gcaaagaaga tctgggaaaa ctcttttaac caccttgctg tggtttcgga tacaggggaa   1260

ctggtaggaa tcctgacggc ctgggatatc tcaaaagccg ttgccgaaaa tatatttgat   1320

tccgtagaaa gtgtcatgac gaaaaaagtc cttacctgcg ccccgaacga acccgtggac   1380

cttgcagcgc gcaggcttga ccgctatggc gtttcggcaa tgcctgtaat cgatacacag   1440

agaaaagtac tcggaataat tacgagcgac aatataagca agcttctcgc aaggaggtac   1500

tga                                                                 1503
```

<210> SEQ ID NO 30
<211> LENGTH: 500
<212> TYPE: PRT
<213> ORGANISM: Archaea sp.

<400> SEQUENCE: 30

```
Met Val Glu Lys Ser Val His Glu Ile Asn Lys Lys Ile Glu Asp Gly
1               5                   10                  15

Ser Val Asn Val Val Thr Ala Glu Glu Met Val Gly Ile Val Glu Asn
            20                  25                  30

Leu Gly Val Glu Gly Ala Ala Arg Glu Val Asp Val Val Thr Thr Gly
        35                  40                  45

Thr Phe Gly Ala Met Cys Ser Ser Gly Leu Met Leu Asn Leu Gly His
    50                  55                  60

Ser Glu Pro Pro Ile Lys Ile Gln Lys Leu Trp Phe Asn Asn Val Glu
65                  70                  75                  80

Ala Tyr Ser Gly Leu Ala Ala Val Asp Ala Tyr Leu Gly Ala Ala Gln
                85                  90                  95

Ile Ser Asp Thr Arg Gly Ile Gln Tyr Gly Gly Ala His Val Ile Glu
            100                 105                 110

Asp Leu Leu Arg Gly Lys Glu Leu Asp Val His Ala Thr Ser Tyr Gly
        115                 120                 125

Thr Asp Cys Tyr Pro Arg Lys Val Leu Asp Thr Arg Ile Thr Leu Asp
    130                 135                 140
```

```
Asp Leu Asn Glu Ala Val Leu Leu Asn Pro Arg Asn Ala Tyr Gln Lys
145                 150                 155                 160

Tyr Ala Ala Ala Thr Asn Ser Ser Lys Arg Ile Leu Asn Thr Tyr Met
                165                 170                 175

Gly Glu Leu Leu Pro Asn Phe Gly Asn Val Thr Tyr Ser Gly Ala Gly
            180                 185                 190

Val Leu Ser Pro Leu Ser Asn Asp Pro Asp Tyr Glu Thr Ile Gly Met
        195                 200                 205

Gly Thr Arg Ile Phe Met Gly Gly Ala Gln Gly Tyr Ile Ile Gly Asn
    210                 215                 220

Gly Thr Gln His Ser Pro Ser Ser Ser Phe Gly Thr Leu Met Leu Lys
225                 230                 235                 240

Gly Asn Leu Lys Glu Met Ser Ser Asp Tyr Leu Arg Ala Ala Ser Phe
                245                 250                 255

Ala Gly Tyr Gly Thr Thr Leu Tyr Met Gly Ile Gly Ile Pro Ile Pro
            260                 265                 270

Ile Leu Asn Glu Lys Ile Ala Ala Ser Thr Ala Val Arg Asp Glu Asp
        275                 280                 285

Ile Phe Thr Asp Ile Leu Asp Tyr Ala Val Gly Ser Arg Asp Lys Pro
    290                 295                 300

Val Ile Lys Gln Val Asn Tyr Ala Glu Leu Arg Ser Gly Ser Ile Glu
305                 310                 315                 320

Leu Glu Gly Lys Asn Thr Pro Thr Ser Ser Leu Ser Ser Phe Lys Asn
                325                 330                 335

Ala Arg Lys Ile Ala Asn Glu Leu Lys Glu Trp Val Lys His Gly Lys
            340                 345                 350

Phe Phe Val Ser Met Pro Val Glu Lys Leu Ser Arg Glu Gly Ser Ala
        355                 360                 365

Lys Ser Met Lys Gln Thr Gln Ala Val Pro Leu Val Lys Asp Val Met
    370                 375                 380

Ala Asp Phe Ile Val Thr Ile Lys Lys Asn Gln Thr Val Gln Asp Ala
385                 390                 395                 400

Ala Lys Lys Ile Trp Glu Asn Ser Phe Asn His Leu Ala Val Val Ser
                405                 410                 415

Asp Thr Gly Glu Leu Val Gly Ile Leu Thr Ala Trp Asp Ile Ser Lys
            420                 425                 430

Ala Val Ala Glu Asn Ile Phe Asp Ser Val Glu Ser Val Met Thr Lys
        435                 440                 445

Lys Val Leu Thr Cys Ala Pro Asn Glu Pro Val Asp Leu Ala Ala Arg
    450                 455                 460

Arg Leu Asp Arg Tyr Gly Val Ser Ala Met Pro Val Ile Asp Thr Gln
465                 470                 475                 480

Arg Lys Val Leu Gly Ile Ile Thr Ser Asp Asn Ile Ser Lys Leu Leu
                485                 490                 495

Ala Arg Arg Tyr
            500
```

<210> SEQ ID NO 31
<211> LENGTH: 1503
<212> TYPE: DNA
<213> ORGANISM: Artificial Sequence
<220> FEATURE:
<223> OTHER INFORMATION: Archaea mutant sequence

<400> SEQUENCE: 31

```
atggttgaaa aatcggttca tgagatcaat aaaaaaattg aagatggaag cgtcaatgta      60
gtcacagccg aggaaatggt cggaattgtt gaaaaccttg gcgtggaagg tgctgcaaga     120
gaagttgatg tggtcactac aggcacgttc ggagccatgt gctcttcagg tttgatgctt     180
aatctcggac attccgaacc cccgatcaag atccagaaac tctggtttaa caacgtggag     240
gcatacagcg ggcttgctgc tgtggatgct tatctggggg ctgcccagat atcggataca     300
agaggaatac agtatggtgg agcgcacgtt attgaagacc tgctgagagg gaaagaactc     360
gacgtgcatg caacttccta tgggacagac tgctatccca ggaaagtgct tgatacgaga     420
attaccctcg atgacttaaa cgaggcagtc cttctcaacc ccagaaacgc ttaccagaaa     480
tatgccgctg caacaaacag ttcaaaaagg attctgaaca cctatatggg agagcttcta     540
cccaatttcg gaaacgtaac ttattccggg gcaggagtgc tttctcccct ttcaaatgat     600
cctgactacg aaactatcgg gatgggcaca aggattttca tgggaggagc ccagggctat     660
attataggca atgggaccca gcattctccc tcaagcagtt ttgggaccct tatgcttaaa     720
ggaaacctga aagaaatgag ctccgattat ttaagggctg cttcttttgc aggctacgga     780
acaactcttt acatgggaat cggaatcccc atacccattc tgaatgaaaa aatcgcagcc     840
tcaactgcgg tgcgtgatga agacattttt actgacattc ttgattatgc cgtgggcagc     900
agggataagc ctgtgataaa gcaggtaaac tatgccgagc tcaggtcagg ctcgatagag     960
cttgaaggga agaacacacc gacctcatcc ctctcaagtt tcaagaacgc cagaaagatt    1020
gcaaatgagc taaaggaatg ggttaagcac ggaaaattct ttgtcagcat gcccgtagaa    1080
aagctttccc gcgagggctc ggcaaagtcc atgaaacaga ctcaggcagt cccactcgta    1140
aaagacgtca tggcagactt tattgttacg atcaaaaaga accagacggt tcaggacgct    1200
gcaaagaaga tctgggaaaa ctcttttaac caccttgctg tggtttcgga tacaggggaa    1260
ctggtaggaa tcctgacggc ctgggatatc tcaaaagccg ttgccgaaaa tatatttgat    1320
tccgtagaaa gtgtcatgac gaaaaaagtc cttacctgcg ccccgaacga acccgtggac    1380
cttgcagcgc gcaggcttga ccgctatggc gtttcggcaa tgcctgtaat cgatacacag    1440
agaaaagtac tcggaataat tacgaacgac aatataagca agcttctcgc aaggaggtac    1500
tga                                                                  1503
```

<210> SEQ ID NO 32
<211> LENGTH: 500
<212> TYPE: PRT
<213> ORGANISM: Artificial Sequence
<220> FEATURE:
<223> OTHER INFORMATION: Archaea mutant sequence

<400> SEQUENCE: 32

```
Met Val Glu Lys Ser Val His Glu Ile Asn Lys Lys Ile Glu Asp Gly
1               5                   10                  15

Ser Val Asn Val Val Thr Ala Glu Glu Met Val Gly Ile Val Glu Asn
            20                  25                  30

Leu Gly Val Glu Gly Ala Ala Arg Glu Val Asp Val Val Thr Thr Gly
        35                  40                  45

Thr Phe Gly Ala Met Cys Ser Ser Gly Leu Met Leu Asn Leu Gly His
    50                  55                  60

Ser Glu Pro Pro Ile Lys Ile Gln Lys Leu Trp Phe Asn Asn Val Glu
65                  70                  75                  80

Ala Tyr Ser Gly Leu Ala Ala Val Asp Ala Tyr Leu Gly Ala Ala Gln
```

```
                85                  90                  95

Ile Ser Asp Thr Arg Gly Ile Gln Tyr Gly Gly Ala His Val Ile Glu
            100                 105                 110

Asp Leu Leu Arg Gly Lys Glu Leu Asp Val His Ala Thr Ser Tyr Gly
        115                 120                 125

Thr Asp Cys Tyr Pro Arg Lys Val Leu Asp Thr Arg Ile Thr Leu Asp
    130                 135                 140

Asp Leu Asn Glu Ala Val Leu Leu Asn Pro Arg Asn Ala Tyr Gln Lys
145                 150                 155                 160

Tyr Ala Ala Ala Thr Asn Ser Ser Lys Arg Ile Leu Asn Thr Tyr Met
                165                 170                 175

Gly Glu Leu Leu Pro Asn Phe Gly Asn Val Thr Tyr Ser Gly Ala Gly
            180                 185                 190

Val Leu Ser Pro Leu Ser Asn Asp Pro Asp Tyr Glu Thr Ile Gly Met
        195                 200                 205

Gly Thr Arg Ile Phe Met Gly Gly Ala Gln Gly Tyr Ile Ile Gly Asn
    210                 215                 220

Gly Thr Gln His Ser Pro Ser Ser Ser Phe Gly Thr Leu Met Leu Lys
225                 230                 235                 240

Gly Asn Leu Lys Glu Met Ser Ser Asp Tyr Leu Arg Ala Ala Ser Phe
                245                 250                 255

Ala Gly Tyr Gly Thr Thr Leu Tyr Met Gly Ile Gly Ile Pro Ile Pro
            260                 265                 270

Ile Leu Asn Glu Lys Ile Ala Ala Ser Thr Ala Val Arg Asp Glu Asp
        275                 280                 285

Ile Phe Thr Asp Ile Leu Asp Tyr Ala Val Gly Ser Arg Asp Lys Pro
    290                 295                 300

Val Ile Lys Gln Val Asn Tyr Ala Glu Leu Arg Ser Gly Ser Ile Glu
305                 310                 315                 320

Leu Glu Gly Lys Asn Thr Pro Thr Ser Ser Leu Ser Ser Phe Lys Asn
                325                 330                 335

Ala Arg Lys Ile Ala Asn Glu Leu Lys Glu Trp Val Lys His Gly Lys
            340                 345                 350

Phe Phe Val Ser Met Pro Val Glu Lys Leu Ser Arg Glu Gly Ser Ala
        355                 360                 365

Lys Ser Met Lys Gln Thr Gln Ala Val Pro Leu Val Lys Asp Val Met
    370                 375                 380

Ala Asp Phe Ile Val Thr Ile Lys Lys Asn Gln Thr Val Gln Asp Ala
385                 390                 395                 400

Ala Lys Lys Ile Trp Glu Asn Ser Phe Asn His Leu Ala Val Val Ser
                405                 410                 415

Asp Thr Gly Glu Leu Val Gly Ile Leu Thr Ala Trp Asp Ile Ser Lys
            420                 425                 430

Ala Val Ala Glu Asn Ile Phe Asp Ser Val Glu Ser Val Met Thr Lys
        435                 440                 445

Lys Val Leu Thr Cys Ala Pro Asn Glu Pro Val Asp Leu Ala Ala Arg
    450                 455                 460

Arg Leu Asp Arg Tyr Gly Val Ser Ala Met Pro Val Ile Asp Thr Gln
465                 470                 475                 480
```

-continued

```
Arg Lys Val Leu Gly Ile Ile Thr Asn Asp Asn Ile Ser Lys Leu Leu
                485                 490                 495

Ala Arg Arg Tyr
            500
```

COMPOSITIONS AND METHODS FOR BIOLOGICAL PRODUCTION OF METHIONINE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 910215_407WO_SEQUENCE_LISTING.txt. The text file is 30.5 KB, was created on May 6, 2016, and is being submitted electronically via EFS-Web.

BACKGROUND

Methionine is a sulfur-containing, essential amino acid, which is utilized in a variety of applications in the food and medical industries. For example, methionine is used as an additive in animal feed and foods and as an ingredient in many medicines. Accordingly, there is a high industrial demand for methionine.

To meet the high demand, methionine has been manufactured synthetically via a complex chemical synthesis involving hard-to-handle raw materials such as methyl mercaptan, propylene and hydrogen cyanide. The synthetic production of methionine requires harsh production environments or results in environmentally detrimental byproducts.

Due to the high cost of the starting materials and the environmental impact of synthetic production, a method of producing methionine by fermentation would be preferred. However, efficient fermentative production of methionine has been complicated by the presence of the sulfur atom in methionine. In addition, current fermentation methods utilize sugars and carbohydrates as a starting carbon source. The use of carbohydrates is complicated by finding reliable source material for year-round production and environmental concerns. As an example, many carbohydrate waste sources (e.g., residual crop biomass) can be fermented, but are seasonal. Alternately, some crops can be grown to produce carbohydrates for industrial fermentation reaction. However, these methods reduce the available arable land for food production and are expensive.

Given the high demand for methionine and the relative high cost and unreliability of fermentable carbohydrates, there is a need in the art for alternative and improved methods for biologically producing methionine in a cost-effective manner. The present disclosure meets such needs, and further provides other related advantages.

DETAILED DESCRIPTION

The present disclosure provides compositions and methods for metabolic engineering (e.g., altering genes, gene expression, gene expression regulation) of hydrogenotrophic microorganisms to produce higher levels of methionine as compared to a wild-type or parent organism.

By way of background, many microorganisms, including those classified as Archaea and hydrogenotrophic microorganisms, produce methionine via biosynthetic pathways that share several enzymes that are involved in the production of other amino acids, such as the aspartate pathway amino acids. One or more of these amino acid biosynthesis enzymes are subject to feedback regulation, repression of gene expression, or both. For example, aspartokinase, the first committed enzyme involved in directing carbon flux into the biosynthesis of industrially important amino acids (e.g., methionine), is allosterically inhibited from phosphorylating aspartate by threonine and lysine in *Corynebacterium glutamicum* (Sano and Shiio, *J. Gen. Appl. Microbiol.* 16:373, 1970; Yoshida et al., *J. Mol. Biol.* 368:521, 2007). Another enzyme, homoserine O-succinyltransferase is subject to feedback regulation by methionine and S-adenosylmethionine (Born and Blanchard, *Biochem.* 38:14416, 1999). Homoserine dehydrogenase is the first committed enzyme in the methionine/threonine biosynthetic pathways, but it has to compete for aspartyl semialdehyde with the first enzyme committed to the lysine biosynthetic pathway, dihydrodipicolinate synthase. Hence, whether carbon flux goes toward methionine or lysine will depend on which enzyme obtains the substrate.

The present disclosure relates to the surprising discovery that hydrogenotrophic microorganisms having one or more altered sulfur assimilation-associated open reading frames (ORFs), referred to herein as MMP1359 and MMP1358, can overproduce methionine compared to a wild-type (parent) hydrogenotrophic microorganism (e.g., methanogen). By way of further background, Rauch et al. (*Mol. Microbiol.* 94:1330, 2014) found by dual knockout mutations of *Methanosarcina acetivorans* ORFs called MA1821 and MA1822 ORFs (which are homologs of the MMP1359 and MMP1358 ORFs, respectively) are involved in homocysteine biosynthesis in a genetic background lacking O-acetylhomoserine sulfhydrylase activity for homocysteine formation; in particular, these ORFs identified by bioinformatics techniques appear to be involved in a process of incorporating sulfide into homocysteine in anaerobes. Although Rauch et al. (2014) found that the MA1821 and MA1822 ORFs colocalized on the genome with methionine biosynthesis (which not uncommon for genes involved in homocysteine biosynthesis), a role for these ORFs in methionine biosynthesis was not explored. While not wishing to be bound by theory, it is believed that the present disclosure demonstrates that MMP1359 and MMP1358 ORFs are subject to feedback inhibition by methionine or S-adenosylmethionine and that the altered ORFs of the instant disclosure encode polypeptides resistant to methionine feedback inhibition. Accordingly, in certain aspects, the present disclosure provides compositions and methods for using modified hydrogenotrophic microorganisms (e.g., Archaea) that express deregulated or genetically modified MMP1359, MMP1358, or both, to facilitate metabolism of a gas feedstock (e.g., a gas comprising hydrogen and a carbon oxide, such as CO, $CO_2$) to produce methionine at a higher level than a parent hydrogenotrophic microorganism.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, "aspartate pathway amino acids" or "aspartate family of amino acids" refers to one or more amino acids synthesized from aspartate, including lysine, threonine, and methionine. While steps in the biosynthetic pathways for each of the aspartate family of amino acids branch and diverge, they all begin with the phosphorylation of aspartate by an aspartate kinase (also referred to as an aspartokinase). In certain embodiments, an aspartate kinase in the biosynthetic pathway of the aspartate family of amino acids is subject to feedback inhibition by one or more of lysine, threonine, and methionine.

As used herein, "methionine biosynthetic pathway" or "methionine pathway" refers to one or more enzymes that are involved directly or indirectly in the biosynthesis of methionine and precursor metabolites (e.g., cysteine, homoserine) that are used in the biosynthesis of methionine. Exemplary enzymes that may comprise a methionine biosynthetic pathway include aspartokinase, aspartate semialdehyde dehydrogenase, homoserine dehydrogenase, homoserine O-acetyltransferase, homoserine O-transsuccinyltransferase, O-succinylhomoserine lyase, cystathionine γ-synthase, cystathionine β-lyase, O-acetylhomoserine sulfhydrylase, homocysteine S-methyltransferase, methionine synthase (cobalamin dependent or independent), MMP1358, MMP1359, or any combination thereof.

As used herein, a "$H_2/CO_x$ substrate" or "$H_2/CO_x$ feedstock" refers to a mixture of hydrogen ($H_2$) with carbon dioxide ($CO_2$) or carbon monoxide (CO) or both, which may also include various other components, such as ammonia ($NH_3$), hydrocarbons (e.g., methane ($CH_4$)), $CO_2$, CO, formaldehyde ($CH_2O$), hydrogen sulfide ($H_2S$), carbonyl sulfide, (COS), hydrogen cyanide (HCN), water vapor, inert gases, or other gases. In certain embodiments, microorganisms of this disclosure utilize a $CO_x$ substrate or feedstock, which optionally is in the presence of $H_2$ and which may also include various other components as noted above.

As used herein, "synthesis gas" or "syngas" refers to a mixture of carbon monoxide and hydrogen, which may be produced, for example, by steam reforming, dry or $CO_2$ reforming, autothermal reforming, catalytic partial oxidation or partial oxidation of natural gas or liquid hydrocarbons, within hydrogen synthesis, within ammonia synthesis, within methanol synthesis, by steelmaking, or by gasification of coal, biomass or waste. In certain embodiments, syngas can be further conditioned by a water-gas shift reaction. Syngas may also include methane, $CO_2$, $H_2S$, or other gases in smaller quantities relative to CO and $H_2$.

As used herein, the term "host" refers to a cell or microorganism (e.g., Archaea) that may be genetically modified by mutation, with an exogenous nucleic acid molecule to produce a polypeptide of interest (e.g., deregulated MMP1358, deregulated MMP1359), by knockout or combinations thereof, to improve the production of methionine over the unmodified host cell. In certain embodiments, a host cell may optionally already possess other genetic modifications that confer desired properties related or unrelated to the mutated or exogenous polypeptide being expressed (e.g., deregulation). For example, a host cell may possess or be altered to possess genetic modifications conferring additional or enhanced carbon flux activity into the methionine pathway, reduced production of competing amino acids, high growth, tolerance of contaminants or particular culture conditions, ability to metabolize additional carbon substrates, or ability to synthesize desirable products or intermediates.

As used herein, "hydrogenotroph" or "hydrogenotrophic" refers to a microorganism capable of consuming $H_2$, oxidizing $H_2$, or converting $H_2$ into another compound as part of its metabolism. In certain embodiments, a hydrogenotroph may be an obligate or facultative hydrogenotroph, an obligate or facultative anaerobe, or any combination thereof. For example, a facultative hydrogenotroph may grow in the presence or absence of hydrogen as an energy source, and may use one or more various carbon sources, such as carbohydrates, acetate, formate, methanol, methylamines, or carbon oxide (e.g., an Acetogen, *Clostridium*, may grow in the absence of $H_2$ and use acetate as both an energy and carbon source; *Methanosarcina mazei* may survive in the absence of $H_2$ by using an alternative metabolic pathways for methanogenesis by using, for example, acetate, methylamines, or methanol). Exemplary hydrogenotrophs include Methanogens, Acetogens, Knall-gas bacteria, or the like.

As used herein, the term "methanogen" or "methanogenic archaea" refers to an archaeal microorganism capable of producing methane under anoxic conditions using any one or more methanogenesis pathway, including (a) using any of various one or two carbon substrates (e.g., carbon dioxide, acetate, formic acid, formaldehyde, carbon monoxide, methanol, methyl amines (e.g., methylamine, dimethylamine, trimethylamine, or the like)) and hydrogen gas; (b) using acetate in an acetoclastic pathway, and (c) using reduced one carbon compounds or multi-carbon compounds lacking a carbon-carbon bond in a methylotrophic methanogenesis pathway. For example, *Methanosarcina* species possess all three known pathways for methanogenesis, which are archaea capable of utilizing at least nine methanogenic substrates (e.g., methanol, methylamines, methylthiols, acetate), although *Methanosarcina acetivorans* is unable to subsist on $H_2/CO_2$ reduction since it lacks a functional $H_2$ reducer, unlike *Methanosarcina mazei* (Maeder et al., *J. Bacteriol.* 188:7922, 2006). But, *Methanosarcina acetivorans* may grow by metabolizing CO into acetate and formate, by oxidizing CO into $CO_2$, or by using acetate as an electron acceptor when producing methane. It is understood in the art that bacteria are not archaea and archaea are not bacteria. As used herein, methanogenic archaea may be "obligate hydrogenotrophs," which require hydrogen gas to produce methane (e.g., *Methanocella conradii*). Methanogenic archaea may be "facultative hydrogenotrophs," which are able to produce methane in the absence of hydrogen gas (e.g., *Methanosarcina mazei*). Furthermore, methanogenic archaea may be mesophilic, thermophilic or hyperthermophilic.

As used herein, "biomass" refers to organic material having a biological origin, which may include whole cells, lysed cells, extracellular material, product produced or a portion thereof, or the like. For example, the material harvested from a cultured microorganism (e.g., bacterial or archaeal culture) may be considered the biomass, which can include secreted products or can be the secreted products.

As used herein, "nucleic acid molecule," also known as a polynucleotide, refers to a polymeric compound comprised of covalently linked subunits called nucleotides. Nucleic acid molecules include polyribonucleic acid (RNA), polydeoxyribonucleic acid (DNA), both of which may be single or double stranded. DNA includes cDNA, genomic DNA, synthetic DNA, semi-synthetic DNA, or the like.

As used herein, the term “endogenous” or “native” refers to a gene, protein, compound or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

As used herein, “heterologous” or “exogenous” nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, “heterologous” refers to a non-native enzyme, protein or other activity encoded by an exogenous nucleic acid molecule introduced into the host cell, even if the host cell encodes a homologous protein or activity.

The term “homologous” or “homolog” refers to a molecule or activity similar to that found in or derived from a host cell, species or strain. For example, a heterologous or exogenous nucleic acid molecule may be homologous to a native host cell gene, and may optionally have an altered expression level, a different sequence, an altered activity, or any combination thereof. A homologous polynucleotide or polypeptide may have a polynucleotide or polypeptide sequence that is at least 70%, at least 75%, at least 80%, at least 85%, at least 90%, at least 91%, at least 92%, at least 93%, at least 94%, at least 95%, at least 96%, at least 97%, at least 98%, at least 99% identical, or 100% identical to a reference or parental wild-type sequence. In certain embodiments, homologous polypeptides will include at least one amino acid substitution (e.g., at least 1, 2, 3, 5, 6, 7, 8, 9 or 10 or more or up to 20, 25, or 30 substitutions) or no more than a particular number of amino acid substitutions (e.g., no more than 1, 2, 3, 5, 6, 7, 8, 9, 10, 15, 20, 25, or 30 substitutions) at one or more pre-determined positions relative to a reference or parental wild-type enzyme, provided that a homologous protein or polypeptide retains an activity of interest (e.g., carboxylase, decarboxylase, dehydrogenase, epimerase, kinase, lyase, reductase, synthase).

As used herein, the term “non-natural” or “non-natural engineered” refers to an organism, microorganism, cell, nucleic acid molecule, or vector that has been genetically engineered to include at least one genetic alteration that differs from a wild-type or parent cell or molecule. For example, non-natural may refer to a microorganism or cell that has been engineered (e.g., site-specific or random mutants, including spontaneous mutants) such that the expression of an endogenous nucleic acid molecule or gene, or the activity of a gene product, has been altered (e.g., increased, decreased, deregulated, activated, derepressed, repressed) as compared to a wild-type or parent microorganism. Such modifications include, for example, those in non-coding regulatory regions that alter (increase or decrease) expression of a gene or operon. A “non-natural” organism, microorganism, or cell can include recombinant organisms, microorganisms, or cells.

As used herein, the term “recombinant” refers to a microorganism, cell, nucleic acid molecule, or vector that has been modified by introduction of an exogenous nucleic acid molecule, or refers to a microorganism or cell that has been altered such that expression of an endogenous nucleic acid molecule or gene is controlled, deregulated or constitutive, where such alterations or modifications may be introduced by genetic engineering. Genetic alterations may include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell’s genetic material. Exemplary modifications include those in coding regions or functional fragments thereof of heterologous or homologous polypeptides from a reference or parent microorganism. In certain embodiments, an organism, microorganism, or cell of this disclosure is a non-natural organism, microorganism, or cell and a recombinant organism, microorganism, or cell. For example, a non-natural hydrogenotrophic microorganism that expresses or overexpresses a deregulated endogenous enzyme (e.g., MMP1359, MMP1358, aspartokinase, homoserine O-acetyltransferase) may also contain one or more exogenous or heterologous nucleic acid molecules that are expressed or overexpressed to produce certain enzyme activities involved in biosynthesis of methionine (e.g., asparate semialdehyde dehydrogenase, homoserine, O acetylhomoserine sulfhydrylase, homocysteine S methyltransferase, methionine synthase dehydrogenase).

As used herein, “transformation” refers to the introduction of a nucleic acid molecule (e.g., exogenous or heterologous nucleic acid molecule) into a host cell. The transformed host cell may carry the exogenous or heterologous nucleic acid molecule extra-chromosomally or integrated in the chromosome. Integration into a host cell genome and self-replicating vectors generally result in genetically stable inheritance of the transformed nucleic acid molecule. Host cells containing the transformed nucleic acids are referred to as “recombinant” or “genetically engineered” or “transformed” or “transgenic” cells (e.g., Archaea).

As used herein, the term “deregulated” refers to reduced or increased expression of a gene product, or reduced or increased activity of a gene product (e.g., a protein, enzyme) as compared to gene expression or activity, respectively, in a parent or wild-type microorganism. For example, a microorganism can be genetically manipulated (e.g., mutated, genetically engineered) to increase or decrease the expression of a gene product or to increase or reduce the activity of the gene product over that of a parent or wild-type microorganism prior to manipulation. In certain embodiments, a target gene is mutated such that the expressed gene product has increased activity. For example, the coding region of a target gene may be altered so that the expressed gene product has increased activity, the copy number of the target gene may be increased to increase activity, a target gene may be overexpressed to increase activity, or any combination thereof. In other embodiments, a target gene is mutated such that the expressed gene product has a reduced, minimal or non-detectable response to feedback inhibition (e.g., an amino acid biosynthetic enzyme, such as MMP1358 or MMP1359 or both are deregulated in the presence of one or more feedback inhibitors, such as methionine or S-adenosylmethionine). In further embodiments, a target gene is mutated such that the gene has a reduced, minimal or non-detectable response to repression of expression (e.g., an amino acid biosynthetic enzyme, such as homoserine dehydrogenase, is deregulated in the presence of feedback co-repressor methionine). Alternatively, a microorganism may be identified, for example, under selective pressure to have any one or more of the above-noted genetic alterations (e.g., spontaneous mutants). A deregulated gene or gene product of any of the aforementioned embodiments may be a spontaneous, induced or engineered mutant or variant.

As used herein, the term "overexpressed" refers to a level of gene expression or gene product in a non-natural or recombinant microorganism that is greater than the level of gene expression or gene product found in a parent or wild-type microorganism when grown under the same conditions. In certain embodiments, overexpression may occur at the transcriptional level, translational level, or both, which may be due to altered regulatory control (e.g., use of a strong promoter) or an increase in copy number or both.

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. For example, an algorithm suitable for determining percent sequence identity and sequence similarity is the BLAST 2.0 algorithm used at default settings, which is described in Altschul et al. (1990) J. Mol. Biol. 215:403.

Variants of the polynucleotides or polypeptides of this disclosure are also contemplated. Variant polynucleotides or polypeptides are at least 70%, 75%, 80%, 85%, 90%, 95%, 99%, or 99.9% identical to one of the polynucleotides or polypeptides as described herein. In some embodiments, variant polynucleotides are those that hybridize to polynucleotides of defined sequence under stringent hybridization conditions of 0.015M sodium chloride, 0.0015M sodium citrate at about 65-68° C. or 0.015M sodium chloride, 0.0015M sodium citrate, and 50% formamide at about 42° C. (see Sambrook et al., *Molecular Cloning: A Laboratory Manual,* 2nd Ed., Cold Spring Harbor Laboratory, Cold Spring Harbor, N.Y., 1989). The polynucleotide variants retain the capacity to encode a biosynthetic enzyme or polypeptide thereof having the functionality described herein.

More stringent conditions (such as higher temperature, lower ionic strength, higher formamide, or other denaturing agent) may also be used; however, the rate of hybridization will be affected. In instances wherein hybridization of deoxyoligonucleotides is concerned, additional exemplary stringent hybridization conditions include washing in 6×SSC, 0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

A "mutant" refers to a change in the polynucleotide or polypeptide sequence as compared to a reference nucleic acid molecule or amino acid sequence. A mutation may be caused by radiation, viruses, transposons, mutagenic chemicals, errors that occur during meiosis or DNA replication, hypermutation, or the like. A mutation can result in several different types of sequence changes, including nucleotide or amino acid substitution, insertion, deletion or any combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, N.Y., pp. 71-77, 1975; Lewin, Genes IV, Oxford University Press, NY and Cell Press, Cambridge, Mass., p. 8, 1990).

"Inhibit" or "inhibited," as used herein, refers to an alteration, reduction, down regulation or abrogation, directly or indirectly, in the expression of a target gene or in the activity of a target molecule (e.g., phosphoenolpyruvate synthase) relative to a control, endogenous or reference molecule, wherein the alteration, reduction, down regulation or abrogation is statistically, biologically, industrially, or clinically significant. For example, an inhibited, inactivated or reduced activity biosynthetic enzyme (e.g., genetically altered) may possess 35%, 30%, 25%, 20%, 15%, 14%, 13%, 12%, 11%, 10%, 9%, 8%, 7%, 6%, 5%, 4%, 3%, 2%, 1%, or less activity as compared to a wild-type or parent enzyme.

Hydrogenotrophic Microorganisms—Host Cells

A parent or starting hydrogenotrophic microorganism of the instant disclosure may be a wild-type (natural) strain, a mutated (non-natural) strain (e.g., increased growth rate, deregulated or derepressed biosynthetic enzyme), or a recombinant strain, each of which may be further modified to produce methionine at a higher level than the parent hydrogenotrophic microorganism. In certain embodiments, a hydrogenotroph may be a methanogenic archaea.

In certain embodiments, the present disclosure provides hydrogenotrophic microorganisms that are methanogenic archaea, such as *Methanobacterium, Methanobrevibacter, Methanocalculus, Methanocaldococcus, Methanocella, Methanococcus, Methanococcoides, Methanocorpusculum, Methanoculleus, Methanofollis, Methanogenium, Methanohalobium, Methanohalophilus, Methanolacinia, Methanolobus, Methanomethylovorans, Methanomicrobium, Methanomicrococcus, Methanoplanus, Methanopyrus, Methanoregula, Methanosaeta, Methanosalsum, Methanosarcina, Methanosphaera, Methanospirillium, Methanothermobacter, Methanothermococcus, Methanothermus*, or *Methanotorris.*

In further embodiments, a hydrogenotrophic microorganism is a particular methanogenic archaea species. Exemplary methanogenic archaea species include *Methanobacterium alcaliphilum, Methanobacterium bryantii, Methanobacterium congolense, Methanobacterium defluvii, Methanobacterium espanolae, Methanobacterium formicicum, Methanobacterium ivanovii, Methanobacterium palustre, Methanobacterium thermaggregans, Methanobacterium uliginosum, Methanobrevibacter acididurans, Methanobrevibacter arboriphilicus, Methanobrevibacter gottschalkii, Methanobrevibacter olleyae, Methanobrevibacter ruminantium, Methanobrevibacter smithii, Methanobrevibacter woesei, Methanobrevibacter wolinii, Methanocaldococcus vilosus, Methanocella arvoryzae, Methanocella conradii, Methanocella paludicola, Methanothermobacter marburgensis, Methanothermobacter thermautotrophicum, Methanothermobacter thermoflexus, Methanothermobacter thermophilus, Methanothermobacter wolfeii, Methanothermococcus okinawensis, Methanothermus*

*sociabilis, Methanocorpusculum bavaricum, Methanocorpusculum parvum, Methanoculleus chikuoensis, Methanoculleus submarinus, Methanogenium frigidum, Methanogenium liminatans, Methanogenium marinum, Methanomicrococcus blatticola, Methanoplanus endosymbiosus, Methanoplanus limicola, Methanoplanus petrolearius, Methanopyrus kandleri, Methanoregula boonei, Methanotorris formicicus, Methanotorris igneus, Methanosaeta concilii, Methanosaeta harundinacea, Methanosaeta pelagica, Methanosaeta thermophila, Methanosarcina acetivorans, Methanosarcina barkeri, Methanosarcina mazei, Methanosarcina thermophila, Methanomicrobium mobile, Methanococcus aeolicus, Methanococcus maripaludis, Methanococcus vannielii, Methanococcus voltae, Methanothermococcus thermolithotrophicus, Methanopyrus kandleri, Methanothermobacter thermoautotroiphicus, Methanocaldococcus fervens, Methanocaldococcus indicus, Methanocaldococcus infernus, Methanocaldococcus jannaschii*, and *Methanocaldococcus vulcanius.*

In certain embodiments, methanogenic archaea produce cytochromes or do not produce cytochromes. For example, methanogenic archaea that do not produce cytochromes include *Methanococcus maripaludis* or *Methanococcus vannielii*. An exemplary methanogenic archaea that does produce cytochromes is *Methanosarcina barkeri* or *Methanosarcina mazei.*

In related embodiments, a methanogenic archaea may be mesophilic, thermophilic or hyperthermophilic. Exemplary mesophilic methanogens include some species of *Methanobacterium, Methanobrevibacter, Methanocalculus, Methanocaldococcus, Methanococcus, Methanocorpusculum*, and *Methanosarcina*. Exemplary thermophilic methanogens include some species of *Methanomicrobium, Methanosaeta, Methanosarcina*, and *Methanothermococcus*. Exemplary hyperthermophilic methanogens include some species of *Methanocaldococcus, Methanopyrus, Methanothermus*, and *Methanotorris.*

Methionine Producing Hydrogenotrophic Microorganisms

The hydrogenotrophic microorganisms of this disclosure can be genetically manipulated (i.e., genetically engineered), recombinantly modified or combinations thereof to knock-out, reduce, express or over-express sulfur assimilation polypeptides of interest, which results in recombinant microorganisms useful for converting (e.g., utilizing, converting, assimilating, oxidizing, reducing) various components of a $H_2/CO_x$ substrate into methionine or methionine containing feed.

Genetic manipulation or engineering to generate non-natural hydrogenotrophic microorganisms can include random (e.g., chemically-induced, spontaneous) or site-directed mutagenesis (e.g., of one or more gene targets), alteration of regulatory sequences or sites associated with expression of one or more gene targets (e.g., by removing strong, weak, inducible, repressible, or multiple promoters, or by replacing such promoters with promoters having different properties), changing the chromosomal location of one or more gene targets, altering nucleic acid sequences adjacent to one or more gene targets (such as a ribosome binding site or transcription terminator), decreasing or increasing the copy number of one or more gene targets, modifying regulatory proteins, repressors, suppressors, enhancers, transcriptional activators or the like involved in transcription of one or more gene targets or translation of one or more gene products, or any other method of deregulating expression of one or more gene targets (including the use of antisense nucleic acid molecules, short interfering nucleic acid molecules, or other methods to knock-out or block expression of a target protein).

In certain embodiments, a genetic manipulation or engineering comprises one or more spontaneous mutations (e.g., chemical, radiological, or other mutagenic treatment) that result in a non-natural hydrogenotrophic microorganism that produces more methionine than the parent microorganism. Such spontaneous mutants can be produced and identified, for example, by placing microorganisms under a particular selective pressure where only a mutant with the desired phenotype will grow (e.g., absence of a particular amino acid or toxin in the growth medium, presence of an antibiotic, absence of a particular metabolite, or the like).

In further embodiments, endogenous or exogenous nucleic acid molecules encoding a methionine biosynthetic enzyme may be altered, such as having an amino acid sequence changed from wild-type. Each variant polypeptide generated by these methods will retain at least 50% activity (preferably 100% or more activity) and have a polypeptide sequence that is at least 90%, at least 91%, at least 92%, at least 93%, at least 94%, at least 95%, at least 96%, at least 97%, at least 98%, at least 99% identical, or 100% identical to a reference or parental wild-type polypeptide sequence. In certain embodiments, variant polypeptides will include at least one amino acid substitution (e.g., at least 1, 2, 3, 5, 6, 7, 8, 9 or 10 or more or up to 20, 25, or 30 substitutions) or no more than a particular number of amino acid substitutions (e.g., no more than 1, 2, 3, 5, 6, 7, 8, 9, 10, 15, 20, 25, or 30 substitutions) at one or more pre-determined positions relative to a reference or parental wild-type enzyme, provided that a variant retains an activity of interest (e.g., carboxylase, decarboxylase, dehydrogenase, epimerase, kinase, lyase, reductase, synthase).

In certain aspects, the present disclosure relates to the unexpected result that sulfur assimilation enzymes encoded by open reading frames (ORFs) MMP1359 (GenBank No. NC_005791.1 (1337240 . . . 1338781, complement); NCBI Gene ID: 2762444, SEQ ID NO.:1), MMP1358 (GenBank No. NC_005791.1 (1336828 . . . 1337226, complement), NCBI Gene ID: 2762433; SEQ ID NO.:5), or both are involved in the methionine biosynthesis pathway and subject to feedback inhibition by methionine or S-adenosylmethionine. In some embodiments, sulfur assimilation enzyme MMP1359, MMP1358, or both are from the hydrogenotrophic archaea *Methanococcus maripaludis*. In further embodiments, the present disclosure provides a mutated ORF that encodes a MMP1359 resistant to methionine feedback inhibition (e.g., SEQ ID NO.:2), a mutated ORF that encodes a MMP1358 resistant to methionine feedback inhibition (e.g., SEQ ID NO.:6), or both that result in increased methionine production when expressed by a host cell as compared to a host cell expressing a parent, wild-type or reference polypeptide. Collectively, the MMP1359 and MMP1358 polypeptides, or mutants, variants, homologs, or orthologs thereof are collectively referred to herein as "sulfur assimilation polypeptides" or "methionine pathway polypeptides."

In certain embodiments, a homolog or ortholog of MMP1359, MMP1358, or both may be obtained from *Desulfomonile tiedjei, Syntrophothermus lipocalidus, Acetobacterium woodii, Tepidanaerobacter acetatoxydans, Syntrophomonas wolfei, Thermodesulfobium narugense, Odoribacter splanchnicus, Thermotoga thermarum, Thermosipho melanesiensis, Sphaerochaeta globosa*, or any combination thereof.

Accordingly, the present disclosure provides hydrogenotrophic microorganisms having endogenously-modified to be deregulated (e.g., no longer subject to feedback inhibition by methionine or S-adenosylmethionine), or recombinantly expressed or overexpressed (wild-type or deregulated), polypeptides involved in the biosynthesis of methionine, such as deregulated sulfur assimilation polypeptides (e.g., MMP1359, MMP1358) disclosed herein. In addition, hydrogenotrophic microorganisms of this disclosure can further express or overexpress additional enzymes of the methionine biosynthesis pathway, such as aspartokinase, aspartyl semialdehyde dehydrogenase, homoserine dehydrogenase, homoserine O-acetyltransferase, homoserine O-succinyltransferase, O-succinylhomoserine lyase, cystathionine γ-synthase, cystathionine β-lyase, O-acetylhomoserine sulfhydrylase, homocysteine S-methyltransferase, methionine synthase or combinations thereof, which activities may be endogenous, exogenous, or both. In certain embodiments, a hydrogenotrophic microorganism having a deregulated or overexpressed MMP1359 and/or MMP1358, and an aspartokinase, may optionally have an endogenous or recombinantly added homoserine dehydrogenase activity. In particular embodiments, a hydrogenotrophic microorganism comprises a polynucleotide encoding a mutated MMP1359 that is resistant to methionine feedback inhibition (e.g., SEQ ID NO.:2), a polynucleotide encoding a mutated MMP1358 that is resistant to methionine feedback inhibition (e.g., SEQ ID NO.:6), or both, and optionally comprises an heterologous polynucleotide encoding a methionine synthase.

Methods for engineering and identifying feedback resistant mutants are known in the art—for example, microorganisms capable of growing in the presence of toxic amino acid analogs, such as lysine analog S-2-aminoethyl-L-cysteine (AEC) or the methionine analog DL-ethionine, are considered to be feedback resistant to the amino acid corresponding to the toxic analog (see, e.g., Shiio et al., *Agric. Biol. Chem.* 54:3275, 1990; Kumar and Gomes, *Biotechnology Advances* 23:41-61, 2005).

The polynucleotides of the instant disclosure can be used to isolate corresponding sequences from other organisms, particularly other Archaea, more particularly other methanogens. In this manner, methods such as PCR, hybridization, or the like can be used to identify such sequences based on their sequence homology to the MMP1359 or MMP1358 nucleic acid molecule sequences set forth herein. Nucleic acid molecules isolated based on their sequence identity to the entire MMP1359 or MMP1358 ORF set forth herein, or to variants and fragments thereof, are encompassed by the present invention. Such sequences include sequences that are homologs or orthologs of the disclosed sequences. "Orthologs" is intended to mean coding sequences derived from a common ancestral coding sequence and which are found in different species as a result of speciation. Coding sequences found in different species are considered orthologs when their nucleotide sequences or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode a polypeptide that has sulfur assimilation activity or promotes methionine biosynthesis (and optionally degregulated, such as being resistant to feedback inhibition by one or more compounds, such as methionine or S-adensoyl methionine), and hybridize under stringent conditions to an MMP1359 or MMP1358 ORF, or to variants or fragments thereof, are encompassed by the present disclosure.

Variation in codon usage bias has been observed across different species of bacteria and archaea, which may affect recombinant protein expression in a heterologous host (Sharp et al., *Nucl. Acids Res.* 33:1141, 2005; Emery and Sharp, *Biol. Lett.* 7:131, 2011). In certain embodiments, nucleic acid molecules (e.g., nucleic acids encoding sulfur assimilation polypeptides or methionine biosynthesis enzymes) may be codon optimized prior to introduction into a host cell as described herein to improve or maximize protein expression. Codon optimization refers to the alteration of codon sequence in genes or coding regions at the nucleic acid molecule level to reflect a more common codon usage of a host cell without altering the amino acid encoded by the codon. Codon optimization methods for gene expression in heterologous hosts have been previously described (see, e.g., Welch et al., *Methods Enzymol.* 498:43, 2011; Henry and Sharp, *Mol. Biol. Evol.* 24:10, 2007; U.S. Patent Publication No. 2011/0111413).

In a PCR approach, oligonucleotide primers can be designed for use in PCR reactions to amplify corresponding DNA sequences from cDNA or genomic DNA extracted from any microorganism (e.g., archaea) of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include methods using paired primers, nested primers, single specific primers, degenerate primers, gene-specific primers, vector-specific primers, partially-mismatched primers, or the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be based on genomic DNA fragments, cDNA fragments, RNA fragments, or other oligonucleotides, and may be labeled with a detectable group, such as $^{32}P$, or any other detectable marker. Thus, for example, probes for hybridization can be made by labeling synthetic oligonucleotides based on the MMP1359 or MMP1358 polynucleotides identified herein. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire MMP1359 or MMP1358 polynucleotide disclosed herein, or one or more portions thereof, may be used as a probe capable of specifically hybridizing to corresponding ORF, cDNA or mRNA polynucleotides. To achieve specific hybridization under a variety of conditions, such probes include sequences that are unique among MMP1359 or MMP1358 polynucleotide sequences and are optimally at least about 10 nucleotides in length, and most optimally at least about 20 nucleotides in length. Such probes may be used to amplify corresponding sulfur assimilation polynucleotides from a chosen microorganism by PCR. This technique may be used to isolate additional coding sequences from a desired microorganism to determine the presence of coding sequences in a hydrogenotrophic microorganism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that have 100% sequence identity to a probe can be identified. Alternatively, stringency conditions can be adjusted to allow some mismatching in sequences so that lower degrees of similarity can be detected (e.g., 60% to 99% sequence identity).

In certain aspects, the present disclosure provides a non-natural hydrogenotrophic microorganism, wherein the non-natural hydrogenotrophic microorganism metabolizes a $H_2/CO_x$ substrate to produce methionine at a higher level than a parent hydrogenotrophic microorganism and wherein the non-natural hydrogenotrophic microorganism expresses a polypeptide comprising a deregulated endogenous sulfur assimilation polypeptide. In some embodiments, a sulfur assimilation polypeptide comprises an amino acid sequence as set forth in SEQ ID NO.:4 or 8. In other embodiments, a sulfur assimilation polypeptide comprises an amino acid sequence comprising at least 70%, 75%, 80%, 85%, 90%, 91%, 92%, 93%, 94%, 95%, 96%, 97%, 98%, or 99%, sequence identity to SEQ ID NO.:4 or 8, wherein the polypeptide is deregulated for one or more feedback inhibitors (such as methionine or S-adenosylmethionine). In further embodiments, a sulfur assimilation polypeptide comprises an amino acid sequence encoded by a nucleic acid molecule comprising at least 70%, 75%, 80%, 85%, 90%, 91%, 92%, 93%, 94%, 95%, 96%, 97%, 98%, or 99%, sequence identity to SEQ ID NO.:2 or 6, wherein the encoded polypeptide is deregulated for one or more feedback inhibitors (such as methionine or S-adenosylmethionine). In yet further embodiments, a sulfur assimilation polypeptide comprises an amino acid sequence encoded by a nucleic acid molecule that hybridizes under stringent conditions to the complement of SEQ ID NO.:2 or 6, wherein the encoded polypeptide is deregulated for one or more feedback inhibitors (such as methionine or S-adenosylmethionine).

In some embodiments, a sulfur assimilation polypeptide is encoded by a mutant MMP1359 or homolog or ortholog thereof comprising an engineered spontaneous mutation, random mutation, site specific mutation, or any combination thereof. In other embodiments, a sulfur assimilation polypeptide is encoded by a mutant MMP1358 or homolog or ortholog thereof comprising a spontaneous mutation, random mutation, site specific mutation, or any combination thereof. In further embodiments, a sulfur assimilation polypeptide is encoded by a mutant MMP1359 or homolog or ortholog thereof comprising an engineered spontaneous mutation, random mutation, site specific mutation, or any combination thereof; and by a mutant MMP1358 or homolog or ortholog thereof comprising an engineered spontaneous mutation, random mutation, site specific mutation, or any combination thereof.

In certain embodiments, a deregulated endogenous or heterologous sulfur assimilation polypeptide is an MMP1359 mutant or homolog or ortholog thereof that is deregulated for one or more feedback inhibitors (such as methionine or S-adenosylmethionine). In other embodiments, a deregulated endogenous or heterologous sulfur assimilation polypeptide is an MMP1358 mutant or homolog or ortholog thereof that is deregulated for one or more feedback inhibitors (such as methionine or S-adenosylmethionine). In further embodiments, a deregulated endogenous or heterologous sulfur assimilation polypeptide is an MMP1359 mutant or homolog or ortholog thereof that is deregulated for one or more feedback inhibitors (such as methionine or S-adenosylmethionine), and an MMP1358 mutant or homolog or ortholog thereof that is deregulated for one or more feedback inhibitors (such as methionine or S-adenosylmethionine).

When referring to MMP1359 mutants of this disclosure, reference is made to the residue numbering that corresponds to the amino acid positions of the *Methanococcus maripaludis* S2 (ATCC No. DSM14266) MMP1359 protein (GenBank Accession No. NP_988479.1). An exemplary mutation includes a mutation at residue D439 (e.g., a D439N substitution). When referring to MMP1358 mutants of this disclosure, reference is made to the residue numbering that corresponds to the amino acid position of the *Methanococcus maripaludis* S2 (ATCC No. DSM14266) MMP1358 protein (GenBank Accession No. NP_988478.1). An exemplary mutation includes a mutation at residue G114 (e.g., a G114E substitution).

As noted herein, the first committed enzyme in the biosynthesis of aspartate pathway amino acids (e.g., methionine) is aspartokinase, which may be subject to feedback regulation by one or more of lysine, threonine and methionine. For example, *E. coli* has three aspartokinase isozymes—two are bifunctional with aspartokinase and homoserine dehydrogenase activity, which are referred to as aspartokinase I-homoserine dehydrogenase I (AK/HD-I; thrA) and aspartokinase II-homoserine dehydrogenase II (AK/HD-II; metL), and the other has aspartokinase activity alone, which is referred to as aspartokinase III (AK-III; lysC). The AK/HD-I is subject to feedback regulation by threonine (as well as repression of expression by threonine and leucine), while AK/HD-II is subject to feedback regulation by methionine only and AK-III is subject to feedback regulation by lysine only (see Patte et al., *Biochim. Biophys. Acta* 136:245, 1967; Theze et al., *J. Bactenol.* 117:133, 1974). In contrast, the *Corynebacterium glutamicum* aspartokinase is feedback inhibited by both lysine and threonine (Sano and Shiio, 1970; Yoshida et al., 2007). Other enzymes involved in the biosynthesis of aspartate pathway amino acids are also subject to feedback inhibition, such as homoserine O-acetyltransferase and homoserine O-transsuccinyltransferase.

In some embodiments, the present disclosure provides a non-natural genetically engineered hydrogenotrophic microorganism expressing a deregulated MMP1359, MMP1358, or both, wherein the non-natural hydrogenotrophic microorganism further expresses or overexpresses a deregulated aspartokinase activity or methionine synthase, and wherein the non-natural hydrogenotrophic microorganism metabolizes a $CO_x$ substrate, optionally in the presence of $H_2$, to produce methionine at a higher level than a parent hydrogenotrophic microorganism. In certain embodiments, the deregulated aspartokinase activity is an endogenous aspartokinase, an exogenous aspartokinase, or both. In certain embodiments, a deregulated aspartokinase activity is an aspartokinase mutant that is resistant to feedback inhibition by one or more of lysine, threonine, and methionine. In some embodiments, a deregulated aspartokinase activity is encoded by a mutant lysC gene comprising a spontaneous mutation, random mutation, site specific mutation, or any combination thereof. In certain embodiments, an endogenous or exogenous aspartokinase is not deregulated and a heterologous methionine synthase (e.g., MetE) is overexpressed.

In further embodiments, a deregulated aspartokinase activity is encoded by a mutant lysC gene comprising a mutation at a threonine binding site, a lysine binding site, a lysine and threonine binding site, a site other than a lysine or threonine binding site, or any combination thereof. In certain embodiments, a deregulated aspartokinase activity is encoded by a mutant thrA gene comprising a mutation at a threonine binding site. In other embodiments, a deregulated aspartokinase activity is encoded by a mutant metL gene comprising a mutation at a methionine binding site.

When referring to lysC feedback resistant mutants of this disclosure, reference is made to the residue numbering that corresponds to the amino acid positions of the *Corynebacterium glutamicum* ATCC 13032 LysC protein (GenBank Accession No. CAF18822.1). Exemplary threonine binding site mutations include residue I272, D274, G277, E278, A279, D294, Q298, N372, N374, I375, or any combination thereof. Exemplary lysine binding site mutations include residue I291, I293, D294, T361, S381, E382, or any combination thereof. An exemplary lysine and threonine binding site mutation is at residue D294. Exemplary mutations at a site other than a lysine and threonine binding site include residue F283, N299, S301, S302, T308, T311, T336, G359, F364, M365, T380, R384, S386, or any combination thereof. Any one or more of the aforementioned mutations may be included in an aspartokinase of this disclosure, provided that the aspartokinase polypeptide retains its kinase activity.

In order for biosynthesis of methionine to occur efficiently, a certain amount of carbon flux must flow through the methionine pathway. One way to boost or enhance the production of methionine is to maximize the carbon flux into the methionine pathway, as provided by this disclosure.

In certain aspects, the instant disclosure provides a non-natural hydrogenotrophic microorganism expressing a deregulated MMP1359, MMP1358, or both, wherein the non-natural hydrogenotrophic microorganism has reduced phosphoenolpyruvate synthase activity, increased pyruvate kinase activity, increased 5-methyltetrahydrofolate corrinoid/iron sulfur protein methyltransferase activity, increased pyruvate carboxylase activity, increased aspartate aminotransferase activity, or any combination thereof, and wherein the non-natural hydrogenotrophic microorganism metabolizes a $H_2/CO_x$ substrate to produce methionine at a higher level than a parent hydrogenotrophic microorganism. In certain embodiments, a non-natural hydrogenotrophic microorganism expressing a deregulated MMP1359, MMP1358, or both has reduced phosphoenolpyruvate synthase activity, increased pyruvate kinase activity, or both. In certain other embodiments, a non-natural hydrogenotrophic microorganism expressing a deregulated MMP1359, MMP1358, or both has increased pyruvate carboxylase activity, increased pyruvate synthase, increased acetyl-CoA synthase, increased aspartate aminotransferase activity, or any combination thereof.

In further embodiments, a non-natural hydrogenotrophic microorganism expressing a deregulated endogenous sulfur assimilation polypeptide (such as a deregulated MMP1359, MMP1358, or both) also has a deregulated aspartokinase activity, reduced phosphoenolpyruvate synthase activity, increased pyruvate kinase activity, or any combination thereof. In still further embodiments, a non-natural hydrogenotrophic microorganism expressing a deregulated endogenous sulfur assimilation polypeptide also has a deregulated aspartokinase activity, increased 5-methyltetrahydrofolate corrinoid/iron sulfur protein methyltransferase activity, increased pyruvate carboxylase activity, increased pyruvate synthase, increased acetyl-CoA synthase, increased aspartate aminotransferase activity, or any combination thereof. In each of these embodiments, the non-natural hydrogenotrophic microorganism metabolizes a $CO_x$ substrate, optionally in the presence of $H_2$, to produce methionine at a higher level than a parent hydrogenotrophic microorganism.

As noted herein, several of the biosynthetic methionine pathway enzymes are subject to feedback regulation (e.g., MMP1359, MMP1358, aspartokinase, homoserine O-acetyltransferase, homoserine O-succinyltransferase), some of the genes encoding these enzymes are subject to repression (e.g., homoserine dehydrogenase), or both. Hence, production of methionine can be improved by relieving the regulation, repression, or both, as provided by this disclosure.

In further aspects, this disclosure provides a non-natural hydrogenotrophic microorganism, wherein the non-natural hydrogenotrophic microorganism comprises one or more deregulated and/or derepressed polypeptides from one or more pathways for biosynthesis of methionine, and wherein the non-natural hydrogenotrophic microorganism metabolizes $CO_x$ substrate, optionally in the presence of $H_2$, to produce methionine at a higher level than a parent hydrogenotrophic microorganism. In certain embodiments, a non-natural hydrogenotrophic microorganism expressing a deregulated MMP1359 activity, MMP1358 activity, or both also has an aspartokinase, homoserine dehydrogenase, homoserine O-acetyltransferase (e.g., metA), O-succinylhomoserine lyase (e.g., metB), or any combination thereof that are derepressed, deregulated, or both.

In addition to overproducing methionine, it would be advantageous to avoid extraction or isolation of the produced methionine from the microorganism. Accordingly, the present disclosure provides methods for enhanced production of methionine in the culture medium where isolation or purification methods are simplified.

In still further aspects, this disclosure provides a non-natural hydrogenotrophic microorganism expressing a deregulated MMP1359, MMP1358, or both, wherein the non-natural hydrogenotrophic microorganism expresses or overexpresses an exporter of methionine, and wherein the non-natural engineered or recombinant hydrogenotrophic microorganism metabolizes a $CO_x$ substrate, optionally in the presence of $H_2$, to produce methionine at a higher level than a parent hydrogenotrophic microorganism. In certain embodiments, a non-natural hydrogenotrophic microorganism expresses or overexpresses an exporter of methionine, such as an brnFE or metT of *Corneybacterium glutamicum* (see Trotschel et al., *J. Bacteriol.* 187:3786-94, 2005) operably linked to strong expression control sequence (e.g., a nif or tet promoter). In other embodiments, a non-natural hydrogenotrophic microorganism transporter/importer of methionine is knocked-out or inhibited.

Another way to ensure carbon flows to a methionine biosynthetic pathway is to remove production of the other competing amino acids. As provided in this disclosure, hydrogenotrophic microorganisms can be auxothrophs for one or more amino acids.

In yet further aspects, this disclosure provides a non-natural hydrogenotrophic microorganism, wherein the non-natural hydrogenotrophic microorganism is an auxotroph for one or more aspartate pathway amino acids, and wherein the non-natural hydrogenotrophic microorganism metabolizes a $CO_x$ substrate, optionally in the presence of $H_2$, to produce methionine at a higher level than a parent hydrogenotrophic microorganism. In certain embodiments, a non-natural hydrogenotrophic microorganism is a homoserine auxotroph, threonine auxotroph, or both. In certain other embodiments, a non-natural hydrogenotrophic microorganism is a lysine auxotroph, isoleucine auxotroph, glycine auxotroph, or any combination thereof. In some embodiments, a non-natural hydrogenotrophic microorganism is a lysine auxotroph, threonine auxotroph, or both. In certain embodiments, a non-natural hydrogenotrophic microorganism expressing a deregulated endogenous sulfur assimilation polypeptide is also a lysine auxotroph, threonine auxotroph, glycine auxotroph, or any combination thereof.

In further embodiments, a non-natural hydrogenotrophic microorganism expressing a deregulated endogenous sulfur assimilation polypeptide is also an auxotroph for one or more aspartate pathway amino acids. In still further embodiments, a non-natural hydrogenotrophic microorganism expressing a deregulated endogenous sulfur assimilation polypeptide is also a homoserine auxotroph, threonine auxotroph, or any combination thereof. In yet further embodiments, a non-natural hydrogenotrophic microorganism expressing a deregulated endogenous sulfur assimilation polypeptide is also a lysine auxotroph, isoleucine auxotroph, glycine auxotroph, or any combination thereof. In even further embodiments, a non-natural hydrogenotrophic microorganism expressing a deregulated endogenous sulfur assimilation polypeptide is also a lysine auxotroph, threonine auxotroph, or both. In certain embodiments, a non-natural hydrogenotrophic microorganism expressing a deregulated endogenous sulfur assimilation polypeptide is also a lysine auxotroph, threonine auxotroph, glycine auxotroph, or any combination thereof.

Sometimes, simply overexpressing one or more biosynthetic enzymes that are part of a methionine pathway will be useful in the hydrogenotrophic microorganisms of the instant disclosure. In further aspects, this disclosure provides a non-natural hydrogenotrophic microorganism that overexpresses a polypeptide from one or more pathways for biosynthesis of methionine, and wherein the non-natural hydrogenotrophic microorganism metabolizes a $CO_x$ substrate, optionally in the presence of $H_2$, to produce methionine at a higher level than a parent hydrogenotrophic microorganism.

In further embodiments, a non-natural hydrogenotrophic microorganism expressing a deregulated endogenous sulfur assimilation polypeptide also overexpresses a polypeptide from one or more pathways for biosynthesis of methionine. In certain further embodiments, a non-natural hydrogenotrophic microorganism expressing a deregulated endogenous sulfur assimilation polypeptide also overexpresses a homoserine dehydrogenase, homoserine O-acetyltransferase or both; or overexpresses homoserine O-acetyltransferase, O-acetylhomoserine sulfhydrylase or both; or overexpresses a polypeptide having aspartokinase activity.

Recombinant methods for expression of exogenous or heterologous nucleic acids in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Exemplary exogenous proteins or enzymes to be expressed include those involved in methionine biosynthesis (e.g., aspartokinase, aspartate semialdehyde dehydrogenase, homoserine dehydrogenase, homoserine O-acetyltransferase, homoserine O-succinyltransferase, O-succinylhomoserine lyase, cystathionine γ-synthase, cystathionine β-lyase, O-acetylhomoserine sulfhydrylase, homocysteine S-methyltransferase, methionine synthase (cobalamin dependent or independent), or any combination thereof) or enzymes affecting carbon flux into the methionine biosynthetic pathway (e.g., pyruvate kinase, pyruvate carboxylase, pyruvate synthase, acetyl-CoA synthase, aspartate aminotransferase, or any combination thereof). Genetic modifications to nucleic acid molecules encoding enzymes, or functional fragments thereof, can confer a biochemical or metabolic capability to a recombinant cell that is altered from its naturally occurring state.

Any of the hydrogenotrophic microorganisms of this disclosure may be transformed to comprise at least one exogenous nucleic acid to provide the host with a new or enhanced activity (e.g., enzymatic activity) or may be genetically modified to remove or substantially reduce an endogenous gene function using any of a variety of methods known in the art. Genetic tools for transfer and expression of heterologous nucleic acid molecules in hydrogenotrophic microorganisms, such as methanogenic archaea, is known in the art (see, e.g., Rother et al., *Curr. Opin. Microbiol.* 8:745, 2005; Leigh et al., *FEMS Microbiol. Rev.* 35:577, 2011). For example, tools are available for DNA delivery (Dodsworth et al., *Appl. Environ. Microb.* 76:5644, 2010; Metcalf et al., *Proc. Natl. Acad. Sci. U.S.A* 94:2626, 1997), for shuttle vectors (Gardner and Whitman, *Genetics* 152:1439, 1999; Metcalf et al., 1997), for regulated expression of heterologous genes (Lie and Leigh, *J. Bacteriol.* 184:5301, 2002; Chaban et al., *Mol. Microbiol.* 66:596, 2007; Guss et al., Archaea 2:193, 2008), and for knock-in or knock-out genetic exchange (Moore and Leigh, *J. Bacteriol.* 187:972, 2005; Pritchett et al., *Appl. Environ. Microb.* 70:1425, 2004). Therefore, various methods for inactivating, knocking-out, or deleting endogenous gene function in hydrogenotrophic microorganisms may be used.

In certain embodiments, promoters, codon optimization, or both can be used for high, constitutive expression of exogenous nucleic acid molecules encoding amino acid biosynthesis pathway enzymes in host hydrogenotrophic microorganisms. Regulated expression of an exogenous nucleic acid molecule in a host hydrogenotrophic microorganism (e.g., methanogenic archaea) may also be utilized. In certain embodiments, regulated expression of exogenous nucleic acid molecules encoding amino acid biosynthesis enzymes may be desirable to optimize growth rate of the non-natural or recombinant hydrogenotrophic microorganisms. Controlled expression of nucleic acid molecules encoding amino acid biosynthesis enzymes for response to the presence of a $H_2/CO_x$ substrate may improve growth based on the variety of different sources or ratios of $H_2/CO_x$ substrate available.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a $CO_x$ substrate, optionally in the presence of $H_2$, metabolizing microorganism can be modified to express two or more heterologous or exogenous nucleic acid molecules encoding desired enzymes of the methionine biosynthetic pathway (e.g., aspartokinase, aspartyl semialdehyde dehydrogenase, homoserine dehydrogenase, homoserine O-acetyltransferase, homoserine O-succinyltransferase, O-succinylhomoserine lyase, cystathionine γ-synthase, cystathionine β-lyase, O-acetylhomoserine sulfhydrylase, homocysteine S-methyltransferase, methionine synthase). When two or more exogenous nucleic acid molecules are introduced into a host $H_2/CO_x$ metabolizing microorganism, it is understood that the two or more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell.

For example, a hydrogenotrophic microorganism (such as a methanogen) can be recombinantly transformed to produce a polypeptide capable of utilizing, converting or metabolizing a $H_2/CO_x$ substrate (e.g., $H_2$ with $CO_2$, CO, or both) into methionine at a higher level than a parent microorganism. In any embodiment described herein, a hydrogenotrophic microorganism (such as a methanogen) can be recombinantly transformed to produce a polypeptide capable of utilizing, converting or metabolizing a $CO_x$ substrate, optionally in the presence of $H_2$.

In further embodiments, a non-natural hydrogenotrophic microorganism expressing a deregulated endogenous sulfur assimilation polypeptide, further comprises an exogenous nucleic acid molecule encoding one or more polypeptides from a methionine biosynthetic pathway, and the non-natural engineered hydrogenotrophic microorganism produces methionine at a higher level than the parent hydrogenotrophic microorganism, as described herein. In further embodiments, the one or more polypeptides from a methionine biosynthetic pathway are selected from aspartokinase, aspartate semialdehyde dehydrogenase, homoserine dehydrogenase, homoserine O-acetyltransferase, homoserine O-succinyltransferase (e.g., metA), O-succinylhomoserine lyase (e.g., metB), cystathionine γ-synthase, cystathionine β-lyase, O-acetylhomoserine sulfhydrylase, homocysteine S-methyltransferase, methionine synthase (cobalamin dependent or independent), or any combination thereof. In particular embodiments, a first exogenous nucleic acid molecule encodes a homoserine dehydrogenase, a serine acetyltransferase, or both, wherein the homoserine dehydrogenase, serine acetyltransferase, or both are optionally overexpressed, deregulated, or both.

In certain other embodiments, an exogenous nucleic acid molecule encodes a homoserine O-acetyltransferase, an O-acetylhomoserine sulfhydrylase, or both, wherein the homoserine O-acetyltransferase, O-acetylhomoserine sulfhydrylase, or both are optionally overexpressed, deregulated, or both are overexpressed. In still other embodiments, a first exogenous nucleic acid molecule encodes an *E. coli* ThrA (AK/HD-I), an *E. coli* MetL (AK/HD-II), a homoserine O-acetyltransferase, an O-acetylhomoserine sulfhydrylase, or combinations thereof, wherein the AK/HD-I, homoserine O-acetyltransferase, O-acetylhomoserine sulfhydrylase, or combinations thereof are optionally overexpressed, deregulated, or both are overexpressed. In particular embodiments, the *E. coli* ThrA (AK/HD-I) is a deregulated mutant, wherein the AK/HD-I is mutated at any one or more of amino acid positions G330, S345, S352, and G433.

In some embodiments, a non-natural engineered hydrogenotrophic microorganism expressing a deregulated endogenous sulfur assimilation polypeptide, further comprises an exogenous nucleic acid molecule encoding one or more polypeptides from a methionine biosynthetic pathway, and further has (a) one or more lysine biosynthetic pathway polypeptides that are knocked out or have reduced activity, (b) one or more threonine biosynthetic pathway polypeptides that are knocked out or have reduced activity, (c) one or more glycine biosynthetic pathway polypeptides that are knocked out or have reduced activity, (d) one or more methionine degradation pathway polypeptides (e.g., metK) that are knocked out or have reduced activity, or (e) any combination thereof. In certain embodiments, the nucleic acid molecule that encodes a dihydrodipicolinate synthase, a homoserine kinase, a threonine dehydratase, a serine hydroxymethyl transferase, or any combination thereof are knocked out or encode a reduced activity.

In any of the aforementioned non-natural engineered hydrogenotrophic microorganisms, the exogenous nucleic acid molecule is integrated into the genome or the exogenous nucleic acid molecule is in a self-replicating vector. Additionally, in any of the aforementioned non-natural hydrogenotrophic microorganisms, the non-natural hydrogenotrophic microorganism is a lysine auxotroph, threonine auxotroph, glycine auxotroph, or any combination thereof.

In certain aspects, the present disclosure provides a recombinant hydrogenotrophic microorganism, wherein the recombinant hydrogenotrophic microorganism metabolizes a $CO_x$ substrate, optionally in the presence of $H_2$ to produce methionine at a higher level than a parent hydrogenotrophic microorganism and wherein the recombinant hydrogenotrophic microorganism expresses or overexpresses a polypeptide comprising an exogenous sulfur assimilation polypeptide. In some embodiments, a sulfur assimilation polypeptide comprises an amino acid sequence as set forth in any one of SEQ ID NOS.:3, 4, 7, or 8. In other embodiments, a sulfur assimilation polypeptide comprises an amino acid sequence comprising at least 70%, 75%, 80%, 85%, 90%, 91%, 92%, 93%, 94%, 95%, 96%, 97%, 98%, or 99%, sequence identity to any one of SEQ ID NOS.:3, 4, 7, or 8, wherein the polypeptide is deregulated for one or more feedback inhibitors (such as methionine or S-adenosylmethionine). In further embodiments, a sulfur assimilation polypeptide comprises an amino acid sequence encoded by a nucleic acid molecule comprising at least 70%, 75%, 80%, 85%, 90%, 91%, 92%, 93%, 94%, 95%, 96%, 97%, 98%, or 99%, sequence identity to any one of SEQ ID NOS.:1, 2, 5, or 6, wherein the polypeptide is deregulated for one or more feedback inhibitors (such as methionine or S-adenosylmethionine). In yet further embodiments, a sulfur assimilation polypeptide comprises an amino acid sequence encoded by a nucleic acid molecule that hybridizes under stringent conditions to the complement of any one of SEQ ID NOS.:1, 2, 5, or 6, wherein the encoded polypeptide is deregulated for one or more feedback inhibitors (such as methionine or S-adenosylmethionine).

In some embodiments, a sulfur assimilation polypeptide is a mutant MMP1359 or homolog or ortholog thereof comprising a spontaneous mutation, random mutation, site specific mutation, or any combination thereof. In some embodiments, a sulfur assimilation polypeptide is a mutant MMP1358 or homolog or ortholog thereof comprising a spontaneous mutation, random mutation, site specific mutation, or any combination thereof. In certain embodiments, a sulfur assimilation polypeptide is an MMP1359 mutant or homolog or ortholog thereof that is deregulated for one or more feedback inhibitors (such as methionine or S-adenosylmethionine). In certain embodiments, a sulfur assimilation polypeptide is an MMP1358 mutant or homolog or ortholog thereof that is deregulated for one or more feedback inhibitors (such as methionine or S-adenosylmethionine).

In some embodiments, a recombinant hydrogenotrophic microorganism further comprises a deregulated endogenous sulfur assimilation polypeptide. In some embodiments, an endogenous sulfur assimilation polypeptide comprises an amino acid sequence as set forth in any one of SEQ ID NOS.:4 and 8. In other embodiments, an endogenous sulfur assimilation polypeptide comprises an amino acid sequence comprising at least 70%, 75%, 80%, 85%, 90%, 91%, 92%, 93%, 94%, 95%, 96%, 97%, 98%, or 99%, sequence identity to any one of SEQ ID NOS.:4 or 8, wherein the polypeptide is deregulated for one or more feedback inhibitors (such as methionine or S-adenosylmethionine). In further embodiments, an endogenous sulfur assimilation polypeptide comprises an amino acid sequence encoded by a nucleic acid molecule comprising at least 70%, 75%, 80%, 85%, 90%, 91%, 92%, 93%, 94%, 95%, 96%, 97%, 98%, or 99%, sequence identity to any one of SEQ ID NOS.:2 or 6, wherein the polypeptide is deregulated for one or more feedback inhibitors (such as methionine or S-adenosylmethionine). In yet further embodiments, an endogenous sulfur assimilation polypeptide comprises an amino acid sequence encoded by a nucleic acid molecule that hybridizes under stringent conditions to the complement of any one of SEQ ID NOS.:2 and 6, wherein the polypeptide is deregulated for one or more feedback inhibitors (such as methionine or S-adenosylmethionine).

In certain embodiments, a recombinant hydrogenotrophic microorganism further comprises a deregulated endogenous aspartokinase activity, an exogenous nucleic acid molecule encoding a polypeptide having aspartokinase activity, or both.

In some embodiments, the recombinant hydrogenotrophic microorganism, expresses or overexpresses a deregulated endogenous aspartokinase activity, wherein the recombinant hydrogenotrophic microorganism metabolizes a $CO_x$ substrate, optionally in the presence of $H_2$, to produce methionine at a higher level than a parent hydrogenotrophic microorganism. In certain embodiments, a deregulated aspartokinase activity is an aspartokinase mutant that is resistant to feedback inhibition by one or more of lysine, threonine, and methionine. In other embodiments, a deregulated aspartokinase activity is encoded by a mutant lysC gene comprising a spontaneous mutation, random mutation, site specific mutation, or any combination thereof.

In further embodiments, a deregulated aspartokinase activity is encoded by a mutant lysC gene comprising a mutation at a threonine binding site, a lysine binding site, a lysine and threonine binding site, a site other than a lysine or threonine binding site, or any combination thereof. In certain embodiments, a deregulated aspartokinase activity is encoded by a mutant thrA gene comprising a mutation at a threonine binding site. In other embodiments, a deregulated aspartokinase activity is encoded by a mutant metL gene comprising a mutation at a methionine binding site.

When referring to lysC feedback resistant mutants of this disclosure, reference is made to the residue numbering that corresponds to the amino acid positions of the *Corynebacterium glutamicum* ATCC 13032 LysC protein (GenBank Accession No. CAF18822.1). Exemplary threonine binding site mutations include residue I272, D274, G277, E278, A279, D294, Q298, N372, N374, I375, or any combination thereof. Exemplary lysine binding site mutations include residue I291, I293, D294, T361, S381, E382, or any combination thereof. An exemplary lysine and threonine binding site mutation is at residue D294. Exemplary mutations at a site other than a lysine and threonine binding site include residue F283, N299, S301, S302, T308, T311, T336, G359, F364, M365, T380, R384, S386, or any combination thereof. Any one or more of the aforementioned mutations may be included in an aspartokinase of this disclosure, provided that the aspartokinase polypeptide retains its kinase activity.

In some embodiments, the recombinant hydrogenotrophic microorganism comprises a second exogenous nucleic acid molecule encoding a polypeptide having aspartokinase activity, wherein the recombinant hydrogenotrophic microorganism is capable of assimilating a $CO_x$ substrate, optionally in the presence of $H_2$, to produce methionine at a higher level than a parent hydrogenotrophic microorganism. In some embodiments, a second exogenous nucleic acid molecule overexpresses the polypeptide having aspartokinase activity, or the second exogenous nucleic acid molecule encodes a deregulated exogenous aspartokinase activity, such as an exogenous aspartokinase mutant that is resistant to feedback inhibition by one or more of lysine, threonine, and methionine. In some embodiments, a deregulated exogenous aspartokinase activity is encoded by a mutated *E. coli* aspartokinase gene, such as a mutated aspartokinase I-homoserine dehydrogenase I protein (GenBank Accession No. BAB96579.2), a mutated aspartokinase II-homoserine dehydrogenase II protein (GenBank Accession No. BAE77370.1) or a mutated aspartokinase III protein (GenBank Accession No. BAE78026.1). In particular embodiments, a deregulated exogenous aspartokinase activity is provided by an *E. coli* aspartokinase ThrA protein (GenBank Accession No. BAB96579.2) mutated at any one or more of amino acid positions G330, S345, S352 and G433, or is provided by a mutant *E. coli* aspartokinase lysC protein (GenBank Accession No. BAE78026.1) mutated at amino acid position T342. In other embodiments, a deregulated exogenous, endogenous or both aspartokinase activities are individually encoded by a mutant thrA gene, metL gene, lysC gene or combinations thereof, each comprising a spontaneous mutation, random mutation, site specific mutation, or any combination thereof.

In further embodiments, an exogenous aspartokinase activities are individually encoded by a mutant lysC gene comprising a mutation at a threonine binding site, a lysine binding site, a lysine and threonine binding site, a site other than a lysine or threonine binding site, or any combination thereof. Exemplary threonine binding site mutations include residue I272, D274, G277, E278, A279, D294, Q298, N372, N374, I375, or any combination thereof. Exemplary lysine binding site mutations include residue I291, I293, D294, T361, S381, E382, or any combination thereof. An exemplary lysine and threonine binding site mutation is at residue D294. Exemplary mutations at a site other than a lysine and threonine binding site include residue F283, N299, S301, S302, T308, T311, T336, G359, F364, M365, T380, R384, S386, or any combination thereof. Any one or more of the aforementioned mutations may be included in an aspartokinase of this disclosure, provided that the aspartokinase polypeptide retains its kinase activity.

In other aspects, the present disclosure provides a recombinant hydrogenotrophic microorganism, comprising an exogenous nucleic acid molecule encoding a polypeptide having pyruvate kinase activity, an exogenous nucleic acid molecule encoding a polypeptide having pyruvate carboxylase activity, an exogenous nucleic acid molecule encoding a polypeptide having aspartate aminotransferase activity, or any combination thereof, optionally having reduced phosphoenolpyruvate synthase activity, wherein the recombinant hydrogenotrophic microorganism is capable of assimilating a $H_2/CO_x$ substrate to produce methionine at a higher level than a parent hydrogenotrophic microorganism. In certain embodiments, a recombinant hydrogenotrophic microorganism has reduced phosphoenolpyruvate synthase activity, increased pyruvate kinase activity, or both. In certain other embodiments, a recombinant hydrogenotrophic microorganism has increased pyruvate carboxylase activity, increased pyruvate synthase, increased acetyl-CoA synthase, increased aspartate aminotransferase activity, or any combination thereof.

In further aspects, this disclosure provides a recombinant hydrogenotrophic microorganism, comprising an exogenous nucleic acid molecule encoding an exporter of methionine, wherein the recombinant hydrogenotrophic microorganism is capable of assimilating a $H_2/CO_x$ substrate to produce methionine at a higher level than a parent hydrogenotrophic microorganism. In certain embodiments, a recombinant hydrogenotrophic microorganism further comprises an exogenous nucleic acid molecule that encodes an exporter of methionine, such as a brnFE or metT exporter. In other embodiments, a non-natural hydrogenotrophic microorganism transporter/importer of methionine is knocked-out or inhibited.

In yet further aspects, this disclosure provides a recombinant hydrogenotrophic microorganism, comprising a genetic modification to knock out biosynthesis of one or more aspartate pathway amino acids, wherein the recombinant hydrogenotrophic microorganism is an auxotroph for the one or more aspartate pathway amino acids and is capable of assimilating a $H_2/CO_x$ substrate to produce methionine at a higher level than a parent hydrogenotrophic microorganism. In certain embodiments, a recombinant hydrogenotrophic microorganism is a homoserine auxotroph, threonine auxotroph, glycine auxotroph, or any combination thereof. In certain other embodiments, a recombinant hydrogenotrophic microorganism is a lysine auxotroph, isoleucine auxotroph, glycine auxotroph, or any combination thereof. In some embodiments, a recombinant hydrogenotrophic microorganism is a lysine auxotroph, threonine auxotroph, glycine auxotroph, or any combination thereof.

In certain further aspects, this disclosure provides a recombinant hydrogenotrophic microorganism, comprising one or more exogenous nucleic acid molecules encoding polypeptides from one or more pathways for biosynthesis of methionine, wherein the one or more encoded polypeptides are overexpressed, and the recombinant hydrogenotrophic microorganism is capable of assimilating a $CO_x$ substrate, optionally in the presence of $H_2$, to produce methionine at a higher level than a parent hydrogenotrophic microorganism.

In certain embodiments, an asparate semialdehyde dehydrogenase, a homoserine dehydrogenase, a serine acetyltransferase, or any combination thereof are overexpressed; or a homoserine O-acetyltransferase, an O-acetylhomoserine sulfhydrylase or both are overexpressed; or a polypeptide having aspartokinase activity is overexpressed.

In further embodiments, a recombinant hydrogenotrophic microorganism having an exogenous nucleic acid molecule encoding a sulfur assimilation polypeptide, further comprises an exogenous nucleic acid molecule encoding one or more polypeptides from a methionine biosynthetic pathway, and the recombinant hydrogenotrophic microorganism produces methionine at a higher level than the parent hydrogenotrophic microorganism, as described herein. In further embodiments, the one or more encoded polypeptides from a methionine biosynthetic pathway are selected from aspartokinase, aspartyl semialdehyde dehydrogenase, homoserine dehydrogenase, homoserine O-acetyltransferase, homoserine O-transsuccinyltransferase (e.g., metA), O-succinylhomoserine lyase (e.g., metB), cystathionine γ-synthase, cystathionine β-lyase, O-acetylhomoserine sulfhydrylase, homocysteine S-methyltransferase, methionine synthase (cobalamin dependent or independent), or any combination thereof. In particular embodiments, a second exogenous nucleic acid molecule encodes a homoserine dehydrogenase, a serine acetyltransferase, or both, wherein the homoserine dehydrogenase, serine acetyltransferase, or both are optionally overexpressed, operably linked to a nucleic acid expression control sequence, deregulated, or any combination thereof. In certain other embodiments, an exogenous nucleic acid molecule encodes a homoserine O-acetyltransferase, an O-acetylhomoserine sulfhydrylase, or both, wherein the homoserine O-acetyltransferase, O-acetylhomoserine sulfhydrylase, or both are optionally overexpressed, operably linked to a nucleic acid control sequence, deregulated, or any combination thereof.

In some embodiments, a recombinant hydrogenotrophic microorganism having an exogenous nucleic acid molecule encoding a sulfur assimilation polypeptide further comprises an exogenous nucleic acid molecule encoding one or more polypeptides from a methionine biosynthetic pathway, and further has (a) one or more lysine biosynthetic pathway polypeptides that are knocked out or have reduced activity, (b) one or more threonine biosynthetic pathway polypeptides that are knocked out or have reduced activity, (c) one or more glycine biosynthetic pathway polypeptides that are knocked out or have reduced activity, or (d) any combination thereof. In certain embodiments, the nucleic acid molecule that encodes a dihydrodipicolinate synthase, a homoserine kinase, a threonine dehydratase, a threonine aldolase, a serine hydroxymethyl transferase, or any combination thereof are knocked out or encode a reduced activity dihydrodipicolinate synthase mutant, a homoserine kinase mutant, threonine dehydratase mutant, threonine aldolase mutant, serine hydroxymethyl transferase mutant, or any combination thereof.

In any of the aforementioned recombinant hydrogenotrophic microorganisms, the first exogenous nucleic acid molecule is integrated into the genome or the first exogenous nucleic acid molecule is in a self-replicating vector. Additionally, in any of the aforementioned recombinant hydrogenotrophic microorganisms, the recombinant hydrogenotrophic microorganism is a lysine auxotroph, threonine auxotroph, glycine auxotroph, or any combination thereof.

In certain embodiments, hydrogenotrophic microorganisms as described herein may be engineered to express or overproduce a mutant sulfur assimilation polypeptide having MMP1359 activity or a methionine feedback inhibition resistant MMP1359 activity. In some embodiments, hydrogenotrophic microorganisms as described herein may be engineered to express or overproduce a mutant sulfur assimilation polypeptide having MMP1358 activity or a methionine feedback inhibition resistant MMP1358 activity. In certain embodiments, hydrogenotrophic microorganisms as described herein may be engineered to express or overproduce a mutant sulfur assimilation polypeptide having methionine feedback inhibition resistant MMP1359 activity and a mutant sulfur assimilation polypeptide having methionine feedback inhibition resistant MMP1358 activity. In any of the aforementioned embodiments, the engineered hydrogenotrophic microorganisms further comprise a polynucleotide encoding a exogenous methionine synthase activity, wherein a cell overproduces the methionine synthase activity as compared to the parent cell lacking the exogenous methionine synthase.

For example, to express or overproduce a sulfur assimilation polypeptide having activity corresponding to MMP1359, one or more genes from *Methanococcus maripaludis, Methanosarcina acetivorans, Methanocella paludicola, Desulfomonile tiedjei, Syntrophothermus lipocalidus, Acetobacterium woodii, Tepidanaerobacter acetatoxydans, Syntrophomonas wolfei, Thermodesulfobium narugense, Ordoribacter splanchnicus*, or *Sphaerochaeta globose* can be introduced into and expressed or overexpressed in a hydrogenotrophic microorganism (e.g., methanogen), thereby producing or overproducing a polypeptide that is homologous to MMP1359 or a functional fragment thereof, which is optionally deregulated (i.e., resistant to methionine feedback inhibition). In certain embodiments, MMP1359 polypeptides of the compositions and methods disclosed herein are from *Methanococcus maripaludis* (NC_05791.1; MMP1359), *Methanosarcina acetivorans* (NC 003552.1; ORF1821), *Methanocella paludicola* (NC_013665.1; ORF 0132), *Desulfomonile tiedjei* (NC_018025.1; ORF 2525), *Syntrophothermus lipocalidus* (NC_014220.1; ORF0735), *Acetobacterium woodii* (NC_016894.1; ORFc28040), *Tepidanaerobacter acetatoxydans* (NC_019954.2; ORF2794), *Syntrophomonas wolfei* (NC_008346.1; ORF1441), *Thermodesulfobium narugense* (NC_015499.1; ORF 0230), *Ordoribacter splanchnicus* (NC_015160.1; ORF 3419), or *Sphaerochaeta globose* (NC_015152.1; ORF0032).

In some embodiments, a sulfur assimilation polypeptide amino acid sequence or a functional fragment thereof is based on the MMP1359 amino acid sequence from *Methanococcus maripaludis* S2 and is at least at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in GenBank Accession No. NP_988479.1, or a functional fragment thereof. In other embodiments, a recombinantly encoded MMP1359 has an amino acid sequence that is codon optimized for a host cell, or is identical to a sequence as set forth in GenBank Accession No. NP_988479.1. In particular embodiments, an MMP1359 amino acid sequence is an *M. maripaludis* protein (GenBank Accession No. NP_988479.1) mutated at amino acid position D439 (to, for example, asparagine).

For example, to express or overproduce a sulfur assimilation polypeptide having activity corresponding to MMP1358, one or more genes from *Methanococcus maripaludis, Methanosarcina acetivorans, Methanocella paludicola, Desulfomonile tiedjei, Syntrophothermus lipocalidus, Acetobacterium woodii, Tepidanaerobacter acetatoxydans, Syntrophomonas wolfei, Thermodesulfobium narugense, Ordoribacter splanchnicus*, or *Sphaerochaeta globose* can be introduced into and expressed or overexpressed in a hydrogenotrophic microorganism (e.g., methanogen), thereby producing or overproducing a deregulated polypeptide that is homologous to MMP1358 or a functional fragment thereof. In certain embodiments, sulfur assimilation polypeptides of the compositions and methods disclosed herein are from *Methanococcus maripaludis* (NC_05791.1; MMP1358), *Methanosarcina acetivorans* (NC_003552.1; ORF1822), *Methanocella paludicola* (NC_013665.1; ORF 0133), *Desulfomonile tiedjei* (NC_018025.1; ORF 2526), *Syntrophothermus lipocalidus* (NC_014220.1; ORF0736), *Acetobacterium woodii* (NC_016894.1; ORFc28030), *Tepidanaerobacter acetatoxydans* (NC_019954.2; ORF2795), *Syntrophomonas wolfei* (NC_008346.1; ORF1440), *Thermodesulfobium narugense* (NC_015499.1; ORF 0231), *Ordoribacter splanchnicus* (NC_015160.1; ORF 3418), or *Sphaerochaeta globose* (NC_015152.1; ORF0033).

In some embodiments, a sulfur assimilation polypeptide amino acid sequence or a functional fragment thereof is based on the MMP1358 amino acid sequence from *Methanococcus maripaludis* S2 and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in GenBank Accession No. NP_988478.1, or a functional fragment thereof. In other embodiments, a recombinantly encoded MMP1358 has an amino acid sequence that is codon optimized for a host cell, or is identical to a sequence as set forth in GenBank Accession No. NP_988478.1. In particular embodiments, an MMP1358 amino acid sequence is an *M. maripaludis* protein (GenBank Accession No. NP_988478.1) mutated at amino acid position G114 (to, for example, glutamic acid).

In some embodiments, a sulfur assimilation polypeptide is expressed or overexpressed having activity corresponding to both MMP1359 and MMP1358. For example, one or more genes from *Termotoga thermanrum* or *Termosipho melanesiensis* can be introduced into and expressed or overexpressed in a hydrogenotrophic microorganism (e.g., methanogen), thereby producing or overproducing a deregulated polypeptide that is homologous to MMP1359 and MMP1358, or a functional fragment thereof. In certain embodiments, the sulfur assimilation polypeptides of the compositions and methods disclosed herein are from *Termotoga thermanrum* (NC_015707.1; ORF0529) or *Termosipho melanesiensis* (NC_009626.1; ORF0733).

In some embodiments, a sulfur assimilation polypeptide amino acid sequence or a functional fragment thereof is based on GenBank Accession Nos. NC_015707.1; ORF0529 or NC_009626.1; ORF0733 amino acid sequence from *Termotoga thermanrum* or *Termosipho melanesiensis* and is at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in GenBank Accession Nos. NC_015707.1; ORF0529 or NC_009626.1; ORF073, or a functional fragment thereof. In other embodiments, a recombinantly encoded sulfur assimilation polypeptide has an amino acid sequence that is codon optimized for a host cell, or is identical to a sequence as set forth in GenBank Accession Nos. NC_015707.1; ORF0529 or NC_009626.1; ORF073.

In certain embodiments, hydrogenotrophic microorganisms as described herein may be engineered to express or overproduce a sulfur assimilation polypeptide, and optionally engineered to also express or overproduce an aspartokinase (EC 2.7.2.4), aspartyl semialdehyde dehydrogenase (EC 1.2.1.11), homoserine O-acetyltransferase (EC 2.3.1.31, homoserine O-succinyltransferase (e.g., metA; EC 2.3.1.46), O-succinylhomoserine lyase (e.g., metB; EC 2.5.1.48), cystathionine γ-synthase (EC 2.5.1.48), cystathionine β-lyase (EC 4.4.1.8), O-acetylhomoserine sulfhydrylase (EC 2.5.1.49), homocysteine S-methyltransferase (EC 2.1.1.10), or any combination thereof.

For example, to express or overproduce aspartokinase, one or more genes from *E. coli* (thrA), *E. coli* (metL), *E. coli* (lysC), *Corynebacterium glutamicum* (lysC), or *Methanococcus maripaludis* (lysC) can be introduced into and expressed or overexpressed in a hydrogenotrophic microorganism (e.g., methanogen), thereby producing or overproducing exogenous aspartokinase or a functional fragment thereof. In certain embodiments, aspartokinase polypeptides for use in the compositions and methods disclosed herein are from *Corynebacterium glutamicum* ATCC 13032 (Genbank Accession No. CAF18822.1), *Methanococcus maripaludis* S2 (Genbank Accession No. CAF30573.1), *Methanocella conradii* HZ254 (Genbank Accession No. AFD00291.1), *Methanobrevibacter ruminantium* M1 (Genbank Accession No. ADC47522.1), *E. coli* K-12 substr. W3110 thrA (GenBank Accession No. BAB96579.2); *E. coli* K-12 substr. W3110 metL (GenBank Accession No. BAE77370.1); *E. coli* K-12 substr. W3110 lysC (GenBank Accession No. BAE78026.1).

In some embodiments, an aspartokinase amino acid sequence or a functional fragment thereof is based on the thrA, metL, or lysC amino acid sequence from *E. coli* K-12 substr. W3110 and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. BAB96579.2, BAE77370.1 or BAE78026.1, respectively, or a functional fragment thereof. In other embodiments, a recombinantly encoded aspartokinase has an amino acid sequence that is codon optimized for a host cell, or is identical to a sequence as set forth in Genbank Accession Nos. BAB96579.2, BAE77370.1 or BAE78026.1, or comprises a consensus sequence of these aspartokinases or comprises a consensus sequence of a plurality of known aspartokinase polypeptides. In particular embodiments, an aspartokinase amino acid sequence is an *E. coli* ThrA protein (GenBank Accession No. BAB96579.2) mutated at any one or more of amino acid positions G330, 5345, 5352 and G433 (to, for example, aspartate, phenylalanine, or arginine), or is an *E. coli* LysC protein (GenBank Accession No. BAE78026.1) mutated at amino acid position T342 (to, for example, isoleucine).

In certain embodiments, an aspartokinase amino acid sequence or a functional fragment thereof is based on the amino acid sequence of *Corynebacterium glutamicum* ATCC 13032 or *Methanococcus maripaludis* S2 and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. CAF18822.1 or CAF30573.1, respectively, or a functional fragment thereof. In other embodiments, a recombinantly encoded aspartokinase has an amino acid sequence that is codon optimized for a host cell or is identical to a sequence as set forth in Genbank Accession Nos. CAF18822.1, CAF30573.1, AFD00291.1, or ADC47522.1, or comprises a consensus sequence of these aspartokinases or comprises a consensus sequence of a plurality of known aspartokinase polypeptides.

For example, to express or overproduce aspartyl semialdehyde dehydrogenase, one or more genes from *Corynebacterium glutamicum* (asd), or *Escherichia coli* K12 (asd) can be introduced into and expressed or overexpressed in a hydrogenotrophic microorganism (e.g., methanogen), thereby producing or overproducing exogenous aspartyl semialdehyde dehydrogenase or a functional fragment thereof. In certain embodiments, aspartyl semialdehyde dehydrogenase polypeptides for use in the compositions and methods disclosed herein are from *Corynebacterium glutamicum* ATCC 13032 (Genbank Accession No. CAA40504.1) or *E. coli* K12 (Genbank Accession No. CAA23511.1).

In certain embodiments, an aspartyl semialdehyde dehydrogenase amino acid sequence or a functional fragment thereof is based on the amino acid sequence of *Corynebacterium glutamicum* ATCC 13032 or *E. coli* K12 and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No CAA40504.1 or CAA23511.1, respectively, or a functional fragment thereof. In other embodiments, a recombinantly encoded aspartyl semialdehyde dehydrogenase has an amino acid sequence that is codon optimized for a host cell or is identical to a sequence as set forth in Genbank Accession Nos. CAA40504.1 or CAA23511.1, or comprises a consensus sequence of these aspartyl semialdehyde dehydrogenase or comprises a consensus sequence of a plurality of known aspartyl semialdehyde dehydrogenase polypeptides.

For example, to express or overproduce homoserine dehydrogenase, one or more genes from *Corynebacterium glutamicum* (hom), or *Methanococcus maripaludis* (hom) can be introduced into and expressed or overexpressed in a hydrogenotrophic microorganism (e.g., methanogen), thereby producing or overproducing exogenous homoserine dehydrogenase or a functional fragment thereof. In certain embodiments, homoserine dehydrogenase polypeptides for use in the compositions and methods disclosed herein are from *Corynebacterium glutamicum* ATCC 13032 (Genbank Accession No. BAB98576.1), *Methanococcus maripaludis* S2 (Genbank Accession No. CAF31258.1), *Methanocella conradii* HZ254 (Genbank Accession No. AFD00624.1), or *Methanobrevibacter ruminantium* M1 (Genbank Accession No. ADC46990.1).

In certain embodiments, a homoserine dehydrogenase amino acid sequence or a functional fragment thereof is based on the amino acid sequence of *Corynebacterium glutamicum* ATCC 13032 or *Methanococcus maripaludis* S2 and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. BAB98576.1 or CAF31258.1, respectively, or a functional fragment thereof. In other embodiments, a recombinantly encoded homoserine dehydrogenase has an amino acid sequence that is codon optimized for a host cell or is identical to a sequence as set forth in Genbank Accession Nos. BAB98576.1, CAF31258.1, AFD00624.1, or ADC46990.1, or comprises a consensus sequence of these homoserine dehydrogenases or comprises a consensus sequence of a plurality of known homoserine dehydrogenase polypeptides.

For example, to express or overproduce homoserine O-acetyltransferase, one or more genes from *Corynebacterium glutamicum* (metX), or *Methanothermobacter thermautotrophicus* (metX) can be introduced into and expressed or overexpressed in a hydrogenotrophic microorganism (e.g., methanogen), thereby producing or overproducing exogenous homoserine O-acetyltransferase or a functional fragment thereof. In certain embodiments, homoserine O-acetyltransferase polypeptides for use in the compositions and methods disclosed herein are from *Corynebacterium glutamicum* ATCC 13032 (Genbank Accession No. AAC06035.1) or *Methanothermobacter thermautotrophicus* ATCC 29096 (Genbank Accession No. AAB86286.1).

In certain embodiments, a homoserine O-acetyltransferase amino acid sequence or a functional fragment thereof is based on the amino acid sequence of *Corynebacterium glutamicum* ATCC 13032 or *Methanothermobacter thermautotrophicus* and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. AAC06035.1 or AAB86286.1, respectively, or a functional fragment thereof. In other embodiments, a recombinantly encoded homoserine O-acetyltransferase has an amino acid sequence that is codon optimized for a host cell or is identical to a sequence as set forth in Genbank Accession Nos. AAC06035.1 or AAB86286.1, or comprises a consensus sequence of these homoserine O-acetyltransferase or comprises a consensus sequence of a plurality of known homoserine O-acetyltransferase polypeptides.

For example, to express or overproduce homoserine O-succinyltransferase, one or more genes from *Escherichia coli* (metA), or *Campylobacter jejuni* (metA) can be introduced into and expressed or overexpressed in a hydrogenotrophic microorganism (e.g., methanogen), thereby producing or overproducing exogenous homoserine O-succinyltransferase or a functional fragment thereof. In certain embodiments, homoserine O-succinyltransferase polypeptides for use in the compositions and methods disclosed herein are from *Escherichia coli* strain K12 (Genbank Accession No. CAA32654.1) or *Campylobacter jejuni* strain NCTC 11168 (Genbank Accession No. CAL35820.1).

In certain embodiments, a homoserine O-succinyltransferase amino acid sequence or a functional fragment thereof is based on the amino acid sequence of *Corynebacterium glutamicum* ATCC 13032 or *Methanococcus maripaludis* S2 and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. BAB98576.1 or CAF31258.1, respectively, or a functional fragment thereof. In other embodiments, a recombinantly encoded homoserine O-succinyltransferase has an amino acid sequence that is codon optimized for a host cell or is identical to a sequence as set forth in Genbank Accession Nos. BAB98576.1, CAF31258.1, AFD00624.1, or ADC46990.1, or comprises a consensus sequence of these homoserine O-succinyltransferase or comprises a consensus sequence of a plurality of known homoserine O-succinyltransferase polypeptides.

For example, to express or overproduce O-succinylhomoserine lyase, one or more genes from *Escherichia coli* (metB), or *Helicobacter pylori* (metB) can be introduced into and expressed or overexpressed in a hydrogenotrophic microorganism (e.g., methanogen), thereby producing or overproducing exogenous O-succinylhomoserine lyase or a functional fragment thereof. In certain embodiments, O-succinylhomoserine lyase polypeptides for use in the compositions and methods disclosed herein are from *Escherichia coli* strain K12 (Genbank Accession No. AAA24167.1) or *Helicobacter pylori* strain ATCC 700392 (Genbank Accession No. AAD07176.1).

In certain embodiments, a O-succinylhomoserine lyase amino acid sequence or a functional fragment thereof is based on the amino acid sequence of *Escherichia coli* or *Helicobacter pylori* and is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. AAA24167.1 or AAD07176.1, respectively, or a functional fragment thereof. In other embodiments, a recombinantly encoded O-succinylhomoserine lyase has an amino acid sequence that is codon optimized for a host cell or is identical to a sequence as set forth in Genbank Accession Nos. AAA24167.1 or AAD07176.1, or comprises a consensus sequence of these O-succinylhomoserine lyase or comprises a consensus sequence of a plurality of known O-succinylhomoserine lyase polypeptides.

For example, to express or overproduce cystathionine β-lyase, one or more genes from *Corynebacterium glutamicum* (metC), or *Escherichia coli* (metC) can be introduced into and expressed or overexpressed in a hydrogenotrophic microorganism (e.g., methanogen), thereby producing or overproducing exogenous cystathionine β-lyase or a functional fragment thereof. In certain embodiments, cystathionine β-lyase polypeptides for use in the compositions and methods disclosed herein are from *Corynebacterium glutamicum* (Genbank Accession No. AAK69425.1) or *Escherichia coli* (Genbank Accession No. AAA24158.1).

In certain embodiments, a cystathionine β-lyase amino acid sequence or a functional fragment thereof is based on the amino acid sequence of *Corynebacterium glutamicum* or *Escherichia coli* and at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. AAK69425.1 or AAA24158.1, respectively, or a functional fragment thereof. In other embodiments, a recombinantly encoded cystathionine β-lyase has an amino acid sequence that is codon optimized for a host cell or is identical to a sequence as set forth in Genbank Accession Nos. AAK69425.1 or AAA24158.1, or comprises a consensus sequence of these cystathionine β-lyase or comprises a consensus sequence of a plurality of known cystathionine β-lyase polypeptides.

In certain embodiments, a hydrogenotrophic microorganism may directly incorporate a sulfur source, such as $H_2S$, directly into the methionine biosynthetic pathway. Any sulfide that is produced or is present for use by a hydrogenotrophic microorganism can enter the homocysteine biosynthesis pathway wherein O-acetylhomoserine sulfhydrylase incorporates $H_2S$ into O-acetylhomoserine to produce homocysteine, which can be further converted into methionine by methionine synthase (cobalamin dependent or independent).

For example, hydrogenotrophic microorganisms as described herein may be engineered to express or overproduce O-acetylhomoserine sulfhydrylase (EC 2.5.1.49), which can incorporate $H_2S$ into O-acetyl-homoserine to produce homocysteine, and optionally engineered to express or overproduce cobalimin-dependent methionine synthase (EC 2.1.1.13) or cobalimin-independent methionine synthase (also known as homocysteine methyltransferase) (EC 2.1.1.14) to convert homocysteine into methionine.

To express or overproduce O-acetylhomoserine sulfhydrylase, one or more genes based on those from *Methanocella conradii* or *Methanobrevibacter ruminantium* can be introduced into and expressed or overexpressed in a hydrogenotrophic microorganism (e.g., non-natural or recombinant methanogen) of this disclosure, thereby producing or overproducing exogenous O-acetylhomoserine sulfhydrylase or a functional fragment thereof. In certain embodiments, O-acetylhomoserine sulfhydrylase polypeptides for use in the compositions and methods disclosed herein may be from *Methanocella conradii* HZ254 (Genbank Accession No. AFD00350.1), *Methanobrevibacter ruminantium* M1 (Genbank Accession No. ADC47419.1 or ADC46998.1), *Clostridium difficile* T19 (Genbank Accession No. ERM48664.1), *Clostridium botulinum* A str. ATCC 3502 (Genbank Accession No. CAL83417.1), *Leptospira meyeri* (Genbank Accession No. P94890.1), or *Rhodobacter sphaeroides* 2.4.1 (Genbank Accession No. YP_351901.2).

In certain embodiments, an O-acetylhomoserine sulfhydrylase amino acid sequence or a functional fragment thereof is based on the amino acid sequence of *Methanocella conradii* HZ254 or *Methanobrevibacter ruminantium* M1 and at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. AFD00350.1 or ADC47419.1, respectively, or a functional fragment thereof. In other embodiments, a recombinantly encoded O-acetylhomoserine sulfhydrylase has an amino acid sequence that is codon optimized for a host cell or is identical to a sequence as set forth in Genbank Accession Nos. AFD00350.1, ADC47419.1, ADC46998.1, CCL83415.1, or CAL83417.1, or comprises a consensus sequence of these O-acetylhomoserine sulfhydrylases or comprises a consensus sequence of a plurality of known O-acetylhomoserine sulfhydrylase polypeptides.

In any of the aforementioned O-acetylhomoserine sulfhydrylase, a non-natural or recombinant hydrogenotrophic microorganism is further engineered to express, overexpress, or overproduce a homoserine O-acetyltransferase, as described herein.

In further embodiments, hydrogenotrophic microorganisms as described herein may be engineered to express or overproduce cobalamin-dependent methionine synthase (EC 2.1.1.13) or cobalamin-independent methionine synthase (also known as homocysteine methyltransferase) (EC 2.1.1.14), and optionally engineered to also express or overproduce O-acetylhomoserine sulfhydrylase.

For example, to express or overproduce cobalamin-dependent methionine synthase, one or more genes from *Escherichia coli* (metH), *Corynebacterium glutamicum* (metH), or *Clostridium difficile* can be introduced into and expressed or overexpressed in a hydrogenotrophic microorganism (e.g., non-natural methanotroph bacteria), thereby producing or overproducing exogenous cobalamin-dependent methionine synthase or a functional fragment thereof. In certain embodiments, cobalamin-dependent methionine synthase polypeptides for use in the compositions and methods disclosed herein are from *Escherichia coli* K-12 substrain MG1655 (Genbank Accession No. AAC76832.1), *Corynebacterium glutamicum* ATCC 13032 (Genbank Accession No. BAB98900.1), *Clostridium difficile* F665 (Genbank Accession No. ERM51559.1), or *Psuedomonas putida* GB-1 (Genbank Accession No. ABY97885.1).

In certain embodiments, a cobalamin-dependent methionine synthase amino acid sequence or a functional fragment thereof is based on the amino acid sequence of *Corynebacterium glutamicum* ATCC 13032 and at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. BAB98900.1, or a functional fragment thereof. In other embodiments, a recombinantly encoded cobalamin-dependent methionine synthase has an amino acid sequence that is codon optimized for a host cell or is identical to a sequence as set forth in Genbank Accession Nos. AAC76832.1, BAB98900.1, ERM51559.1, or ABY97885.1, or comprises a consensus sequence of these cobalamin-dependent methionine synthases or comprises a consensus sequence of a plurality of known cobalamin-dependent methionine synthase polypeptides.

In other embodiments, for example, to express or overproduce methionine synthase, one or more genes from *Escherichia coli* (metE or metB12), *Corynebacterium glutamicum* (metE), or *Methanococcus maripaludis* (metE) can be introduced into and expressed or overexpressed in a hydrogenotrophic microorganism (e.g., non-natural or recombinant methanogen), thereby producing or overproducing exogenous cobalamin-independent methionine synthase or a functional fragment thereof. In certain embodiments, cobalamin-independent methionine synthase polypeptides for use in the compositions and methods disclosed herein are from *Escherichia coli* K-12 substrain MG1655 (Genbank Accession No. AAC76832.1), *Corynebacterium glutamicum* ATCC 13032 (Genbank Accession No. CAF19845.1), *Methanococcus maripaludis* S2 (Genbank Accession No. NP_987521.1), *Methanocella conradii* HZ254 (Genbank Accession No. AFD00421.1), or *Methanobrevibacter ruminantium* M1 (Genbank Accession No. ADC47470.1).

In certain embodiments, a cobalamin-independent methionine synthase amino acid sequence or a functional fragment thereof is based on the amino acid sequence of *Methanococcus maripaludis* S2 or *Methanobrevibacter ruminantium* M1 and at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. NP_987521.1 or ADC47470.1, respectively, or a functional fragment thereof. In other embodiments, a recombinantly encoded cobalamin-independent methionine synthase has an amino acid sequence that is codon optimized for a host cell or is identical to a sequence as set forth in Genbank Accession Nos. AAC76832.1, CAF19845.1, NP_987521.1, AFD00421.1, or ADC47470.1, or comprises a consensus sequence of these cobalamin-independent methionine synthases or comprises a consensus sequence of a plurality of known cobalamin-independent methionine synthase polypeptides.

In any of the aforementioned methyl transferase embodiments, a non-natural or recombinant hydrogenotrophic microorganism is further engineered to express, overexpress, or overproduce an O-acetylhomoserine sulfhydrylase, as described herein.

In any of the aforementioned non-natural or recombinant hydrogenotrophic microorganism embodiments, the present disclosure provides hydrogenotrophic microorganisms that are methanogenic archaea, such as *Methanobacterium, Methanobrevibacter, Methanocalculus, Methanocaldococcus, Methanocella, Methanococcus, Methanococcoides, Methanocorpusculum, Methanoculleus, Methanofollis, Methanogenium, Methanohalobium, Methanohalophilus, Methanolacinia, Methanolobus, Methanomethylovorans, Methanomicrobium, Methanomicrococcus, Methanoplanus, Methanopyrus, Methanoregula, Methanosaeta, Methanosalsum, Methanosarcina, Methanosphaera, Methanospirillium, Methanothermobacter, Methanothermococcus, Methanothermus*, or *Methanotorris.*

In any of the aforementioned non-natural or recombinant hydrogenotrophic microorganism embodiments, the present disclosure provides hydrogenotrophic microorganisms that are a particular methanogenic archaea species. Exemplary methanogenic archaea species, such as *Methanobacterium alcaliphilum, Methanobacterium bryantii, Methanobacterium congolense, Methanobacterium defluvii, Methanobacterium espanolae, Methanobacterium formicicum, Methanobacterium ivanovii, Methanobacterium palustre, Methanobacterium thermaggregans, Methanobacterium uliginosum, Methanobrevibacter acididurans, Methanobrevibacter arboriphilicus, Methanobrevibacter gottschalkii, Methanobrevibacter olleyae, Methanobrevibacter ruminantium, Methanobrevibacter smithii, Methanobrevibacter woesei, Methanobrevibacter wolinii, Methanocella arvoryzae, Methanocella conradii, Methanocella paludicola, Methanothermobacter marburgensis, Methanothermobacter thermautotrophicum, Methanothermobacter thermoflexus, Methanothermobacter thermophilus, Methanothermobacter wolfeii, Methanothermus sociabilis, Methanocorpusculum bavaricum, Methanocorpusculum parvum, Methanoculleus chikuoensis, Methanoculleus submarinus, Methanogenium frigidum, Methanogenium liminatans, Methanogenium marinum, Methanomicrococcus blatticola, Methanoplanus endosymbiosus, Methanoplanus limicola, Methanoplanus petrolearius, Methanopyrus kandleri, Methanoregula boonei, Methanosaeta concilii, Methanosaeta harundinacea, Methanosaeta pelagica, Methanosaeta thermophila, Methanosarcina acetivorans, Methanosarcina barkeri, Methanosarcina mazei, Methanosarcina thermophila, Methanomicrobium mobile, Methanococcus aeolicus, Methanococcus maripaludis, Methanococcus vannielii, Methanococcus voltae, Methanothermococcus thermolithotrophicus, Methanopyrus kandleri, Methanothermobacter thermoautotroiphicus, Methanocaldococcus fervens, Methanocaldococcus indicus, Methanocaldococcus infernus, Methanocaldococcus jannaschii*, and *Methanocaldococcus vulcanius.*

In any of the aforementioned non-natural or recombinant hydrogenotrophic microorganism embodiments, the present disclosure provides hydrogenotrophic microorganisms comprising methanogenic archaea that produce cytochromes or do not produce cytochromes. Exemplary methanogenic archaea that do not produce cytochromes include *Methanococcus maripaludis* or *Methanococcus vannielii*. An exemplary methanogenic archaea that does produce cytochromes is *Methanosarcina barkeri* or *Methanosarcina mazei.*

$H_2/CO_x$ Substrate

Hydrogen production involves a series of reforming, conditioning and separation steps wherein several of those steps (e.g., steam reforming, autothermal reforming, high temperature shift, low temperature shift, $CO_2$ scrubbing and pressure swing absorption) can provide a feedstock that by itself or in combination with one or more other gas streams can provide an $H_2/CO_x$ substrate useful as a feedstock for hydrogenotrophic microorganisms and methods of this disclosure. In certain embodiments, microorganisms of the disclosure can utilize a $CO_x$ substrate, optionally in the presence of $H_2$.

By way of background, hydrogen production may involve single step or multistep reforming, partial oxidation or gasification to produce a $H_2/CO_x$ substrate such as syngas, combined with a high temperature water gas shift (HTS) reaction, a low temperature water gas shift (LTS) reaction, or both. In some methods, carbon oxides are removed by using pressure swing adsorption (PSA) with molecular sieves, which separates a substantially pure hydrogen ($H_2$) gas stream from a tail gas comprising some residual $H_2$ gas along with various amounts of carbon dioxide ($CO_2$), carbon monoxide (CO), and methane ($CH_4$). In certain embodiments, carbon dioxide may be optionally scrubbed before subjecting the gas (e.g., syngas) to PSA. Depending on the syngas production process used and whether carbon dioxide is scrubbed, a tail gas will include different ratios of $H_2$, $CO_2$, CO, and $CH_4$. In some embodiments, a $H_2/CO_x$ substrate for use in the methods of this disclosure is a gas stream blend comprising a mixture of PSA tail gas and $H_2$ gas.

For example, methane steam reforming combined with HTS will produce a gas stream having mostly $H_2$ (about 75%) and $CO_2$ (about 20%), with some $CH_4$ (about 5%) and very little or no CO. In another example, methane steam reforming combined with LTS will produce a gas stream having mostly $H_2$ (about 75%) and CO (about 10%), with some $CO_2$ (about 5%) and $CH_4$ (about 1%). In still another example, methane steam reforming combined with HTS and PSA will produce a tail gas having mostly $H_2$ (about 30%) and $CO_2$ (about 45%), with a fair amount of CO (about 10%) and $CH_4$ (about 15%). In this last embodiment, if a $CO_2$ scrubbing step is included, then the tail gas will comprise mostly $H_2$ (about 50%), $CH_4$ (about 30%) and CO (about 20%), with little $CO_2$ (about 1%). In certain embodiments, the PSA tail gas is mixed with the pipeline $H_2$ produced from PSA to produce a $H_2/CO_x$ substrate of interest, such as a $H_2/CO_x$ substrate having a $H_2$:$CO_2$ ratio of about 5:1, 4:1, 3:1, 2:1 or 1:1.

Steam reforming of methane can provide a feedstock ratio of $CO_2$ to $H_2$ that ranges from about 1:7 to about 1:15, respectively, wherein other components may include CO, $CH_4$ and $H_2O$. Alternatively, methane may be reformed with $CO_2$, which is called dry reforming. Dry reforming of methane can provide a feedstock ratio of $CO_2$ to $H_2$ that ranges from about 1:5 to about 1:15, respectively, wherein other components may include CO, $CH_4$, and $H_2O$.

Partial oxidation (catalytic or non-catalytic) and autothermal reforming use oxygen as a co-reactant to natural gas instead of water. Partial oxidation and autothermal reforming can provide a feedstock ratio of $CO_2$ to $H_2$ that is about 1:20, wherein other components may include CO, $CH_4$, and $H_2O$.

Gasification, the partial oxidation of carbon containing material with air or oxygen (e.g., natural gas liquids, naphtha, bitumen, coal, biomass, or the like), can provide a $H_2/CO_x$ feedstock for use with the hydrogenotrophic microorganisms and methods of this disclosure. For example, the gasification of coal provides a feedstock ratio of $CO_2$ to $H_2$ that ranges from about 1:1.1 to about 1:11, respectively, wherein other components may include CO, $CH_4$, $N_2$, and $H_2O$.

Ammonia synthesis involves series of reforming and conditioning steps, wherein four (steam reforming, autothermal reforming, high temperature shift, low temperature shift) of those steps can provide a $H_2/CO_x$ feedstock for use with the hydrogenotrophic microorganisms and methods of this disclosure. For each of these different processes, a feedstock ratio of $CO_2$ to $H_2$ that ranges from about 1:3 to about 1:10, respectively, is provided, wherein other components may include CO, $CH_4$, $N_2$, and $H_2O$.

Methanol synthesis involves the steps of low temperature reforming, steam reforming, and autothermal reforming, all of which can provide a $H_2/CO_x$ feedstock for use with the hydrogenotrophic microorganisms and methods of this disclosure. For each of these three processes, a feedstock ratio of $CO_2$ to $H_2$ that ranges from about 1:7 to about 1:12, respectively, is produced, wherein other components may include CO, $CH_4$, and $H_2O$.

An integrated steel mill combines various processes, including a coke oven (to make coke from coal), a blast furnace (to make pig iron) and an oxygen furnace (to make steel). In certain embodiments, direct reduction in an integrated steel mill uses reformed natural gas as a reductant (instead of coke) to make pig iron. Each of these ovens, as well as direct reduction reforming (which produces top gas), can produce a feedstock ratio of $CO_2$ to $H_2$ that ranges from about 8:1 (from blast or oxygen furnace) to about 1:32 (from coke oven), respectively, wherein other components may include CO, $CH_4$, $C_2H_6$, $C_3H_8$, $N_2$, and $H_2O$.

In any of the aforementioned sources of $H_2/CO_x$ substrate, a $H_2/CO_x$ feedstock so produced can be mixed any other produced $H_2/CO_x$ feedstock or with $H_2$, $CO_2$, CO or any combination thereof to produce a $H_2/CO_x$ substrate of interest, such as a substrate having a $H_2$:$CO_2$ ratio of about 4:1 or 3:1. In certain embodiments, a $H_2/CO_x$ substrate for use with, for example, methanogens, comprises a $H_2$:$CO_2$ ratio of about 5:1, 4:1, 3:1, 2:1 or 1:1, and optionally the total amount of CO is no more than about 0.1%, 0.2%, 0.3%, 0.4%, 0.5%, 0.6%, 0.7%, 0.9%, 0.9%, 1.0%, 2.0%, 3.0%, 4.0%, 5.0%, 6.0%, 7.0%, 8.0%, 9.0%, 10%, 11%, 12%, 13%, 14%, 15%, or 20%. In other embodiments, a $H_2/CO_x$ substrate for use with, for example, *Clostridium*, comprises a $H_2$:($CO_2$+CO) ratio of about 5:1, 4:1, 3:1, 2:1, or 1:1, and optionally the total amount of CO is at least about 1.0%, 5.0%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more. In any of these embodiments, the $H_2/CO_x$ substrate may comprise a blend of PSA tail gas with $H_2$ gas.

In any of the aforementioned non-natural or recombinant hydrogenotrophic microorganism embodiments, the present disclosure provides hydrogenotrophic microorganisms that utilize, metabolize, oxidize, or convert a $H_2/CO_x$ substrate comprised of $H_2$ with $CO_2$ or CO or both, and optionally various other components as described herein. In certain embodiments, a $H_2/CO_x$ substrate is $H_2$, $CO_2$ and CO, wherein there is more CO than $CO_2$, optionally with various other components as described herein. In further embodiments, a $H_2/CO_x$ substrate is $H_2$, $CO_2$ and CO, wherein there is more $CO_2$ than CO, optionally with various other components as described herein. In yet further embodiments, a $H_2/CO_x$ substrate is $H_2$, $CO_2$ and CO wherein there is more CO than both $CO_2$ and $H_2$, optionally with various other components as described herein. In certain circumstances, a microorganism that metabolizes $H_2/CO_x$ may use the $H_2$ as an energy source and the $CO_x$, wherein x is 1 or 2, as a carbon source, or use $H_2$ and $CO_x$ as an energy source, and $CO_x$ as a carbon source.

In any of the aforementioned non-natural or recombinant hydrogenotrophic microorganism embodiments, the present disclosure provides a $H_2/CO_x$ substrate that can be produced, for example, by steam reforming, dry reforming, autothermal reforming, catalytic partial oxidation or partial oxidation of natural gas or liquid hydrocarbons (e.g., ethane, propane, naphtha), within hydrogen production, within ammonia synthesis, within methanol synthesis, by steelmaking, or by gasification of coal, naphtha, resid, biomass or waste. In certain embodiments, a $H_2/CO_x$ substrate produced by any of the aforementioned reforming methods can be further conditioned by a water-gas shift reaction. In addition, one or more gas streams produced by any of the aforementioned methods can be blended with other sources of hydrogen, carbon monoxide or carbon dioxide to produce or make a $H_2/CO_x$ substrate, including pipeline hydrogen, pipeline carbon dioxide, carbon dioxide scrubber off-gas, flue gas, ethane cracker off-gas, reformer off-gas or chlorine synthesis off-gas. In some embodiments, the feedstock ratio of $CO_2$ to $H_2$ ranges from about 1:50 to about 10:1, respectively. In further embodiments, the feedstock ratio of $CO_2$ to $H_2$ ranges from about 1:3 to about 1:5, respectively.

Culture Methods

A variety of culture methodologies may be used for non-natural or recombinant hydrogenotrophic microorganisms (e.g., bacteria, methanogenic archaea) described herein. For example, hydrogenotrophic microorganisms may be grown by batch culture or continuous culture methodologies. In certain embodiments, cultures are grown in a controlled culture unit, such as a fermenter, bioreactor, hollow fiber membrane bioreactor, bubble column bioreactor, trickle bed bioreactor, or the like.

A classical batch culturing method is a closed system where the composition of the media is set at the beginning of the culture and not subject to external alterations during the culture process. Thus, at the beginning of the culturing process, the media is inoculated with the desired hydrogenotrophic microorganism (e.g., methanogen) and growth or metabolic activity is permitted to occur without adding anything to the system. Generally, a "batch" culture is batch with respect to the addition of carbon source, gas feedstock and media components, wherein waste gasses are allowed to exit, and attempts are often made at controlling other factors, such as pH. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

A Fed-Batch system is a variation on the standard batch system. Fed-Batch culture processes comprise a batch system with the modification that a substrate and potentially media components are added in increments as the culture progresses. Fed-Batch systems are useful when catabolite repression is apt to inhibit the metabolism of the cells and where it is desirable to have limited amounts of substrate in the media. In gas substrate fermentations, a system is continuous with respect to gas substrate (since waste gas can be removed) and Fed-batch with respect to liquid (media). Batch and Fed-Batch culturing methods are common and known in the art (see, e.g., Thomas D. Brock, Biotechnology: A Textbook of Industrial Microbiology, $2^{nd}$ Ed. (1989)

Sinauer Associates, Inc., Sunderland, Mass.; Deshpande, *Appl. Biochem. Biotechnol.* 36:227, 1992).

Continuous cultures are "open" systems where a defined culture media is added continuously to a bioreactor and an equal amount of conditioned media is removed simultaneously (with or without biomass or cell retention) for processing. Continuous cultures generally maintain the cells at a constant high liquid phase density where cells are primarily in logarithmic phase growth. Alternatively, continuous culture may involve biomass, cell retention or cell immobilization where feedstock and nutrients are continuously added and valuable products, by-products, and waste products can be continuously removed from the cell mass. Cell retention may be performed by a variety of methods, such as by filtration, centrifugation or settling. Cell immobilization may be performed using a wide range of solid supports composed of natural and/or synthetic materials.

Continuous or semi-continuous culture allows for the modulation of one factor or any number of factors that affect cell growth or end product concentration. For example, one method can maintain a limited nutrient (e.g., carbon source, nitrogen level, hydrogen level, phosphorous level) at a fixed rate and allow all other parameters to modulate. In other systems, a number of factors affecting growth can be altered continuously while the cell concentration, measured by media turbidity, is kept constant. In certain embodiments, hydrogenotrophic biomass growth is limited to increase product to biomass ratio. Methods of modulating nutrients and growth factors for continuous culture processes, as well as techniques for maximizing the rate of product formation, are well known in the art (see Brock, 1989).

Liquid phase bioreactors (e.g., stirred tank, packed bed, one liquid phase, two liquid phase, hollow fiber membrane) are well known in the art and may be used for growth of hydrogenotrophic microorganisms.

Multiphase bioreactors may be used in the methods of the instant disclosure (e.g., bubble column reactor, trickle bed reactor (fixed or packed bed), fluidized bed reactor). Bubble columns are the devices in which gas, in the form of bubbles, come in contact with the liquid. Trickle bed reactors use co-current or countercurrent flow of gas and liquid to grow cultures. A fluidized bed reactor comprises passing a fluid (gas or liquid) through a granular solid material at high enough velocities to suspend the solid and cause it to behave as though it were a fluid. One purpose of multiphase bioreactors is to mix the liquid and gas phases, wherein the gas is consumed by hydrogenotrophic microorganisms to a greater or lesser extent depending on the intensity of mass transfer and chemical reaction. Various types of multiphase bioreactors are well known in the art and may be used for growth of hydrogenotrophic microorganisms in the methods of the instant disclosure.

Hydrogenotrophic microorganisms described in the present disclosure may be grown as an isolated pure culture, with a heterologous non-hydrogenotrophic microorganism(s) that may aid with growth, or combined with one or more different strains or species of hydrogenotrophic microorganisms to generate a mixed culture.

In other aspects, this disclosure provides a method for producing methionine or a methionine-containing feed additive, comprising culturing any of the aforementioned non-natural or recombinant hydrogenotrophic microorganisms for a time sufficient to produce methionine, wherein the non-natural or recombinant hydrogenotrophic microorganism: (a) expresses one or more sulfur assimilation polypeptides having increased activity as compared to a parent hydrogenotrophic microorganism; (b) overexpresses one or more sulfur assimilation polypeptides; or (c) comprises altered regulation of one or more sulfur assimilation polypeptides, wherein the non-natural hydrogenotrophic microorganism produces methionine at a higher level than a parent hydrogenotrophic microorganism.

In certain embodiments, the present disclosure provides a process for making methionine or methionine-containing feed additive, comprising culturing a recombinant, methionine-excreting hydrogenotrophic microorganism of this disclosure in the presence of a $H_2/CO_x$ substrate under conditions and for a time sufficient to allow for expression of an exogenous polynucleotide encoding a polypeptide from sulfur assimilation polypeptides, wherein methionine is produced and accumulate in the culture medium at a higher level than the methionine produced by a parent hydrogenotrophic microorganism.

In any of the aforementioned methods, the hydrogenotrophic microorganisms can be cultured in a fermenter or bioreactor, such as a liquid phase, bubble column, or trickle bed bioreactor.

In any of the aforementioned methods for using non-natural or recombinant hydrogenotrophic microorganisms (e.g., methanogen) to produce methionine as disclosed herein, the gas feedstock is a $H_2/CO_x$ substrate, wherein the feedstock comprises $H_2$ with $CO_2$ or CO or both, and optionally various other components as described herein. In certain embodiments, a $H_2/CO_x$ substrate is syngas, such as syngas produced by steam reforming, dry reforming, autothermal reforming, catalytic partial oxidation or partial oxidation of natural gas or liquid hydrocarbons, conditioned by a water-gas shift reaction, by ammonia synthesis, by methanol synthesis, by steelmaking, or by gasification of coal, biomass or waste.

In any of the aforementioned methods for using non-natural or recombinant hydrogenotrophic microorganisms (e.g., methanogen) to produce methionine as disclosed herein, a gas substrate is a $H_2/CO_x$ substrate, which can be produced, for example, by steam reforming, dry reforming, autothermal reforming, catalytic partial oxidation or partial oxidation of natural gas or light hydrocarbons (e.g., ethane, propane, naphtha), conditioned by a water-gas shift reaction, within hydrogen production, within ammonia synthesis, within methanol synthesis, by steelmaking, or by gasification of coal, naphtha, resid, biomass or waste. In certain embodiments, a $H_2/CO_x$ substrate is a blend of any gas stream so produced with one or more other sources of hydrogen, carbon monoxide, carbon dioxide or any combination thereof, including pipeline hydrogen, pipeline carbon dioxide, carbon dioxide scrubber off-gas, flue gas, ethane cracker off-gas, reformer off-gas chlorine synthesis off-gas, or any combination thereof.

In any of the aforementioned methods for using non-natural or recombinant hydrogenotrophic microorganisms (e.g., methanogen) to produce methionine as disclosed herein, the hydrogenotrophic microorganisms being cultured are methanogenic archaea, such as *Methanobacterium, Methanobrevibacter, Methanocalculus, Methanocaldococcus, Methanocella, Methanococcus, Methanococcoides, Methanocorpusculum, Methanoculleus, Methanofollis, Methanogenium, Methanohalobium, Methanohalophilus, Methanolacinia, Methanolobus, Methanomethylovorans, Methanomicrobium, Methanomicrococcus, Methanoplanus, Methanopyrus, Methanoregula, Methanosaeta, Methanosalsum, Methanosarcina, Methanosphaera, Methanospirillium, Methanothermobacter, Methanothermococcus, Methanothermus*, or *Methanotorris.*

In certain embodiments, the non-natural or recombinant hydrogenotrophic microorganism may be a *Methanobacterium alcaliphilum, Methanobacterium bryantii, Methanobacterium congolense, Methanobacterium defluvii, Methanobacterium espanolae, Methanobacterium formicicum, Methanobacterium ivanovii, Methanobacterium palustre, Methanobacterium thermaggregans, Methanobacterium uliginosum, Methanobrevibacter acididurans, Methanobrevibacter arboriphilicus, Methanobrevibacter gottschalkii, Methanobrevibacter olleyae, Methanobrevibacter ruminantium, Methanobrevibacter smithii, Methanobrevibacter woesei, Methanobrevibacter wolinii, Methanocella arvoryzae, Methanocella conradii, Methanocella paludicola, Methanothermobacter marburgensis, Methanothermobacter thermautotrophicum, Methanothermobacter thermoflexus, Methanothermobacter thermophilus, Methanothermobacter wolfeii, Methanothermus sociabilis, Methanocorpusculum bavaricum, Methanocorpusculum parvum, Methanoculleus chikuoensis, Methanoculleus submarinus, Methanogenium frigidum, Methanogenium liminatans, Methanogenium marinum, Methanomicrococcus blatticola, Methanoplanus endosymbiosus, Methanoplanus limicola, Methanoplanus petrolearius, Methanopyrus kandleri, Methanoregula boonei, Methanosaeta concilii, Methanosaeta harundinacea, Methanosaeta pelagica, Methanosaeta thermophila, Methanosarcina acetivorans, Methanosarcina barkeri, Methanosarcina mazei, Methanosarcina thermophila, Methanomicrobium mobile, Methanococcus aeolicus, Methanococcus maripaludis, Methanococcus vannielii, Methanococcus voltae, Methanothermococcus thermolithotrophicus, Methanopyrus kandleri, Methanothermobacter thermoautotroiphicus, Methanocaldococcus fervens, Methanocaldococcus indicus, Methanocaldococcus infernus, Methanocaldococcus jannaschii*, and *Methanocaldococcus vulcanius*.

In any of the aforementioned methods, a hydrogenotrophic microorganism is a mesophile, thermophile, hyperthermophile, or a combination thereof. In any of the aforementioned methods, a hydrogenotrophic microorganism is an obligate anaerobe or a facultative anaerobe. In any of the aforementioned methods, a hydrogenotrophic microorganism is an obligate hydrogenotroph or a facultative hydrogenotroph.

The hydrogenotrophic microorganism (e.g., methanogen) may be engineered to produce methionine at enhanced levels as compared to a parent microorganism. In certain embodiments, an engineered hydrogenotrophic microorganism of this disclosure produces methionine at a level that is at least about 10% greater than that produced by the parent hydrogenotrophic microorganism, or at least about 2-fold, about 3-fold, about 4-fold, about 5-fold, about 6-fold, about 7-fold, about 8-fold, about 9-fold, about 10-fold, about 15-fold, about 20-fold, about 30-fold, about 40-fold, about 50-fold, about 60-fold, about 70-fold, about 80-fold, about 90-fold, about 100-fold, about 500-fold, or about 1000-fold the level produced by the parent hydrogenotrophic microorganism, when cultured in the presence of a $CO_x$ substrate, optionally in the presence of $H_2$, under the same culture condition (e.g., serum tube or bioreactor). In other embodiments, an engineered hydrogenotrophic microorganism of this disclosure produces methionine at a level that is from at least about 15%, at least about 20%, at least about 25%, at least about 30%, at least about 35%, at least about 40%, at least about 45%, at least about 50%, at least 55%, at least about 60%, at least about 65%, at least about 70%, at least about 75%, at least about 80%, at least about 85%, at least about 90%, or is at least about 95% greater than that produced by the parent hydrogenotrophic microorganism under the same culture conditions.

In certain embodiments, methods for converting a $CO_x$ substrate, optionally in the presence of $H_2$, into methionine as provided herein will produce methionine at about 0.001 g/L of culture to about 500 g/L of culture. In some embodiments, the amount of methionine produced is about 1 g/L of culture to about 100 g/L of culture. In further embodiments, the amount of methionine produced is about 0.001 g/L, 0.01 g/L, 0.025 g/L, 0.05 g/L, 0.1 g/L, 0.15 g/L, 0.2 g/L, 0.25 g/L, 0.3 g/L, 0.4 g/L, 0.5 g/L, 0.6 g/L, 0.7 g/L, 0.8 g/L, 0.9 g/L, 1 g/L, 2.5 g/L, 5 g/L, 7.5 g/L, 10 g/L, 12.5 g/L, 15 g/L, 20 g/L, 25 g/L, 30 g/L, 35 g/L, 40 g/L, 45 g/L, 50 g/L, 60 g/L, 70 g/L, 80 g/L, 90 g/L, 100 g/L, 125 g/L, 150 g/L, 175 g/L, 200 g/L, 225 g/L, 250 g/L, 275 g/L, 300 g/L, 325 g/L, 350 g/L, 375 g/L, 400 g/L, 425 g/L, 450 g/L, 475 g/L, or 500 g/L.

In still further embodiments, methods for converting a $CO_x$ substrate, optionally in the presence of $H_2$, into methionine as provided herein will produce at least about or up to about 1 kilogram (kg), at least about or up to 10 kg, at least about or up to 100 kg, at least about or up to 1,000 kg, at least about or up to 10,000 kg, at least about or up to 50,000 kg, at least about or up to 100,000 kg, at least about or up to 250,000 kg, at least about or up to 500,000 kg, or more of methionine/day. In certain embodiments, methionine is produced at about 100,000 metric tons (MT) per year (i.e., 100 million kg per year or 300,000 kg/day), about 75,000 MT per year (or 225,000 kg/day), about 50,000 MT per year (or 150,000 kg/day), about 25,000 MT (or 75,000 kg/day), or about 10,000 MT per year (or 30,000 kg/day).

Systems for Making Methionine

In additional aspects, the present disclosure provides a system for producing methionine, comprising a source of gas comprising a $H_2/CO_x$ substrate; a bioreactor comprising any one or more of the aforementioned non-natural or recombinant hydrogenotrophic microorganisms that (a) expresses one or more sulfur assimilation polypeptides having increased activity as compared to a parent hydrogenotrophic microorganism; (b) overexpresses one or more sulfur assimilation polypeptides; or (c) comprises altered regulation of one or more sulfur assimilation polypeptides; and a connector disposed between the gas source and the bioreactor to allow flow of the gas into the bioreactor; wherein the non-natural hydrogenotrophic microorganism metabolizes the $H_2/CO_x$ substrate to overproduce one or more methionine pathway amino acids as compared to a parent hydrogenotrophic microorganism.

In any of the aforementioned systems, the $H_2/CO_x$ substrate is converted into a biological material, such as animal feed or a fertilizer. In certain embodiments, the $H_2/CO_x$ substrate is assimilated into a biological material enriched for methionine. In further embodiments, the resultant methionine is purified and used as animal feed, food additives or nutrient supplements. In still other embodiments, biomass enriched with methionine are used for animal feed, food additives or nutrient supplements.

In any of the aforementioned systems for using non-natural or recombinant hydrogenotrophic microorganisms (e.g., methanogen) to produce methionine as disclosed herein, the gas feedstock is a $H_2/CO_x$ substrate, wherein the feedstock comprises $H_2$ with $CO_2$ or CO or both, and optionally various other components as described herein. In certain embodiments, a $H_2/CO_x$ substrate is syngas, such as syngas produced by steam reforming, dry reforming, autothermal reforming, catalytic partial oxidation or partial oxidation of natural gas or light hydrocarbons (e.g., ethane, propane, naphtha), conditioned by a water-gas shift reaction, within ammonia synthesis, within methanol synthesis, by steelmaking, or by gasification of coal, naphtha, resid, biomass or waste. In certain embodiments, a $H_2/CO_x$ substrate is a blend of any gas stream so produced with one or more other sources of hydrogen, carbon monoxide, carbon dioxide or any combination thereof, including pipeline hydrogen, pipeline carbon dioxide, carbon dioxide scrubber off-gas, flue gas, ethane cracker off-gas, reformer off-gas chlorine synthesis off-gas, or any combination thereof.

In any of the aforementioned systems for using non-natural or recombinant hydrogenotrophic microorganisms (e.g., methanogen) to produce methionine as disclosed herein, the hydrogenotrophic microorganisms being cultured are methanogenic archaea, such as *Methanobacterium, Methanobrevibacter, Methanocalculus, Methanocaldococcus, Methanocella, Methanococcus, Methanococcoides, Methanocorpusculum, Methanoculleus, Methanofollis, Methanogenium, Methanohalobium, Methanohalophilus, Methanolacinia, Methanolobus, Methanomethylovorans, Methanomicrobium, Methanomicrococcus, Methanoplanus, Methanopyrus, Methanoregula, Methanosaeta, Methanosalsum, Methanosarcina, Methanosphaera, Methanospirillium, Methanothermobacter, Methanothermococcus, Methanothermus*, or *Methanotorris.*

In certain embodiments, the non-natural or recombinant hydrogenotrophic microorganism may be a *Methanobacterium alcaliphilum, Methanobacterium bryantii, Methanobacterium congolense, Methanobacterium defluvii, Methanobacterium espanolae, Methanobacterium formicicum, Methanobacterium ivanovii, Methanobacterium palustre, Methanobacterium thermaggregans, Methanobacterium uliginosum, Methanobrevibacter acididurans, Methanobrevibacter arboriphilicus, Methanobrevibacter gottschalkii, Methanobrevibacter olleyae, Methanobrevibacter ruminantium, Methanobrevibacter smithii, Methanobrevibacter woesei, Methanobrevibacter wolinii, Methanocella arvoryzae, Methanocella conradii, Methanocella paludicola, Methanothermobacter marburgensis, Methanothermobacter thermautotrophicum, Methanothermobacter thermoflexus, Methanothermobacter thermophilus, Methanothermobacter wolfeii, Methanothermus sociabilis, Methanocorpusculum bavaricum, Methanocorpusculum parvum, Methanoculleus chikuoensis, Methanoculleus submarinus, Methanogenium frigidum, Methanogenium liminatans, Methanogenium marinum, Methanomicrococcus blatticola, Methanoplanus endosymbiosus, Methanoplanus limicola, Methanoplanus petrolearius, Methanopyrus kandleri, Methanoregula boonei, Methanosaeta concilii, Methanosaeta harundinacea, Methanosaeta pelagica, Methanosaeta thermophila, Methanosarcina acetivorans, Methanosarcina barkeri, Methanosarcina mazei, Methanosarcina thermophila, Methanomicrobium mobile, Methanococcus aeolicus, Methanococcus maripaludis, Methanococcus vannielii, Methanococcus voltae, Methanothermococcus thermolithotrophicus, Methanopyrus kandleri, Methanothermobacter thermoautotroiphicus, Methanocaldococcus fervens, Methanocaldococcus indicus, Methanocaldococcus infernus, Methanocaldococcus jannaschii*, and *Methanocaldococcus vulcanius.*

In any of the aforementioned systems, a hydrogenotrophic microorganism is a mesophile, thermophile, hyperthermophile, or a combination thereof. In any of the aforementioned methods, a hydrogenotrophic microorganism is an obligate anaerobe or a facultative anaerobe. In any of the aforementioned methods, a hydrogenotrophic microorganism is an obligate hydrogenotroph or a facultative hydrogenotroph.

EXAMPLES

Example 1

Production of Ethionine-Resistant Mutants of *Methanococcus maripaludis*

Methionine production is highly regulated in microorganisms, particularly by feedback inhibition. Exposing bacteria or archaea to a toxic methionine analog, such as DL-ethionine, will result in cells mutated in the methionine feedback inhibition, which are identified as those mutants capable of growing in the presence of the toxic analog (see, e.g., Kumar et al., *Biotechnology Advances* 23:41-61, 2005). Table 1 provides a list of organisms made along with their genetic background relative to wild-type, including some that were used in the experiments described herein.

TABLE 1

Modified *Methanococcus maripaludis* S2

| Strain | Relative Phenotype or Genotype |
|---|---|
| Trel 10 | Wild-type *Methanococcus mariapludis* S2 |
| Trel10-Mut333 | Trel 10 with feedback resistant aspartokinase (LysC) |
| Trel10-333UR | Trel10-Mut333 with upp:rep. Has approximately the same amino acid production as Trel10-Mut333. |
| Trel10-333UR-ΔdA | Trel10-333UR with a dapAdeletion. Requires lysine for growth |
| Trel10-333UR-ΔdA-er1.1 | Trel10-333UR-ΔdA ethionine resistant mutant 1.1 |
| Trel10-333UR-ΔdA-er3.1 | Trel10-333UR-ΔdA ethionine resistant mutant 3.1 |
| Trel10-333UR-ΔdA-er3.3 | Trel10-333UR-ΔdA ethionine resistant mutant 3.3 |
| Trel 9 | Wild-type *Methanosarcina mazei* C2A |
| Trel 42 | Wild-type *Methanosarcina acetivorans* C2A |
| Trel42-er1.1 | Trel142ethionine resistant mutant 1.1 |
| Trel42-er1.2 | Trel142ethionine resistant mutant 1.2 |
| Trel42-er1.3 | Trel142ethionine resistant mutant 1.3 |

Isolation of Ethionine Resistant *M. maripaludis* Mutants

To generate ethionine resistant mutants, Trel10-333UR-ΔdA (*M. maripaludis* S2 containing a lysine feedback resistant lysC and a dapA deletion, Table 1) was grown in 25 mL McCas media without Casamino acids supplemented with 100 mg/L of Lysine at 37° C. to an $OD_{600}$ of approximately 0.50 (see Sarmiento et al., *Methods Enzymol.* 494:44, 2011, which refers to the media McCV, and is used here without Casamino acids or yeast extract), then dispensed into two anaerobic Balch tubes (5 mL of culture each), and one tube received 0.3 mL mutagen ethyl methanesulfonate (EMS, 1:50 dilution in McCas no Cas) and the other tube received 0.3 mL McCas no Cas alone as a control. The tubes were pressurized with an 80/20 mix of $H_2/CO_2$ to 40 PSIG and incubated without shaking at 37° C. for one hour. After one hour of incubation, the pressure was released and 0.5 mL of the culture from each tube was removed and plated on McCas agar plates to determine the kill rate.

The remainder of the culture was washed to remove EMS, then spun down in a centrifuge at 1000 g for 15 minutes, the supernatant removed and the pelleted cells washed by resuspending in 1 mL McCas no Cas, and finally centrifuging again at 1000 g for 15 minutes. This wash was repeated 2× to remove EMS. After the final wash, the harvested cells were suspended in 500 μL McCas no Cas and 100 μl was transferred to three Balch tubes containing 5 mL of McCas no Cas+100 mg/L Lysine (for EMS treated) or one tube (control, untreated) for recovery. To each tube was added 0.1 mL 2.5% $Na_2S \times 9H_2O$ and then each tube was pressurized to 40 PSIG with 80/20 $H_2/CO_2$ and allowed to recover overnight at 37° C. The next morning, each culture was concentrated to 0.1 mL by centrifugation and plated on McCas no Cas plates containing 100 mg/L Lysine and 3 g/L ethionine. Plates were incubated in an Oxoid anaerobic jar with 10 PSIG of an 80/20 $H_2/CO_2$ gas mix at 37° C. The ethionine selection produced colonies that grew only from cultures that had been exposed to EMS. All work was carried out under anaerobic conditions unless otherwise stated.

Five colonies from individual plates were selected for HPLC analysis to measure methionine production. Briefly, *Methanococcus maripaludis* recombinants were grown in 5 mL of McCAS medium in a Balch tube, supplemented with puromycin (2.5 mg/L), gassed with $H_2:CO_2$ (4:1) to 40 psi at 37° C. with shaking overnight. On the second day, 100 μl of the overnight culture was used as seed culture to inoculate 5 ml minimal media (MM) in a Balch tube or 100 ml serum medium, gassed with $H_2:CO_2$ (4:1) to a pressure of 40 and 20 psi, respectively. The culture was placed at 37° C. with shaking for 72 hours; $H_2:CO_2$ (4:1) gas was refilled to the full pressure at the beginning of culture. After fermentation, 1.8 ml of culture was transferred to an Eppendorf tube, cells were removed at 12,000×g and the resultant supernatant was passed through 0.2 μm filter. The filtrate was analyzed by HPLC for amino acid content. As needed, the seed and fermentation media could be supplemented with puromycin (2.5 mg/L).

TABLE 2

Amino Acid Production by Mutant *M. maripaludis* in Serum Tubes

| Strain | Amino Acid (mg/L) | | | |
|---|---|---|---|---|
| | Glycine | Threonine | Lysine | Methionine |
| Trel 10 | 7 | 31 | ND | ND |
| Trel10-Mut333 | 208 | 24 | 22 | ND |
| Trel10-333UR | 149 | 10 | 12 | ND |
| Trel10-333UR-ΔdA | 166 | 17 | NA | 3 |
| Trel10-333UR-ΔdA-er1.1 | 219 | 32 | NA | 22 |
| Trel10-333UR-ΔdA-er3.1 | 175 | 22 | NA | 15 |
| Trel10-333UR-ΔdA-er3.3 | 165 | 19 | NA | 6 |

Of the five colonies identified by ethionine selection, three colonies showed increase methionine titers when analyzed by HPLC. The three colonies with increased methionine titers were designated ethionine resistant mutants 1.1, 3.1, and 3.3 (Trel10-333UR-ΔdA-er1.1, Trel10-333UR-ΔdA-er3.1, and Trel10-333UR-ΔdA-er3.3, respectively).

Isolation of Ethionine Resistant *Methanosarcina* Mutants

To select for ethionine resistant *Methanosarcina* mutants, mutagenesis was performed on Trel 42 (*Methanosarcina acetivorans* C2A, DSM 2834) or Trel 9 (*Methanosarcina mazei* G01, DSM 3647). Briefly, strains were grown in 25 mL McCas media plus 5 G/L of methanol without Casamino (for media recipe, see Sarmiento et al., *Methods Enzymol.* 494:44, 2011; which refers to the media McCV, and here is used without Casamino acids or yeast extract) or DSM 120 media without Casitone and Yeast plus 5 G/L Methanol at 37° C. to an $OD_{600}$ of approximately 0.50. Five mL of culture was dispensed into two anaerobic Balch tubes. To one tube, 0.3 mL ethyl methanesulfonate (EMS, 1:50 dilution in McCas no Cas) was added, and to the second tube, 0.3 mL of media was added (control). Tubes were incubated with an 80/20 mix of $N2/CO_2$ at 20 PSIG without shaking at 37° C. for one hour. After one hour incubation, pressure was released and 0.5 mL of each tube was removed and plated on agar plates to determine the kill rate.

The remainder of the culture was washed by centrifuging at 1000×g for 15 minutes, removing the supernatant and washing the harvested cells by resuspending in 5 mL media. These harvesting and washing steps were repeated twice more to remove all the traces of EMS. After the final wash, the harvested cells were suspended in 5 mL media and 1 mL was transferred to three Balch tubes containing 5 mL of media for recovery. To each tube, 0.1 mL 2.5% $Na_2S \times 9H_2O$ was added and then each tube was pressurized to 20 PSIG with 80:20 $N_2/CO_2$ and allowed to recover a minimum of 48 hours at 37° C. The next day, each culture was concentrated to 1.0 mL by centrifugation and either plated on agar plates of appropriate media containing ethionine at 1.25 mg/mL and trimethylamine at 5 g/L or enriched in liquid media at concentrations of ethionine ranging from 0.4 mg/mL to 1.6 mg/mL. For cultures that were enriched prior to plating, the enrichment was performed two times before plating on agar plates containing the same concentration of ethionine. Plates were incubated in an Oxoid anaerobic jar with 10 PSIG of an 80:20 $N_2/CO_2$ gas mix at 37° C. The selection was such that colonies grew only on plates inoculated with EMS treated cells. All work was carried out under anaerobic conditions, unless otherwise indicated.

Three colonies of mutagenized *Methanosarcina acetivorans* Trel42 grew on ethionine, which were tested in serum bottle fermentation (as described in Example 1). The results are summarized below in Table 3.

TABLE 3

Amino Acid Production by Mutant *Methanosarcina* in Serum Tubes

| Strain | Amino Acid (mg/L) | | | |
|---|---|---|---|---|
| | Glycine | Threonine | Lysine | Methionine |
| Trel42 | 9 | 4 | 0 | 3 |
| Trel42-er1.1 | 9 | 3 | 0 | 13 |
| Trel42-er1.2 | 8 | 2 | 0 | 14 |
| Trel42-er1.3 | 8 | 3 | 0 | 16 |

Example 2

Ethionine-Resistant Mutants of *Methanococcus maripaludis* and *Methanosarcina acetivorans*

*Methanococcus maripaludis:*

Genomic DNA was isolated from the *M. maripaludis* mutants overproducing methionine, as well as from the parent strain S2 (Trel10), using the Qiagen DNAeasy Blood & Tissue Kit following the protocol for gram negative bacteria. Polymerase chain reaction (PCR) amplification of the sulfur assimilation ORFs of the MMP1359-MMP1358 operon was performed using the following primers:

```
1359seqF1
(5'-CTATAGAACTAACCCAATG-3'; SEQ ID NO.: 9)

1359seqR1
(5'-GGTGTTGCAGATACTAT-3'; SEQ ID NO.: 10)
```

-continued

```
1359SeqF3
(5'-AGACTTGAACCTTTA-3'; SEQ ID NO.: 11)

1359seqR3
(5'-CGCCAAAATCTTCCCTGC-3'; SEQ ID NO.: 12).
```

These same primers were used as forward and reverse sequencing primers of the MMP1359-MMP1358 operon to obtain complete, overlapping sequence coverage of these ORFs.

Blast comparison of the mutant sequences with the parent strain and previously published sequences showed two distinct mutations in the MMP1359-MMP1358 operon in the methionine producers. Trel10-333UR-ΔdA-er1.1 and Trel10-333UR-ΔdA-er3.1 had a G-A transition at nucleotide position 341 of the MMP1358 ORF, leading to a G114E substitution mutation in the amino acid sequence. Trel10-333UR-ΔdA-er3.3 had a G-A transition at position 1315 of ORF MMP1359, leading to a D439N substitution mutation in the amino acid sequence. The mutations identified in the MMP1359 and MMP1358 ORFs indicate that these genes are associated with the biosynthesis of methionine and likely subject to feedback inhibition by methionine or S-adenosylmethionine.

*Methanosarcina acetivorans:*

Genomic DNA was isolated from each mutant, including the parent strain C2A (Trel42), using Epicentre Masture Pure DNA purification kit and the region containing the putative homocysteine synthase genes (ORF1821 (SEQ ID NO.:29; amino acid sequence of SEQ ID NO.:30) and 1822 in Trel 42 and related ORF in Trel 9) were amplified by PCR. Primers used for amplification and sequencing of the region in Trel 42 were as follows:

```
C2A1821F
(5'-GTATTGAATTGGCAAACT-3'; SEQ ID NO.: 22)

C2A1821R
(5'-ACCGGCTCAGACCCGGTG-3'; SEQ ID NO.: 23)

C2A1821SEQ1
(5'-GGAAAGAACTCGACGTGC-3'; SEQ ID NO.: 24)

C2A1821SEQ2
(5'-ACTGACATTCTTGATTATG-3'; SEQ ID NO.: 25)

C2A1821SEQ3
(5'-CTTGCAGCGCGCAGGCT-3'; SEQ ID NO.: 26)
```

A G/C to A/T transition was found in Trel42mut3 at nucleotide position 1466 in ORF 1821 (SEQ ID NO.31). This mutation results in an S to N amino acid change at position 489 in ORF 1821 (SEQ ID NO.:32).

Example 3

LysC Mutants of Hydrogenotrophic Microorganisms

The isolation of feedback resistant lysC (aspartokinase) mutants of *M. maripaludis* has been previously described. Briefly, wild-type *Methanococcus maripaludis* Trel10 was grown in 25 mL McCas media without Casamino acids (for media recipe, see Sarmiento et al., *Methods Enzymol.* 494: 44, 2011; which refers to the media McCV, and here is used without Casamino acids or yeast extract) at 37° C. to an $OD_{600}$ of approximately 0.20. Five mL of culture was dispensed into two anaerobic Balch tubes. To one tube, 0.3 mL ethyl methanesulfonate (EMS, 1:50 dilution in McCas no Cas) was added, and to the second tube, 0.3 mL of McCas no cas was added (control). Tubes were pressurized with an 80/20 mix of $H_2/CO_2$ to 40 PSIG and incubated without shaking at 37° C. for one hour. After one hour of incubation, pressure was released and 0.5 mL of each tube was removed and plated on McCas agar plates to determine the kill rate.

The remainder of the cultures was dispensed into 5 (EMS treated) or 2 (Control), 1.5 sterile anaerobic microcentrifuge tubes and centrifuged at 1000 g for 15 minutes. The supernatant was removed, the cell pellet washed by resuspending in 1 mL McCas no Cas, and centrifuging again at 1000 g for 15 minutes. This wash was repeated 2× to remove all the traces of EMS. After the final wash, the harvested cells were suspended in 200 μL McCas no Cas and transferred to 5 mL McCas no Cas for recovery. 1 mL 2.5% $Na_2S\times9H_2O$ was added to each tube and each tube was pressurized to 40 PSIG with 80/20 $H_2/CO_2$ and allowed to recover overnight at 37° C. The next morning, each culture was concentrated to 0.1 mL by centrifugation and plated on McCas no Cas plates containing 0.1M threonine and 0.02M AEC. Plates were incubated in an Oxoid anaerobic jar with 10 PSIG of an 80/20 $H_2/CO_2$ gas mix at 37° C. The selection was such that colonies grew only on plates inoculated with EMS treated cells. All work was carried out under anaerobic conditions unless otherwise stated.

The growth rate of EMS generated lysC mutant Trel10-Mut333, which has a G333R mutation (corresponding to LysC amino acid position G277 of *Corynebacterium glutamicum* ATCC 13032), is not affected when grown in presence of lysine and threonine ($OD_{600}$ was measured after 72 hours of incubation at 37° C.; data not shown)—in other words, the mutated aspartokinase of Trel10-Mut333 is not subject to feedback inhibition by lysine and threonine. The aspartate pathway amino acids produced by the Trel10-Mut333 mutant were identified by HPLC (data not shown). The derivatizing agent ortho-phthalaldehyde (OPA) was used in an automated derivatization reaction on an autosampler and was done pre-column. The reaction mixture was buffered at pH 10.2 (via Borate Buffer), which allowed direct derivatization of acid hydrolyzed protein/peptide samples. The amino acids of interest were reacted first with OPA using 3-mercaptopropionic acid (3-MPA). The incorporation of the 3-MPA into the indoles decreases their hydrophobicity, and as a result, the OPA-derivatives eluted chromatographically. The production profile of the Trel10-Mut333 mutant as compared to the parent strain was as follows (and generally similar in all mutants identified, data not shown): alanine (5 mg/L), lysine (8 mg/L), threonine (21 mg/L), and glycine (78 mg/L).

Mutations in the *M. maripaludis* lysC were verified by extracting genomic DNA using the Qiagen DNAeasy Blood & Tissue Kit following the protocol for gram negative bacteria. LysC targets were amplified using the Easy-A high fidelity polymerase with forward primer (LysCfor1-5'GGGACGGCGCAACAAATGG3'; SEQ ID NO.:13) and reverse primer (LysCrev1-5'GGAGATAGTGAGAC-CCCTGGAGT3'; SEQ ID NO.:14). Amplified DNA was mixed with either LysCfor1 or LysCrev1 and sequenced (Operon). One spontaneous mutant and 8 chemically induced mutants were identified. In addition to mutation at position G277 previously identified in *Corynebacterium* (in this case, G277R), new mutation positions not previously identified in *Corynebacterium* were found, including S302P and G359E (numbering according to amino acid positions from LysC of *Corynebacterium glutamicum* ATCC 13032).

Example 4

Uracil Phosphoribosyltransferase Deletion and RepA Insertion in Hydrogenotrophic Microorganisms In order to improve plasmid transformation efficiency, lysC mutant *Methanococcus maripaludis* Trel10-Mut333 was modified on the genomic level by replacing the uracil phosphoribosyltransferase (upp) gene (Locus MMP0680) with the gene encoding replication protein A (repA, with its own promoter), referred to as Trel10-333UR. The repA allows for efficient transformation of any plasmid having repA, such as a plasmid derived from or based on the repA-containing pURB500 plasmid (see Tumbula et al., *J. Bacteriol.* 179:2976, 1997). The loss of uracil phosphoriboxyltransferase activity gives the modified *M. maripaludis* a 6-azaurcil resistance phenotype.

Briefly, the repA gene was amplified (along with its promoter) from the genomic DNA of *Methanococcus maripaludis* S001 (Walters et al., *App. Environ. Microbiol.* 77:2549, 2011) with primers TKH_038 (5'aaattatgaggcgcgcctccctgaagaagaagagag3'; SEQ ID NO.:27) and TKH_039 (5'tgcttattcggcgcgccagttccattttaccacc3'; SEQ ID NO.:28). The amplified repA fragment was cloned using the In-Fusion® HD cloning kit (Clontech) into pCR® 2.1-TOPO® TA vector linearized with AscI. The final plasmid was named pKH11. The XbaI-BamHI fragment from pKH11 was cloned into pMEV1 (Gardner WL (2000) Expression vectors for the methane-producing archaeon *Methanococcus maripaludis*. Dissertation, University of Georgia) linearized with restriction enzymes NheI and BglII. The resultant suicide vector carrying a puromycin resistance gene was named pKH20.

Plasmid pKH20 was transformed into Trel10-Mut333 essentially as described by Sarmiento et al. (2011), and transformants were selected on McCAS plates containing puromycin (2.5 mg/L). Transformant colonies that grew in presence of puromycin were transferred into McCAS liquid medium supplemented with 6-azauracil (0.25 mg/ml) and grown overnight. A portion of the overnight culture was transferred into fresh McCAS medium supplemented with 0.5 mg/ml 6-azauracil and grown overnight again. The cultures were diluted and then spread onto McCAS plates containing 0.25 mg/ml 6-azauracil. After 5 days, individual colonies were replica plated onto McCAS plates with or without puromycin. Colonies that failed to grow in presence of puromycin were transferred into McCAS liquid medium supplemented with 6-azauracil (0.25 mg/ml) to confirm resistance. The replacement of the upp gene with the repA gene on the Trel10-Mut333 genome was verified by PCR using the following primers: uptdelconf1 (5'-caattactgaacccaaagaccat-3'; SEQ ID NO.:14) and uptdelconf2 (5'-aatagttaccggcgttacaatca-3'; SEQ ID NO.:15). The 6-azauracil resistant/puromycin sensitive colony with the verified upp gene replacement with the repA gene was named Trel10-333UR.

Example 5

DapA Deletion in Hydrogenotrophic Microorganisms

Construction of Trel10-333UR-ΔdA—a dapA deletion for increased methionine production was generated using essentially the same markerless mutagenesis method described in Sarmiento et al. (2011). An approximately 2.4 kb fragment from the *M. maripaludis* S2 (Trel10) genome containing the dapA gene, along with upstream and downstream regions, was synthesized via PCR using primers DapAfor2 (5'-tccctgatcgatagaaagtgtagt-3'; SEQ ID NO.:16) and DapArev2 (5'-ttgccgatgaaattaaagtgaaa-3; SEQ ID NO.:17) and cloned into plasmid pTOPO to create pJB012. An in-frame deletion fragment of the dapA gene was created by using outward PCR with primers DapAdelfor2 (5'-gcgggcgcgccgcataattacaccttatgcgttc-3'; SEQ ID NO.:18) and DapAdelrev2 (5'-gcgggcgcgcctaatcacggttcgtgatactat-3; SEQ ID NO.:19) both of which contain a 5' AscI site. The PCR products were purified, digested with AscI and ligated into pTOPO to create pJB013. Finally, a fragment containing the upp::neo gene was PCR amplified using primers uppneoF (5'-attacgccaagcttggtaccactctcttcttcttcaggga-3'; SEQ ID NO.:20) and uppneoR (5'-gtggatccgagctcggtacctgagatccccgcgctggagg-3; SEQ ID NO.:21) from pKH14 and cloned into the KpnI site of pJB013 to create pJB015.

pJB015 was transformed into Trel10-333UR (as described previously) selecting for neomycin (500 ug mg/ml) resistant colonies on agar plates. A single crossover event at a chromosomal dapA gene was confirmed by PCR. Colonies with a single crossover were grown in non-selective media for 24 hours to allow a double crossover event, and then plated on McCAS media containing 100 mg/L lysine and 0.25 ug/ml 6-azauracil. Colonies were patched to McCAS plates with or without lysine. PCR confirmation of the dapA deletion was performed on colonies requiring lysine for growth. One such colony was designated Trel10-333UR-ΔdA.

Example 6

Overexpression of Methionine Biosynthetic Genes

Any gene of the *Methanococcus maripaludis* Trel10 methionine biosynthetic pathway, including lysC, deregulated lysC, asd, MMP1358 ORF, MMP1359 ORF, deregulated MMP1358 ORF, deregulated MMP1359 ORF or methionine synthase, may be overexpressed by removing the native promoter and replacing it with a strong constitutive promoter. In one case, a deregulated MMP1358 ORF or a deregulated MMP1359 ORF, each with and without a methionine synthase (MetE), were operably linked to the constitutive histone gene hmv promoter on a replicative plasmid and introduced into *M. maripaludis* Trel10. In another case the deregulated ORF1358 and Orf 1359 were operably linked to the hmv promoter and introduced into Trel10-Mut333. Amino acid production in serum bottles (as described in Example 1) and fermentors (as described in Example 9) was measured and the results are summarized in Tables 4 and 5.

TABLE 4

Amino Acid Production by Engineered *M. maripaludis* in Serum Tubes

| Strain | Amino Acid (mg/L) | | | |
|---|---|---|---|---|
| | Glycine | Threonine | Lysine | Methionine |
| Trel10-er3.1 + er3.3 | 6.6 | 20.7 | 0 | 107 |
| Trel10-er3.1 + er3.3 + E | 0 | 21 | 0 | 97 |

TABLE 4-continued

Amino Acid Production by Engineered *M. maripaludis* in Serum Tubes

| Strain | Amino Acid (mg/L) | | | |
|---|---|---|---|---|
| | Glycine | Threonine | Lysine | Methionine |
| Trel10-Mut333 + er3.1 + er3.3 | 154 | 44 | 10 | 66 |

TABLE 5

Amino Acid Production by Engineered *M. maripaludis* by Fermentation

| Strain | Amino Acid (mg/L) | | | |
|---|---|---|---|---|
| | Glycine | Threonine | Lysine | Methionine |
| Trel10-er3.1 + er3.3 + E | 62 | 97 | 5 | 312 |

*Methanococcus maripaludis* Trel10 constitutively expressing deregulated MMP1358 and MMP1359 ORFs (Trel10-er3.1+er3.3) produced a significant amount of methionine (107 mg/L, Table 4). The addition of a deregulated LysC (Trel10-Mut333+er3.1+er3.3) did not improve methionine production, but instead more glycine, threonine and lysine were produced. These data indicate that wild-type Trel10 may be naturally 'deregulated' since overproduction of methionine results in a drop in lysine and threonine levels and, therefore, these amino acids are not present in high enough amounts to trigger feedback inhibition of LysC. Moreover, these data indicate that overexpression of deregulated MMP1358 and MMP1359 ORFs result in very specific overproduction of methionine.

Example 7

Methionine Export from Hydrogenotrophic Microorganisms

A candidate brnFE or metT methionine exporter gene from *Corynebacterium glutamicum* is isolated and examined for functionality. Further mutations are optionally introduced to increase function, or the export gene is overexpressed by operably linking to a stronger promoter, or a functional exogenous brnFE or metT gene is introduced into *M. maripaludis*. The overproduced methionine can be easily recovered and/or isolated from the culture medium.

Example 8

Altering Carbon Flux to Methionine Production in Hydrogenotrophic Microorganisms The main carbon flow of a hydrogenotrophic microorganism (e.g., *M. maripaludis*) may be shifted in a variety of ways to provide more carbon to methionine biosynthesis. For example, limiting the flow of carbon from pyruvate to phosphoenolpyruvate (PEP) is achieved by inactivating or down regulating the PEP synthase gene. In addition, the isoleucine pathway (if present) is optionally knocked out, which preserves pyruvate and acetyl CoA used by this pathway. Inactivation or reduction of particular enzymatic activities may be introduced by genetic engineering (e.g., gene or gene portion deletion) or by selecting for inactivation by mutation (e.g., spontaneous or induced). Alternatively, the pyruvate carboxylase gene is optionally overexpressed to funnel more carbon from pyruvate to oxaloacetate (OAA). In addition, the aspartate aminotransferase gene is optionally overexpressed to convert more OAA to aspartate. Overexpression may be accomplished, for example, by providing multiple copies of a gene or by altering the promoter region to provide stronger expression.

Example 9

Culturing Non-Natural and Recombinant Hydrogenotrophic Microorganisms in a Bioreactor

*M. maripaludis* is cultured in a bubble column bioreactor under anaerobic conditions for about 72 hours to 120 hours until the culture reaches a steady state condition, which can be done in a series of consecutive vessels of increasing volume (e.g., starting at 50 ml, using this culture to seed 10 L, and then using this culture to seed 300 L or more) so that a very large volume of dense culture is reached. During this time, the system will be running in a fed batch mode, wherein the syngas is continuously fed to the fermentation broth. The broth itself will not be exchanged. Once an appropriate $OD_{600}$ is reached (as measured by spectrophotometer), then a continuous culture process will be initiated, wherein an exchange of the media/broth is begun. The rate of exchange will be determined in view of the $OD_{600}$ of the culture within the fermenter. For example, from about 1.5 to about 3.0 complete volumes of broth are exchanged per day.

The culture is maintained at a temperature of about 37° C., but might fluctuate in the range of about 35° C. to about 40° C., maintained at a pH of about 7.0-7.2 (adjusting pH as needed with HCl and/or NaOH), and maintained at an $OD_{600}$ from about 1.5 to about 2.0. The syngas is comprised of $H_2$:$CO_2$ at a ratio ranging from about 4:1 to about 3:1, which may include carbon monoxide at a range of about 0% to about 5% (optimum is at most 1%), and may include other minor contaminants. The syngas flow rate is dictated by the specific design of the bubble or trickle column used in the process.

The various embodiments described above can be combined to provide further embodiments. All of the patent and non-patent publications referred to in this specification or listed in the Application Data Sheet are incorporated herein by reference, in their entirety. Aspects of the embodiments can be modified, if necessary to employ concepts of the various patents, applications and publications to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

All of the U.S. patents, U.S. patent application publications, U.S. patent applications, foreign patents, foreign patent applications and non-patent publications referred to in this specification, including U.S. provisional patent application Ser. No. 62/157,797, filed May 6, 2015, are incorporated herein by reference, in their entireties to the extent not inconsistent with the present description.

What is claimed is:

1. A non-natural methanogenic archaea, wherein the non-natural methanogenic archaea metabolizes a $CO_x$ substrate, optionally in the presence of $H_2$, to produce methionine at a higher level than a parent methanogenic archaea and wherein the non-natural methanogenic archaea expresses at least one polypeptide chosen from: (a) a polypeptide selected from the group consisting of: SEQ ID NOS:4, 8, and 32; (b) a polypeptide having an amino acid sequence comprising at least 70% sequence identity to at least one of SEQ ID NOS:4 or 8, wherein said SEQ ID NO: 4 has a D439 mutation and said SEQ ID NO: 8 has a G114 mutation and wherein the polypeptide is deregulated for one or more feedback inhibitors; (c) a polypeptide having an amino acid sequence comprising at least 80% sequence identity to SEQ ID NO: 32, wherein said SEQ ID NO: 32 has a S489 mutation and wherein the polypeptide is deregulated for one or more feedback inhibitors; or (f) a polypeptide encoded by a nucleic acid molecule, wherein the nucleic acid molecule comprises at least 70% sequence identity to SEQ ID NO: 1 and the nucleic acid has one or more mutations in a region designated by a forward primer of SEQ ID NO: 11 and a reverse primer of SEQ ID NO: 10, wherein said one or more mutations results in a substitution, deletion or insertion to an amino acid of the encoded protein as compared the polypeptide encoded by SEQ ID NO:1 and wherein the encoded protein with the amino acid substitution, deletion or insertion is deregulated for one or more feedback inhibitors.

2. The non-natural methanogenic archaea according to claim 1, wherein the polypeptide of claim 1(f) is a polypeptide encoded by a nucleic acid molecule of claim 1(f), such that the polypeptide has an amino acid sequence comprising at least 70% sequence identity to SEQ ID NO:3 and a mutation at residue D439, wherein the residue numbering also corresponds to residue positions of MMP1359 from *Methanococcus maripaludis* S2 DSM14266.

3. The non-natural hydrogenotrophic microorganism methanogenic archaea according to claim 1, wherein the polypeptide of claim 1(d) is a polypeptide encoded by a nucleic acid molecule of claim 1(d), such that the polypeptide has an amino acid sequence comprising at least 70% sequence identity to SEQ ID NO:7 and a mutation at residue G114, wherein the residue numbering also corresponds to residue positions of MMP1358 from *Methanococcus maripaludis* S2 DSM14266.

4. The non-natural methanogenic archaea according to claim 1, wherein the polypeptide of claim 1(e) is a polypeptide encoded by a nucleic acid molecule of claim 1(e), such that the polypeptide has an amino acid sequence comprising at least 70% sequence identity to SEQ ID NO:30 and a mutation at residue S489, wherein the residue numbering also corresponds to residue positions of C2A1821 from *Methanosarcina acetivorans* C2A.

5. The non-natural methanogenic archaea according to claim 2, wherein the mutation at D439 is a D439N substitution.

6. The non-natural hydrogenotrophic microorganism methanogenic archaea according to claim 3, wherein the mutation at G114 is a G114E substitution.

7. The non-natural hydrogenotrophic microorganism methanogenic archaea according to claim 4, wherein the mutation at S489 is a S489N substitution.

8. The non-natural methanogenic archaea of claim 1, wherein the non-natural methanogenic archaea further comprises a deregulated aspartokinase activity, a methionine synthase, or both.

9. The non-natural methanogenic archaea of claim 8, wherein the deregulated aspartokinase activity is an exogenous aspartokinase and is encoded by (a) a mutant lysC gene comprising a mutation at a threonine binding site, optionally wherein the threonine binding site mutation is at residue I272, D274, G277, E278, A279, D294, Q298, N372, N374, I375, or any combination thereof, wherein the residue numbering corresponds to residue positions encoded by lysC (GenBank Accession No. CAF18822.1) of *Corynebacterium glutamicum* ATCC 13032; (b) a mutant lysC gene comprising a mutation at a lysine binding site, optionally wherein the lysine binding site mutation is at residue I291, I293, D294, T361, S381, E382, or any combination thereof, wherein the residue numbering corresponds to residue positions encoded by lysC (GenBank Accession No. CAF18822.1) of *Corynebacterium glutamicum* ATCC 13032; (c) a mutant lysC gene comprising a mutation at a lysine and threonine binding site, optionally wherein the residue numbering corresponds to residue positions encoded by lysC (GenBank Accession No. CAF18822.1) of *Corynebacterium glutamicum* ATCC 13032; and/or (d) a mutant lysC gene comprising a mutation at a site other than a lysine or threonine binding site, optionally wherein the mutation at a site other than a lysine and threonine binding site is at residue F283, N299, S301, S302, T308, T311, T336, G359, F364, M365, T380, R384, S386, or any combination thereof, wherein the residue numbering corresponds to residue positions encoded by lysC (GenBank Accession No. CAF18822.1) of *Corynebacterium glutamicum* ATCC 13032.

10. The non-natural methanogenic archaea of claim 1, wherein the non-natural methanogenic archaea further comprises an exogenous nucleic acid molecule encoding one or more polypeptides from a methionine biosynthetic pathway selected from aspartokinase, aspartyl semialdehyde dehydrogenase, homoserine dehydrogenase, homoserine O-acetyltransferase, homoserine O-transsuccinyltransferase, O-succinylhomoserine lyase, cystathionine γ-synthase, cystathionine β-lyase, O-acetylhomoserine sulfhydrylase, homocysteine S-methyltransferase, methionine synthase (cobalamin dependent or independent), and any combination thereof; and optionally wherein: (a) (i) the exogenous nucleic acid molecule encodes a homoserine dehydrogenase, a serine acetyltransferase, or both, and optionally the homoserine dehydrogenase, serine acetyltransferase, or both are overexpressed and/or the homoserine dehydrogenase, serine acetyltransferase, or both are deregulated; or (ii) the exogenous nucleic acid molecule encodes a homoserine O-acetyltransferase, an O-acetylhomoserine sulfhydrylase, or both and optionally the homoserine O-acetyltransferase, O-acetylhomoserine sulfhydrylase, or both are overexpressed and/or the homoserine O-acetyltransferase, O-acetylhomoserine sulfhydrylase or both are deregulated; (b) the exogenous nucleic acid molecule encodes a methionine synthase, and optionally wherein the methionine synthase is overexpressed as compared to a parent or wild-type methanogenic archaea lacking the exogenous nucleic acid molecule encoding methionine synthase.

11. The non-natural methanogenic archaea of claim 10, wherein (a) one or more nucleic acid molecules encoding polypeptides from a lysine biosynthetic pathway are knocked out or have reduced activity compared to a parent or wild-type methanogenic archaea, and/or (b) one or more nucleic acid molecules encoding polypeptides from a threonine biosynthetic pathway are knocked out or have reduced activity compared to a parent or wild-type methanogenic archaea; and/or (c) optionally wherein a nucleic acid molecule that encodes a dihydrodipicolinate synthase, a homoserine kinase, a threonine dehydratase, a threonine aldolase, a serine hydroxymethyl transferase, or any combination thereof are knocked out or encode a reduced activity dihydrodipicolinate synthase mutant, a homoserine kinase mutant, threonine dehydratase mutant, threonine aldolase mutant, serine hydroxymethyl transferase mutant, or any combination thereof, wherein said reduced activity is in comparison to a parent or wild-type methanogenic archaea.

12. The non-natural methanogenic archaea of claim 9, wherein the exogenous nucleic acid molecule is (a) integrated in the genome of the non-natural hydrogenotrophic microorganism, (b) in a self-replicating vector in the non-natural hydrogenotrophic microorganism.

13. The non-natural methanogenic archaea of claim 1, wherein the non-natural methanogenic archaea (a) is a lysine auxotroph, threonine auxotroph, glycine auxotroph, or any combination thereof, (b) has reduced phosphoenolpyruvate synthase activity, increased pyruvate kinase activity, or both, when compared to a parent or wild-type methanogenic archaea or (c) has increased pyruvate carboxylase activity, increased 5-methyltetrahydrofolate corrinoid/iron sulfur protein methyltransferase activity, increased pyruvate synthase, increased acetyl-CoA synthase, increased aspartate aminotransferase activity, or any combination thereof, wherein said increased activity is compared to a parent or wild-type methanogenic archaea.

14. The non-natural methanogenic archaea of claim 1, wherein the CO.sub.x substrate is a $H_2/CO_X$ substrate comprised of $H_2$, CO, and $CO_2$, and the $H_2/CO_X$ substrate is optionally comprised of syngas or water-gas shifted syngas.

15. The non-natural methanogenic archaea according to claim 14, wherein (a) the ratio of $CO_2$ to $H_2$ ranges from about 1:50 to about 10:1, respectively, (b) the ratio of $CO_2$ to $H_2$ ranges from about 1:2 to about 1:4, respectively; and optionally wherein the total amount of CO is no more than about 1%.

16. The non-natural methanogenic archaea of claim 1, wherein the methanogenic archaea does not produce cytochromes.

17. The non-natural methanogenic archaea of claim 1, wherein the methanogenic archaea produces cytochromes.

18. The non-natural methanogenic archaea of claim 1, wherein the non-natural methanogenic archaea (a) expresses or overexpresses an exporter of methionine and/or (b) further comprises an exogenous nucleic acid molecule that encodes an exporter of methionine.

19. A method for producing methionine, comprising culturing a non-natural methanogenic archaea of claim 1 in the presence of a $H_2/CO_X$ substrate under conditions for a time sufficient to produce methionine, wherein the non-natural methanogenic archaea: (a) expresses one or more sulfur assimilation polypeptides having increased activity as compared to a parent or wild-type methanogenic archaea; (b) overexpresses one or more sulfur assimilation polypeptides; or (c) comprises altered regulation of one or more sulfur assimilation polypeptides, wherein the non-natural methanogenic archaea produces methionine at a higher level than a parent or wild-type methanogenic archaea.

20. A system for producing methionine, comprising: (a) a source of gas comprising a $CO_x$ substrate, optionally in the presence of Hz; (b) a bioreactor comprising a non-natural methanogenic archaea of claim 1 comprising an exogenous nucleic acid molecule encoding a sulfur assimilation polypeptide; and (c) a connector disposed between the gas source and the bioreactor to allow flow of the gas into the bioreactor; wherein the non-natural methanogenic archaea metabolizes the $CO_X$ substrate, optionally in the presence of $H_2$, to overproduce methionine as compared to a parent or wild-type methanogenic archaea.

21. The system of claim 20, wherein the bioreactor is a liquid phase, bubble column, or trickle bed bioreactor.

22. The system of claim 20, wherein the $CO_x$ substrate is a $H_2/CO_x$ substrate comprised of syngas or water-gas shifted syngas.

* * * * *